US009005949B2

(12) United States Patent
Oxvig et al.

(10) Patent No.: US 9,005,949 B2
(45) Date of Patent: *Apr. 14, 2015

(54) PREGNANCY-ASSOCIATED PLASMA PROTEIN-A2 (PAPP-A2) POLYNUCLEOTIDES

(71) Applicant: Como Biotech ApS, Arhus C (DK)

(72) Inventors: Claus Oxvig, Viby (DK); Michael Toft Overgaard, Artus C. (DK)

(73) Assignee: Como Biotech ApS, Arhus C (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/625,088

(22) Filed: Sep. 24, 2012

(65) Prior Publication Data

US 2013/0095569 A1    Apr. 18, 2013

Related U.S. Application Data

(60) Continuation of application No. 12/914,312, filed on Oct. 28, 2010, which is a division of application No. 11/451,495, filed on Jun. 13, 2006, now abandoned, which is a continuation of application No. 09/983,025, filed on Oct. 22, 2001, now Pat. No. 7,083,940.

(60) Provisional application No. 60/241,840, filed on Oct. 20, 2000.

(30) Foreign Application Priority Data

Oct. 20, 2000  (DK) .................................. 2000 01571

(51) Int. Cl.
| | |
|---|---|
| C12N 5/10 | (2006.01) |
| C12N 15/00 | (2006.01) |
| C12N 1/21 | (2006.01) |
| C12P 21/00 | (2006.01) |
| C07H 21/00 | (2006.01) |
| C07K 14/47 | (2006.01) |
| C12Q 1/37 | (2006.01) |
| C12Q 1/68 | (2006.01) |
| G01N 33/68 | (2006.01) |
| C12N 9/64 | (2006.01) |
| A61K 38/00 | (2006.01) |

(52) U.S. Cl.
CPC .............. *C07K 14/4715* (2013.01); *A61K 38/00* (2013.01); *C12N 9/6489* (2013.01); *C12Q 1/37* (2013.01); *C12Q 1/6876* (2013.01); *G01N 33/689* (2013.01)

(58) Field of Classification Search
USPC ............... 435/69.1, 226, 320, 325, 252.3, 23; 530/350; 536/23.2
See application file for complete search history.

(56) References Cited

U.S. PATENT DOCUMENTS

| | | | |
|---|---|---|---|
| 4,554,101 A | 11/1985 | Hopp | |
| 4,683,195 A | 7/1987 | Mullis et al. | |
| 4,965,188 A | 10/1990 | Mullis et al. | |
| 5,595,915 A | 1/1997 | Geysen | |
| 6,013,478 A | 1/2000 | Wells et al. | |
| 6,500,630 B2 | 12/2002 | Conover et al. | 435/7.94 |
| 6,656,700 B2 * | 12/2003 | Gu et al. | 506/14 |
| 2002/0102252 A1 | 8/2002 | Gu et al. | |
| 2008/0071151 A1 | 3/2008 | Sogin et al. | |
| 2010/0304412 A1 | 12/2010 | Cuckle et al. | |
| 2011/0091920 A1 | 4/2011 | Oxvig et al. | |

FOREIGN PATENT DOCUMENTS

| | | |
|---|---|---|
| EP | 0044710 A1 | 1/1982 |
| WO | WO9802751 A1 | 1/1998 |
| WO | WO00/54806 | 9/2000 |
| WO | WO0054806 A1 | 9/2000 |
| WO | WO 01 958 55 A2 | 6/2001 |
| WO | WO01/75067 | 10/2001 |
| WO | WO0195855 A2 | 12/2001 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Cameron, E., Molecular Biotechnology 7:253-265, 1997.*
Houdebine, L., Journal of Biotechnology 98:145-160, 2002.*
Phillips, A., J. Pharm. Pharmacology 53:1169-1174, 2001.*
Gardlik et al., Med. Sci. Monit. 11(4):RA110-121, 2005.*
Farr et al., Biochim. Biophys. Acta, 1493:356-362, Oct. 2, 2000.*
Haaning et al., Eur. J. Biochem. 237:159-163, 1996.*
Haaning et al., GenBank accession No. U28727, 1996.*
Farr et al., GenBank accession No. AJ278348, Oct. 4, 2000.*
Overgaard et al., JBC 275(40):31128-31133, Jul. 2000.*
Ausubel, F., Current Protocols in Molecular Biology, Hybridization Analysis of DNA Blots, pp. 2.10.8-2.10.11, 1993.*

(Continued)

*Primary Examiner* — Delia Ramirez
(74) *Attorney, Agent, or Firm* — McLane, Graf, Raulerson & Middleton, PA

(57) ABSTRACT

The present invention provides pregnancy associated plasma protein A2 (PAPP-A2), its nucleotide and amino acid sequences, antisense molecules to the nucleotide sequences which encode PAPP-A2, expression vectors for the production of purified PAPP-A2, antibodies capable of binding specifically to PAPP-A2, hybridization probes or oligonucleotides for the detection of PAPP-A2-encoding nucleotide sequences, genetically engineered host cells for the expression of PAPP-A2, and methods for screening for pathologies in pregnant and non-pregnant patients. Methods for screening for altered focal proliferation states in pregnant and/or non-pregnant patients, which include detecting levels of PAPP-A2, are also described.

11 Claims, 21 Drawing Sheets

(56) References Cited

OTHER PUBLICATIONS

Oliner et al., Nature 358:80-83, 1992.*
Nishizawa et al., Molecular Human Reproduction 14(10):595-608, 2008.*
Huber et al., Hepatology 6(2):209-219, 1986.*
Lawrence J B et al, "The insulin-like growth factor (IGF)-dependent IGF binding protein-4 protease secreted by human fibroblasts is pregnancy-associated plasma protein-A", Proc.Natl. Acad. Sci, USA, vol. 96, pp. 3149-3153, Mar. 1999.
Kristensen T et al., "Amino acid sequence of human pregnancy-associated plasma protein-A derived from cloned cDNA", Biochemistry, 33, 1592-1598, Feb. 1994.
Overgaard M T et al, "Expression of recombinant human pregnancy-associated plasma protein-A and identification of the proform of eosinophil major basic protein as its physiological inhibitor", The Journal of Biological Chemistry, vol. 275, No. 40, 6, pp. 31128-31133, Oct. 2000.
Oxvig C et al., "Identification of angiotensinogen and complement C3dg as novel proteins binding the proform of eosinophil major basic protein in human pregnancy serum and plasma", The Journal of Biological Chemistry, vol. 270, No. 23, pp. 13645-13651, Issue of Jun. 9, 1995.
Overgaard M T et al, "Messenger ribonucleic acid levels of pregnancy-associated plasma protein-A and the proform of eosinophil major basic protein: Expression in human reproductive and nonreproductive tissues", Biology of Reproduction, 61, 1083-1089, Oct. 1999.
Bonno M et al, "Localization of pregnancy-associated plasma protein-A and colocalization of pregnancy-associated plasma protein-A messenger ribonucleic acid and eosinophil granule major basic protein messenger ribonucleic acid in placenta", Abstract, Laboratory Investigation, vol. 71, No. 4, pp. 560-566, Oct. 1994.
Erickson G F et al, "The physiology of folliculogenesis: the role of novel growth factors", Fertility and Sterility, vol. 76, No. 5, pp. 943-949, Nov. 2001.
Wald N J et al, "First trimester serum screening for Down's Syndrome", Prenatal Diagnosis, vol. 15, pp. 1227-1240, Dec. 1995.
Christiansen et al., "Qualification and characterization of pregnancy-associated complexes of angiotensinogen and the proform of eosinophil major basic protein in serum and amniotic fluid", Clinical chemistry, vol. 46, No. 8, Aug. 2000, pp. 1099-1105.
Oxvig C. et al., "Circulating human pregnancy-associated plasma protein-A Is disulfide-bridged to the proform of eosinophil major basic protein", The Journal of Biological Chemistry, vol. 268, No. 17, Jun. 15, 1993, pp. 12243-12246.
Gordon C S Smith et al., "Early pregnancy levels of pregnancy-associated plasma protein A and the risk of intrauterine growth restriction, premature birth, preeclampsia, and stillbirth", The Journal of Clinical Endocrinology & Metabolism, vol. 87, No. 4, Apr. 2002, pp. 1762-1767.
Guidice L C et al., "Identification and regulation of the IGFBP-4 protease and its physiological inhibitor in human trophoblasts and endometrial stroma: Evidence for paracrine regulation of IGF-II bioavailability in the placental bed during human implantation", The Journal of Clinical Endocrinology & Metabolism, vol. 87, No. 5, May 2002, pp. 2359-2366.
Laursen, et al., "Pregnancy-associated plasma protein-A (PAPP-A) cleaves insulin-like growth factor binding protein (IGFBP)-5 independent of IGF: implications for the mechanism of IGFBP-4 proteolysis by PAPP-A", FEBS Letters, vol. 504, pp. 36-40, 2001.
Spencer, et al., "Screening for trisomy 13 by fetal nuchal translucency and maternal serum free β-hCG and PAPP-A at 10-14 weeks of gestation", Prenat Diagn, vol. 20, pp. 411-416, 2000.
Wald, et al., "First trimester concentrations of pregnancy associated plasma protein A and placental protein 14 in Down's syndrome", BMI, vol. 305, p. 28, 1992.
Wald, et al., "Integrated Screening for Down's Syndrome Based on Tests Performed During the First and Second Trimesters", N Engl J Med, vol. 341, pp. 461-467, 1999.
Westergaard, e t al., "Pregnancy-Associated Plasma Protein A: A Possible marker in the Classification and Prenatal Diagnosis of Cornelia De Lange Syndrome", Prenat Diagn, vol. 3, pp. 225-232, 1983.
Haaning et al., PIR accession No. S65464, Nov. 1996.
Witkowski et al., Biochemistry 38:11643-11650, 1999.
Broun et al., Science 282:1315-1317, 1998.
Van de Loo et al., Proc. Natl. Acad. Sci. 92:6743-6747, 1995.
Seffernick et al., J. Bacteriol. 163(8):2405-2410, 2001.
Spencer et al., Prenat Diagn 28(1):7-10, 2008.
Hajek et al, Physiol Res 57(1) in press, 2008.
Futterman et al., Am J Crit Care 11(2):168-172, 2002.
Qin et al., Clinical Chemistry 43(12):2323-2332, 1997.
Bayes-Genis et al., The New England Journal of Medicine 345(14):1022-1029, Oct. 4, 2001.
Bersinger et al., European Journal of Endocrinology 147:785-793, 2002.
Martin Farr, et al., Pregnancy-associated plasma protein-E (PAPP-E), Biochimica et Biophysics Acta 1493 (2000):356-362, manuscript acceptance date Jul. 27, 2000.
Michael T. Overgaard, et al., Pregnancy-associated plasma protein-A2 (PAPP-A2), a novel insulin-like growth factor-binding protein-5 proteinase. The Journal of Biological Chemistry, 276(24):21849-21853 (Jun. 15, 2001).
N.M. Page, et al., The characterization of pregnancy associated plasma protein-E and the identification of an alternative splice variant., Placenta 22:681-687 (2001), manuscript acceptance date May 14, 2001.
Winn et al. "Severe Preeclampsia-Related Changes in Gene Expression at the Maternal-Fetal Interface Include Sialic Acid-Binding Immunoglobulin-Like Lectin-6 and Pappalysin-2," The Endocrine Society, vol. 150, No. 1, pp. 452-462 (2009).
Maurer et al., "Proteins and polypeptides as antigens," Meth. Enzymology, 70: 49-70 (1980).
Farr et al., "Pregnancy-associated plasma protein-E (PAPP-E)," Biochim. Biophys. Acta 1493: 356-362, and sequence alignment with instant SEQ ID No. 2 (2000).
Jarvik et al., "Epitope tagging," Annu. Rev. Genet., 32: 601-618 (1988).
Campbell, "Monoclonal Antibody Technology," Elsevier, Amsterdam, pp. 1-4 and 29 (1984).
Harlow et al., "Antibodies. A Laboratory Manual," Cold Spring Harbor Laboratory, Cold Spring Harbor, pp. 72-77 (1988).
Biagiotti et al., "Maternal Serum Screening for Trisomy 18 in the First Trimester of Pregnancy", Prenat Diagn, vol. 18, pp. 907-913, 1998.
Brambati, et al., "Low maternal serum levels of pregnancy associated plasma protein A (PAPP-A) in the first trimester in association with abnormal fetal karyotype", BR J Obstet Gynaecol, vol. 100, pp. 324-326, 1993.
Canick, et al., "Comparison of Serum Markers in First-Trimester Down Syndrome Screening", Obstetrics & Gynecology, vol. 108, No. 5, pp. 1192-1199, 2006.
Gyrup, et al., "Quantification of Proteolytically Active Pregnancy-Associated Plasma Protein-A with an Assay Based on Quenched Fluorescence", Clinical Chemistry, vol. 53:5, pp. 947-954, 2007.
Haddow, et al., "Screening of Maternal Serum for Fetal Down's Syndrome in the First Trimester", N Eng J Med, vol. 338, pp. 955-961, 1998.
Hallahan, et al., "First trimester biochemical screening for Down syndrome: free beta hCG versus intact hCG", Prenatal Diagnosis, vol. 20, pp. 785-789, 2000.
Miller, et al., "fetus", p. 419, Encyclopedia and Dictionary of Medicine, Nursing, and Allied Health (U.B. Saunders Co. 1983).
Ndumbe, et al., "Prenatal Diagnosis in the First Trimester of Pregnancy", Obstetrical and Gynecological Survey, vol. 63, No. 5, pp. 317-328, 2008.
Qin et al., "Molecular Distinction of Circulating Pregnancy-Associated Plasma Protein A in Myocardial Infarction and Pregnancy", Clinical Chemistry, vol. 51;1, pp. 75-83, 2005.

* cited by examiner

Figure 1 A

```
ATGATGTGCTTAAAGATCCTAAGAATAAGCCTGGCGATTTTGCTGGGTGGCACTCTGT      60
 M  M  C  L  K  I  L  R  I  S  L  A  I  L  A  G  W  A  L  C    (20)

TCTGCCAACTCTGAGCTGGGCTGGACACGCAAGAAATCCTTGGTTGAGAGGGAACACCTG     120
 S  A  N  S  E  L  G  W  T  R  K  K  S  L  V  E  R  E  H  L    (40)

AATCAGGTGCTGTTGGAAGGAGAACGTTGTTGGCTGGGGGCCAAGGTTCGAAGACCCAGA     180
 N  Q  V  L  L  E  G  E  R  C  W  L  G  A  K  V  R  R  P  R    (60)

GCTTCTCCACAGCATCACCTCTTTGGAGTCTACCCCAGCAGGGCTGGGAACTACCTAAGG     240
 A  S  P  Q  H  H  L  F  G  V  Y  P  S  R  A  G  N  Y  L  R    (80)

CCCTACCCCGTGGGGGAGCAAGAAATCCATCATACAGGACGCAGCAAACCAGACACTGAA     300
 P  Y  P  V  G  E  Q  E  I  H  H  T  G  R  S  K  P  D  T  E    (100)

GGAAATGCTGTGAGCCTTGTTCCCCCAGACCTGACTGAAAATCCAGCAGGACTGAGGGGT     360
 G  N  A  V  S  L  V  P  P  D  L  T  E  N  P  A  G  L  R  G    (120)

GCAGTTGAAGAGCCGGCTGCCCCATGGGTAGGGGATAGTCCTATTGGGCAATCTGAGCTG     420
 A  V  E  E  P  A  A  P  W  V  G  D  S  P  I  G  Q  S  E  L    (140)

CTGGGAGATGATGACGCTTATCTCGGCAATCAAAGATCCAAGGAGTCTCTAGGTGAGGCC     480
 L  G  D  D  D  A  Y  L  G  N  Q  R  S  K  E  S  L  G  E  A    (160)

GGGATTCAGAAAGGCTCAGCCATGGCTGCCACTACTACCACCGCCATTTTCACAACCCTG     540
 G  I  Q  K  G  S  A  M  A  A  T  T  T  T  A  I  F  T  T  L    (180)

AACGAACCCAAACCAGAGACCCAAAGGAGGGGCTGGGCCAAGTCCAGGCAGCGTCGCCAA     600
 N  E  P  K  P  E  T  Q  R  P  G  W  A  K  S  R  Q  R  R  Q    (200)

GTGTGGAAGACGCGGGCGGAAGATGGCAGGGAGACTCCGGTATCTCTTCACATTTCCAA     660
 V  W  K  R  R  A  E  D  G  Q  G  D  S  G  I  S  S  H  F  Q    (220)

CCTTGGCCCAAGCATTCCCTTAAACACAGGGTCAAAAAGAGTCCACCGGAGGAAAGCAAC     720
 P  W  P  K  H  S  L  K  H  R  V  K  K  S  P  P  E  E  S  N    (240)

CAAAATGGTGGAGAGGGCTCCTACCGAGAAGCAGAGACCTTTAACTCCCAAGTAGGACTG     780
 Q  N  G  G  E  G  S  Y  R  E  A  E  T  F  N  S  Q  V  G  L    (260)

CCCATCTTATACTTCTCTGGGAGGCGGGAGCGGCTGCTGCTGCGTCCAGAAGTGCTGGCT     840
 P  I  L  Y  F  S  G  K  R  E  R  L  L  L  R  P  E  V  L  A    (280)

GAGATTCCCCGGGAGGCGTTCACAGTGGAAGCCTGGGTTAAACCGGAGGGAGGACAGAAC     900
 E  I  P  R  E  A  F  T  V  E  A  W  V  K  P  E  G  G  Q  N    (300)

AACCCAGCCATCATCGCAGGTGTGTTTGATAACTGCTCCCACACTGTCAGTGACAAAGGC     960
 N  P  A  I  I  A  G  V  F  D  N  C  S  H  T  V  S  D  K  G    (320)

TGGGCCCTGGGCATCCGCTCAGGGAAGGACAAGGGAAAGCGGGATGCTCGCTTCTTCTTC    1020
 W  A  L  G  I  R  S  G  K  D  K  G  K  R  D  A  R  F  F  F    (340)
```

Figure 1 B

```
TCCCTCTGCACCGACCGCGTGAAGAAAGCCACCATCTTGATTAGCCACAGTCGCTACCAA    1080
 S  L  C  T  D  R  V  K  K  A  T  I  L  I  S  H  S  R  Y  Q    (360)

CCAGGCACATGGACCCATGTGGCAGCCACTTACGATGGACGGCACATGGCCCTGTATGTG    1140
 P  G  T  W  T  H  V  A  A  T  Y  D  G  R  H  M  A  L  Y  V    (380)

GATGGCACTCAGGTGGCTAGCAGTCTAGACCAGTCTGGTCCCCTGAACAGCCCCTTCATG    1200
 D  G  T  Q  V  A  S  S  L  D  Q  S  G  P  L  N  S  P  F  M    (400)

GCATCTTGCCGGTCCTTGCTCCTGGGGGGAGACAGCTCTGAGGATGGGCACTATTTCCGT    1260
 A  S  C  R  S  L  L  L  G  G  D  S  S  E  D  G  H  Y  F  R    (420)

GGACACCTGGGCACACTGGTTTTCTGGTCGACCGCCCTCCCACAAAGCCATTTCAGCAC    1320
 G  H  L  G  T  L  V  F  W  S  T  A  L  P  Q  S  H  F  Q  H    (440)

AGTTCTCAGCATTCAAGTGGGGAGGAGGAAGCGACTGACTTGGTCCTGACAGCCAGCTTT    1380
 S  S  Q  H  S  S  G  E  E  E  A  T  D  L  V  L  T  A  S  F    (460)

GAGCCTGTGAACACAGAGTGGGTTCCCTTTAGAGATGAGAAGTACCCACGACTTGAGGTT    1440
 E  P  V  N  T  E  W  V  P  F  R  D  E  K  Y  P  R  L  E  V    (480)

CTCCAGGGCTTTGAGCCAGAGCCTGAGATTCTGTCGCCTTTGCAGCCCCCACTCTGTGGG    1500
 L  Q  G  F  E  P  E  P  E  I  L  S  P  L  Q  P  P  L  C  G    (500)

CAAACAGTCTGTGACAATGTGGAATTGATCTCCCAGTACAATGGATACTGGCCCCTTCGG    1560
 Q  T  V  C  D  N  V  E  L  I  S  Q  Y  N  G  Y  W  P  L  R    (520)

GGAGAGAAGGTGATACGCTACCAGGTGGTGAACATCTGTGATGATGAGGGCCTAAACCCC    1620
 G  E  K  V  I  R  Y  Q  V  V  N  I  C  D  D  E  G  L  N  P    (540)

ATTGTGAGTGAGGAGCAGATTCGTCTGCAGCACGAGGCACTGAATGAGGCCTTCAGCCGC    1680
 I  V  S  E  E  Q  I  R  L  Q  H  E  A  L  N  E  A  F  S  R    (560)

TACAACATCAGCTGGCAGCTCAGCGTCCACCAGGTCCACAATTCCACCCTGCGACACCGG    1740
 Y  N  I  S  W  Q  L  S  V  H  Q  V  H  N  S  T  L  R  H  R    (580)

GTTGTGCTTGTGAACTGTGAGCCCAGCAAGATTGGCAATCACCATTGTGACCCCGAGTGT    1800
 V  V  L  V  N  C  E  P  S  K  I  G  N  H  H  C  D  P  E  C    (600)

GAGCACCCACTCACAGGCTATGATGGGGTGACTGCCGCCTGCAGGGCCGCTGCTACTCC    1860
 E  H  P  L  T  G  Y  D  G  V  T  A  A  C  R  A  A  A  T  P    (620)

TGGAACCGCAGGGATGGGCTCTGTCACGTGGAGTGTAACAACATGCTGAACGACTTTGAC    1920
 W  N  R  R  D  G  L  C  H  V  E  C  N  N  M  L  N  D  F  D    (640)

GACGGAGACTGCTGCGACCCCCAGGTGGCTGATGTGGCAAGACCTGCTTTGACCCTGAC    1980
 D  G  D  C  C  D  P  Q  V  A  D  V  A  R  P  A  F  D  P  D    (660)

TCACCCAAGAGGGCATACATGAGTGTGAAGGAGCTGAAGGAGGCCCTGCAGCTGAACAGT    2040
 S  P  K  R  A  Y  M  S  V  K  E  L  K  E  A  L  Q  L  N  S    (680)
```

Figure 1 C

```
ACTCACTTCCTCAACATCTACTTTGCCAGCTCAGTGCGGGAAGACCTTGCAGGTGCTGCC      2100
 T  H  F  L  N  I  Y  F  A  S  S  V  R  E  D  L  A  G  A  A     (700)

ACCTGGCCTTGGGACAAGGACGCTGTCACTCACCTGGGTGGCATTGTCCTCAGCCCAGCA      2160
 T  W  P  W  D  K  D  A  V  T  H  L  G  G  I  V  L  S  P  A     (720)

TATTATGGGATGCCTGGCCACACCGACACCATGATCCATGAAGTGGGACATGTTCTGGGA      2220
 Y  Y  G  M  P  G  H  T  D  T  M  I  H  E  V  G  H  V  L  G     (740)

CTCTACCATGTCTTTAAGGGAGTCAGTGAAAGAGAATCCTGCAATGACCCCTGCAAGGAG      2280
 L  Y  H  V  F  K  G  V  S  E  R  E  S  C  N  D  P  C  K  E     (760)

ACAGTGCCATCCATGGAAACGGGAGACCTCTGTGCCGACACCGCCCCCACTCCCAAGAGT      2340
 T  V  P  S  M  E  T  G  D  L  C  A  D  T  A  P  P  K  S        (780)

GAGCTGTGCCGGGAACCAGAGCCCACTAGTGACACCTGTGGCTTCACTCGCTTCCCAGGG      2400
 E  L  C  R  E  P  E  P  T  S  D  T  C  G  F  T  R  F  P  G     (800)

GCTCCGTTCACCAACTACATGAGCTACACGGATGATAACTGCACTGACAACTTCACTCCT      2460
 A  P  F  T  N  Y  M  S  Y  T  D  D  N  C  T  D  N  F  T  P     (820)

AACCAAGTGGCCCGAATGCATTGCTATTTGGACCTAGTCTATCAGCAGTGGACTGAAAGC      2520
 N  Q  V  A  R  M  H  C  Y  L  D  L  V  Y  Q  Q  W  T  E  S     (840)

AGAAAGCCCACCCCCATCCCCATTCCACCTATGGTCATCGGACAGACCAACAAGTCCCTC      2580
 R  K  P  T  P  I  P  I  P  P  M  V  I  G  Q  T  N  K  S  L     (860)

ACTATCCACTGGCTGCCTCCTATTAGTGGAGTTGTATATGACAGGGCCTCAGGCAGCTTG      2640
 T  I  H  W  L  P  P  I  S  G  V  V  Y  D  R  A  S  G  S  L     (880)

TGTGGCGCTTGCACTGAAGATGGGACCTTTCGTCAGTATGTGCACACAGCTTCCTCCCGG      2700
 C  G  A  C  T  E  D  G  T  F  R  Q  Y  V  H  T  A  S  S  R     (900)

CGGGTGTGTGACTCCTCAGGTTATTGGACCCCAGAGGCAGGCTGTGGGCCTCCTGATGTG      2760
 R  V  C  D  S  S  G  Y  W  T  P  E  A  V  G  P  P  D  V        (920)

GATCAGCCCTGCGAGCCAAGCTTACAGGCCTGGAGCCCTGAGGTCCACCTGTACCACATG      2820
 D  Q  P  C  E  P  S  L  Q  A  W  S  P  E  V  H  L  Y  H  M     (940)

AACATGACGGTCCCCTGCCCCACAGAAGGCTGTAGCTTGGAGCTGCTCTTCCAACACCCG      2880
 N  M  T  V  P  C  P  T  E  G  C  S  L  E  L  L  F  Q  H  P     (960)

GTCCAAGCCGACACCCTCACCCTGTGGGTCACTTCCTTCTTCATGGAGTCCTCGCAGGTC      2940
 V  Q  A  D  T  L  T  L  W  V  T  S  F  F  M  E  S  S  Q  V     (980)

CTCTTTGACACAGAGATCTTGCTGGAAAACAAGGAGTCAGTGCACCTGGGCCCCTTAGAC      3000
 L  F  D  T  E  I  L  L  E  N  K  E  S  V  H  L  G  P  L  D    (1000)

ACTTCCTGTGACATCCCACTCACCATCAAACTGCACGTGGATGGGAAGGTGTCGGGGGTG      3060
 T  F  C  D  I  P  L  T  I  K  L  H  V  D  G  K  V  S  G  V    (1020)
```

Figure 1 D

```
AAAGTCTACACCTTTGATGAGAGGATAGAGATTGATGCAGCACTCCTGACTTCTCAGCCC      3120
 K  V  Y  T  F  D  E  R  I  E  I  D  A  A  L  L  T  S  Q  P      (1040)

CACAGTCCTTGTGCTCTGGCTGCAGGCCTGTGAGGTACCAGGTTCTCCGCGATCCCCCA      3180
 H  S  P  L  C  S  G  C  R  P  V  R  Y  Q  V  L  R  D  P  P      (1060)

TTTGCCAGTGGTTTGCCCGTGGTGGTGACACATTCTCACAGGAAGTTCACGGACGTGGAG    3240
 F  A  S  G  L  P  V  V  V  T  H  S  H  R  K  F  T  D  V  E      (1080)

GTCACACCTGGACAGATGTATCAGTACCAAGTTCTAGCTCAAGCTGGAGGAGAACTGGGA    3300
 V  T  P  G  Q  M  Y  Q  Y  Q  V  L  A  E  A  G  G  E  L  G      (1100)

GAACTTCGCCTCCTCTGAACCACATTCATGGAGCTCCTTATGTGGAGATGGGAAGGTG      3360
 E  A  S  P  P  L  N  H  I  H  G  A  P  Y  C  G  D  G  K  V      (1120)

TCAGAGAGACTGGGAGAAGAGTGTGATGATGGAGACCTTGTGAGCGGAGATGGCTGCTCC    3420
 S  E  R  L  G  E  E  C  D  D  G  D  L  V  S  G  D  G  C  S      (1140)

AAGTGTGTGAGCTGGAGGAAGGTTTCAACTGTGTAGGAGAGCCAAGCCTTTGCTACATG     3480
 K  V  C  E  L  E  E  G  F  N  C  V  G  E  P  S  L  C  Y  M      (1160)

TATGAGGGAGATGGCATATGTGAACCTTTTGAGAGAAAAACCAGCATTGTAGACTGTGGC    3540
 Y  E  G  D  G  I  C  E  P  F  E  R  K  T  S  I  V  D  C  G      (1180)

ATCTACACTCCCAAAGGATACTTGGATCAATGGGCTACCCGGGCTTACTCCTCTCGTGAA    3600
 I  Y  T  P  K  G  Y  L  D  Q  W  A  T  R  A  Y  S  S  R  E      (1200)

GACAAGAAGAAGTGTCCTGTTTCCTTGGTAACTGGAGAACCTCATTCCCTAATTTGCACA    3660
 D  K  K  K  C  P  V  S  L  V  T  G  E  P  H  S  L  I  C  T      (1220)

TCATACCATCCAGATTTACCCAACCACCGTCCCCTAACTGGCTGGTTTCCTGTGTTGCC    3720
 S  Y  H  P  D  L  P  N  H  R  P  L  T  G  W  F  P  C  V  A      (1240)

AGTGAAAATGAAACTCAGGATGACAGGAGTGAACAGCCAGAAGGTAGCCTGAAGAAAGAG    3780
 S  E  N  E  T  Q  D  D  R  S  E  Q  P  E  G  S  L  K  K  E      (1260)

GATGAGGTTTGGCTCAAAGTGTGTTTCAATAGACCAGGAGAGGCCAGAGCAATTTTTATT    3840
 D  E  V  W  L  K  V  C  F  N  R  P  G  E  A  R  A  I  F  I      (1280)

TTTTTGACAACTGATGGCCTAGTTCCCGGAGAGCATCACCAGCCGACAGTGACTCTCTAC    3900
 F  L  T  T  D  G  L  V  P  G  E  H  Q  P  T  V  T  L  Y      (1300)

CTGACCGATGTCCGTGGAAGCAACCACTCTCTTGGAACCTATGGACTGTCATGCCAGCAT    3960
 L  T  D  V  R  G  S  N  H  S  L  G  T  Y  G  L  S  C  Q  H      (1320)

AATCCACTGATTATCAATGTGACCCATCACCAGAATGTCCTTTTCCACCATACCACCTCA    4020
 N  P  L  I  I  N  V  T  H  H  Q  N  V  L  F  H  T  T  S      (1340)
```

Figure 1 E

```
GTGCTGCTGAATTCTCATCCCCACGGGTGGCATCTCAGCTGTGGCTCTAAGGACATCC        4080
 V  L  L  N  F  S  S  P  R  V  G  I  S  A  V  A  L  R  T  S     (1360)

TCCCGCATGGTCTTTCGCCTCCCAGTAACTGCATCTCAGAGGACGAGGGCAGAATCAT        4140
 S  R  I  G  L  S  A  P  S  N  C  I  S  E  D  E  G  Q  N  H     (1380)

CAGGGACAGAGCTGTATCCATCGGCCCTGTGGGAAGCAGGACAGCTGTCCGTCATTGCTG     4200
 Q  G  Q  S  C  I  H  R  P  C  G  K  Q  D  S  C  P  S  L  L     (1400)

CTTGATCATGCTGATGTGGTCAACTGTACCTCTATAGGCCCAGGTCTCATGAAGTGTGCT     4260
 L  D  H  A  D  V  V  N  C  T  S  I  G  P  G  L  M  K  C  A     (1420)

ATCACTTGTCAAAGGGGATTTGCCCTTCAGGCCAGCAGTGGGCAGTACATCACGCCCATG     4320
 I  T  C  Q  R  G  F  A  L  Q  A  S  S  G  Q  Y  I  R  P  M     (1440)

CAGAAGGAAATTCTGCTCACATGTTCTTCTGGGCACTGGGACCAGAATGTGAGCTGCCTT     4380
 Q  K  E  I  L  L  T  C  S  S  G  H  W  D  Q  N  V  S  C  L     (1460)

CCCGTGGACTGCGGTGTTCCCGACCCGTCTTTGGTGAACTATGCAAACTTCTCCTGCTCA     4440
 P  V  D  C  G  V  P  D  P  S  L  V  N  Y  A  N  F  S  C  S     (1480)

GAGGGAACCAAATTCTGAAACGCTGCTCAATCTCTTGTGTCCCACCAGCCAAGCTGCAA     4500
 E  G  T  K  F  L  K  R  C  S  I  S  C  V  P  P  A  K  L  Q     (1500)

GGACTGAGCCCATGGCTGACATGTCTTGAAGATGGTCTCTGGTCTCTCCCTGAAGTCTAC     4560
 G  L  S  P  W  L  T  C  L  E  D  G  L  W  S  L  P  E  V  Y     (1520)

TGCAAGTTGGAGTGTGATGCTCCCCCTATTATTCTGAATGCCAACTTGCTCCTGCCTCAC     4620
 C  K  L  E  C  D  A  P  P  I  I  L  N  A  N  L  L  L  P  H     (1540)

TGCCTCCAGGACAACCACGACGTGGGCACCATCTGCAAATATGAATGCAAACCAGGGTAC     4680
 C  L  Q  D  N  H  D  V  G  T  I  C  K  Y  E  C  K  P  G  Y     (1560)

TATGTGGCAGAAAGTGCAGAGGGTAAAGTCAGGAACAAGCTCCTGAAGATACAATGCCTG     4740
 Y  V  A  E  S  A  E  G  K  V  R  N  K  L  L  K  I  Q  C  L     (1580)

GAAGGTGGAATCTGGGAGCAAGGCAGCTGCATTCCTGTGGTGTGTGAGCCACCCCCTCCT     4800
 E  G  G  I  W  E  Q  G  S  C  I  P  V  V  C  E  P  P  P  P     (1600)

CTCTTTGAAGGCATGTATGAATGTACCAATGGCTTCAGCCTGGACAGCCAGTGTGTGCTC     4860
 V  F  E  G  M  Y  E  C  T  N  G  F  S  L  D  S  Q  C  V  L     (1620)

AACTGTAACCAGGAACGTGAAAAGCTTCCCATCCTCTGCACTAAAGAGGGCCTGTGGACC     4920
 N  C  N  Q  E  R  E  K  L  P  I  L  C  T  K  E  G  L  W  T     (1640)

CAGGAGTTTAAGTTGTGTGAGAATCTGCAAGGAGAATGCCCACCACCCCCCTCAGAGCTG     4980
 Q  E  F  K  L  C  E  N  L  Q  G  E  C  P  P  P  P  S  E  L     (1660)

AATTCTGTGGAGTACAAATGTGAACAAGGATATGGATTGGTGCAGTGTGTTCCCCATTG      5040
 N  S  V  E  Y  K  C  E  Q  G  Y  G  L  G  A  V  C  S  P  L     (1680)
```

Figure 1 F

```
TGTGTAATCCCCCCAGTGACCCCGTGATGCTACCTGAGAATATCACTGCTGACACTCTG     5100
 C  V  I  P  P  S  D  P  V  M  L  P  E  N  I  T  A  D  T  L    (1700)

GAGCACTGGATGGAACCTGTCAAAGTCCAGAGCATTGTGTGCACTGGCCGGCGTCAATGG     5160
 E  H  W  M  E  P  V  K  V  Q  S  I  V  C  T  G  R  R  Q  W    (1720)

CACCCAGACCCCGTCTTAGTCCACTGCATCCAGTCATGTGAGCCCTTCCAAGCAGATGGT     5220
 H  P  D  P  V  L  V  H  C  I  Q  S  C  E  P  F  Q  A  D  G    (1740)

TGGTGTGACACTATCAACAACCGAGCCTACTGCCACTATGACGGGGGAGACTGCTGCTCT     5280
 W  C  D  T  I  N  N  R  A  Y  C  H  Y  D  G  G  D  C  C  S    (1760)

TCCACACTCTCCTCCAAGAAGGTCATTCCATTTGCTGCTGACTGTGACCTGGATGAGTGC     5340
 S  T  L  S  S  K  K  V  I  P  F  A  A  D  C  D  L  D  E  C    (1780)

ACCTGCCGGGACCCCAAGGCAGAAGAAAATCAGTAA                             5376
 T  C  R  D  P  K  A  E  E  N  Q  *                             (1791)
```

Figure 3A

```
PA    mrlwsvvlhlgllsaalgcglaERPRRARRDPRAGRPPRPAAGPATCATR    50
PA2   mmclkilrislailagwalcsaNSELGWTRKKSLVEREHLNQVLLEGERC    50

PA    GPRPPRLAAAAAAAGRAWEAVRVPRRRQQR------------------    80
PA2   WLGAKVRRPRASPQHHLFGVYPSRAGNYLRPYPVGEQEIHHTGRSKPDTE   100

PA    --------------------------------------------------
PA2   GNAVSLVPPDLTENPAGLRGAVEEPAAPWVGDSPIGQSELLGDDDAYLGN   150

PA    --------------------------------------------------
PA2   QRSKESLGEAGIQKGSAMAATTTTAIFTTLNEPKPETQRRGWAKSRQRRQ   200
                                                        ▼
                           N-terminal residue of mature PAPP-A2 (Glu-81)
PA    -------------------------------------------EAR     83
PA2   VWKRRAEDGQGDSGISSHFQPWPKHSLKHRVKKSPPEESNQNGGEGSYRE  250
                                              ▲
      N-terminal residue of mature PAPP-A2 (Ser-234)

PA    GATEEPSPPSRALYFSGRGEQLRVLRADL-ELPRDAFTLQVWLRAEGGQR  132
PA2   AETFNSQVGLPILYFSGRRERLLLRPEVLAEIPREAFTVEAWVKPEGGQN  300
              .   :.*   *****  .  *  * :* :    :: *****.
```

Figure 3B

```
PA   SPAVITGLYDKCSYISRDRGWVVGIHTISDQDNKDPRYFFSLKTDRARQV 182
PA2  NPAIIAGVFDNCSHTVSDKGWALGIRSGKDKGKRDARFFFSLCTDRVKKA 350
        ***.*:*::***.       *:**.:***   . *:.****.***.;;:

PA   TTINAHRSYLPGQWVYLAATYDGQEMKLYVNGAQVATSGEQVGGIFSPLT 232
PA2  TILISHSRYQPGTWTHVAATYDGRHMALYVDGTQVASSLDQSGPLNSPFM 400
     * *: : **  ** *  *****:  : ***:*:***:  ::**::**:

PA   QKCKVLMLGG--SALNHNYRGYIEHFSLMKVARTQREILSDMETHGAHTA 280
PA2  ASCRSLLLGGDSSEDGHYFRGHLGTLVFWSTALPQSHFQHSSQHSSGEEE 450
     .:*:.*:*** . : :::** : . :.::. :*  :.:  :    * :

PA   LPQLLQENWDNVKHAWSPMKDGSSPKVEFSNAHG--FLLDTSLEPPLCG 328
PA2  ATDLVLTASFEPVNTEWVPFRDEKYPRLEVLQGFEPEPEILSPLQPPLCG 500
      . *: :.: :.*: * . :.*   *::*. .     *:*. ::****

PA   QTLCDNTEVIASYNQLSSFRQPKVVRYRVVNLYEDDHKNPTVTREQVDFQ 378
PA2  QTVCDNVELISQYNGYWPLRGEKVIRYQVVNICDDEGLNPIVSEEQIRLQ 550
     **:***.*::*.**  .  *: :**:*:***: :*::**.*.*:*: :*

PA   HHQLAEAFKQYNISWELDVLEVSNSSLRRRLILAN CDISKIGDENCDPEC 428
PA2  HEALNEAFSRYNISWQLSVHQVHNSTLRHRVVLVN CEPSKIGNDHCDPEC 600
     *  *.*** ::****:*.:: :.**:**:*::*. *  ****::.****
                                        LNR1
```

Figure 3C

```
                       LNR2
PA   NHTLTGHDGSDQRHLRHEAFVKKQHNGVCDMDCNYERFNFDGGECDPEI  478
PA2  EHPLTGYDGGDQR-LQGRCYSWNRRDGLCHVECNNMLNDFDDGDCCDPQV  649
     :*.:***:*** *    **: :. :::.*: **   ..*:. *:***::.

PA   TNVTQTCFDPDSPHRAYLDVNELKNILKLDGSTHLNIFFAKSEEELAGV   528
PA2  ADVRKTCFDPDSPKRAYMSVKELKEALQLNSTHFLNIYFASSVREDLAGA   699
     :* : ********:***:.*:****:: :*:***:***:**.* *:***

PA   ATWPWDKEALMHLGGIVLNPSFYGMPGHTHTMIHEIGHSLGLYHVFRGIS  578
PA2  ATWPWDKDAVTHLGGIVLSPAYYGMPGHTDTMIHEVGHVLGLYHVFKGVS  749
     *******:*:.******.*::********* ****:**.******* *:*

PA   EIQSCSDPCMETEPSFETGDLCNDTNPAPKHKSCGDPGPGNDTCGFHSFF  628
PA2  ERESCNDPCKETVPSMETGDLCADTAPTPKSELCREPEPTSDTCGFTRFP  799
     * :**.***:**.**:******.**.*.**:. * ** *.******. *

PA   NTPYNNFMSYADDDCTDSFTPNQVARMHCYLDLVYQGWQPSRKPAPVALA  678
PA2  GAPFTNYMSYTDDNCTDNFTPNQVARMHCYLDLVYQQWTESRKPTPIPIP  849
     .:*:.*:***:**:***.****************** *. ****:*: :

PA   PQVLGHTTDSVTLEWFPPIDGHFFERELGSACHLCLEGRILVQYASNASS  728
PA2  PMVIGQTNKSLTIHWLPPISGVVYDRASGSLCGACTEDGTFRQYVHTASS  899
     * ::*  .:.:* :*:***..  :. *** *  *** :* : ** :***
```

Figure 3D

```
PA   PMPCSPSGHWSPREAEGHPDVEQPCKSSVRTWSPNSAVNPHTVPPACPEP  778
PA2  RRVCDSSGYWTPEEAVGPPDVDQPCEPSLQAWSPEVHLYHMNMTVPCP-T   948
      *  ****  *    ****:,::,:****:,  ,   :,  , ,*,

PA   QGCYLELEFLYPLVPESLTIWVTFVSTDWDSSGAVNDIKLLAVSGKNISL   828
PA2  EGCSLELLFQHPVQADTLTLWVT---SFFMESSQVLFDTEILLENKESVHL  996
     :* ****  *    ::*  *:***    ,:**  ,*:: ,::* :: :

PA   GPQNVFCDVPLTIRLMDVGEEVYGIQIYTLDEHLEIDAAMLTSTADTPLC   878
PA2  GPLDTFCDIPLTIKLH-VDGKVSGVKVYTFDERIEIDAALLTSQPHSPLC  1045
     ** :,****:****:*  ,***:, *::**:**:*****:***  ,,***

PA   LQCKPLKYKVVRDPPLQMDVASIL--HLNRKFVDMDLNLGSVYQYWVITIS  927
PA2  SGCRPVRYQVLRDPFASGLPVVVTHSHRKFTDVEVTPGQMYQYQVLAEA   1095
      ,*:*  *: ****    : **:   * ,*** ** :,  ,: *** *:: ,

PA   GTEESEPSPAVTYIHGSSYCGDGIIQKDQGEQCDDMNKINGDGCSLFCRQ   977
PA2  GGELGEASPPINHIHGAPYCGDGKVSERLGEECDDGDLVSGDGCSKVCEL  1145
     * *  *:** * :,**,  ****    : *** :*** * :**** ,*

PA   EVSENCIDEPSRCYFHDGDGVCEEFEQKTSIKDCGVYTPQGFLDQWASNA  1027
PA2  EEGFNCVGEPSLCYMYEGDGICEPFFERKTSIVDCGIYTPKGYLDQWATRA 1195
     * , **, ***  **  ,***,** * *:**** *** ***,* *****,:*
```

Figure 3E

```
PA    SVSHQDQQ--CPGWVIIGQPAASQVCRTKVIDLSEGISQHAWYPCTISYPY  1076
PA2   YSSHEDKKKCPVSLVTGEPHS-LICTSYHPDLPNHRPLTGWFPCVASENE   1244
       **:*:;; * *   ;;  ;;  .. :*     ** ..    *

PA    SQLAQTT--------------FWLRAYFSQPMVAAAVIVHLVTDGTYYGDKQ  1115
PA2   TQDDRSEQPEGSLKKEDEVWLKVCENRPGEARAIFLFTTDGLVPGEHQQ     1294
       *:                   .*:**   *  *  *:::;; *.****  *

PA    ETTISVQLLDTKDQSHDLGLHVLSCRNNPLIIPVVHDLSQPFYHSQAVRVS   1165
PA2   PTVTLYLTDVRGSNHSLGTYGLSCQHNPLIINVTHHQNVLFHHTTSVLLN   1344
       *:**   : *   **: *  ***::*****:*  *  **   :.

PA    FSSPLVAISGVALRSEDNFDPVTLSSCQ-RGETYSPAEQSCVHFACEKTD   1214
PA2   FSSPRVGISAVALRTSSRIGLSAPSNCISEDEGQNHQGQSCIHRPCGKQD   1394
       ****  . *.****:  :   . *.*  :.*    . *** *  * *:*

PA    CPELAVENASLNCSSSDRYHGAQCTVSCRTGYVLQIRRDDELIKSQTGP    1263
PA2   QCPSLLLDHADVVNCTSIGPGLMKCAITCQRGFALQASSGQYIRPMQK--   1442
       **.*   :.:  **:: .  .: :*  ** . **.  ..  *
             SCR1

PA    SVTVTCTEGKWNNKQVACEPVLCSTPDHHQVVAASFSCPEGTTFGSQCSFQ  1313
PA2   EILLTCSSGHWDQNVSCLPVDCGVPDPSLVNYANFSCSEGTKFLKRCSIS   1492
       .: :**: * *::: *:* **  . :  :  *** ** ** *   **: :
                        SCR2
```

Figure 3F

```
                                                                    SCR3
PA   CRHPAQLKGNNSLLTCMEDGLWSFPEALQLMCLAPPPVPNADLQTARCR 1363
PA2  CVPPAKLQGLSPWLTCLEDGLWSLPEVYCKLECDAPPIILNANLLLPHCL 1542
     *  *:*** **** **:*  *: : ::* : :**: ::  :  :  *  :

PA   ENKHKVGSFCKYKCKPGYHVPGSSR-KSKKRAFKTQCTQDGSWQEGACVP 1412
PA2  QDNHDVGTICKYECKPGYYVAESAEGKVRNKLLKIQCLEGGIWEQGSCIP 1592
      :.* **: ***:*****:*  *:. * :: : ***: .* *::*:* *

PA   VTCDPPPKFHGLYQCTNGFQFNSECRIKCEDSDASQGLGSNVIHCRKDG----QEREKLPILCTKEG 1462
PA2  VVCEPPPPVFEGMYECTNGFSLDSQCVLNCN---------QEREKLPILCTKEG 1637
     * *:*** .:: :*:****.::*:* ::*:           **********

SCR4                SCR5
PA   TWNGSFHVCQEMQGCCSVP-NELNSNIKLQCPDGYAIGSECATSCLDHNS 1511
PA2  LWTQEFKLQENLQECPPPSELNS-VEYKCEQGYGIGAVCSPLCVIPPS 1686
      *..* : *::: *  .     :***  *  ** :**  **  *: .:.*
                                                     LNR3
PA   ESTILPMNVTVRDIPHWLNPTRVERVVCTAGLKWYPHPALIHCVKGCEPF 1561
PA2  DPVMLPENITADTLEHWMEPVKVQSIVCTGRRQWHPDPVLVHCQSCEPF 1736
     :  :** *:* * :: *::*.::*.  **  :::* *.::  **  ****

PA   MGDNYCDAINNRAFCNYDGGDCCTSTVKTKKVTPFPMSCDLQGDCACRDP 1611
PA2  QADGWCDTINNRAYCHYDGGDCCSSTLSSKKVIPFAADCDLD-ECTCRDP 1785
         : ***:*****:*:******* ::*.. ***  :**** :*:****
```

Figure 3G

```
PA   QAQEHSRKDLRGYSHG 1627
PA2  KAEENQ---------- 1791
     :*:.*:.
```

Figure 7 A

```
ATGATGTGCT TAAAGATCCT AAGAATAAGC CTGGCGATTT TGGCTGGGTG GGCACTCTGT      60
TCTGCCAACT CTGAGCTGGG CTGGACACGC AAGAAATCCT TGGTTGACAG GGAACACCTG     120
AATCAGGTGC TGTTGGAGG AGAACGTTGT TGGCTGGGGG CCAAGGTTCG AAGACCCAGA      180
GCTTCTCCAC AGCATCACCT CTTTGGAGTC TACCCCAGCA GGGCTGGGAA CTACCTAAGG     240
CCCTACCCCG TGGGGAGCA AGAAATCCAT CATACAGGAC GCAGCAAACC AGACACTGAA      300
GGAAATGCTG TGAGCCTTGT TCCCCCAGAC CTGACTGAAA ATCCAGCAGG ACTGAGGGGT     360
GCAGTTGAAG AGCCGGCTGC CCCATGGGTA GGGGATAGTC CTATTGGGCA ATCTGAGCTG     420
CTGGGAGATG ATGACGCTTA TCTCGGCAAT CAAAGATCCA AGGAGTCTCT AGGTGAGGCC     480
GGGATTCAGA AAGGCTCAGC CATGGCTGCC ACTACTACCA CCGCCATTTT CACAAGCCTG     540
AACGAACCCA AACCAGAGAC CCAAAGGAGG GGCTGGGCCA AGTCCAGGCA CCGTCGCCAA     600
GTGTCGAAGA GGCGGCGGA AGATGGGCAG GGAGACTCCG GTATCTCTTC ACATTTCCAA      660
CCTTGGCCCA AGCATTCCCT TAAACACAGG GTCAAAAGA GTCCACCGGA GGAAAGCAAC      720
CAAAATGGTG GAGAGGGCTC CTACCGAGAA GCAGAGACCT TTAACTCCCA AGTAGGACTG     780
CCCATCTTAT ACTTCTCTGG GAGGCGGGAG CGGCTGCTGC TGCGTCCAGA AGTGCTGGCT     840
GAGATTCCCC GGGAGGCGTT CACAGTGGAA GCCTGGGTTA ACCGGAGGG AGGACAGAAC      900
AACCCAGCCA TCATCGCAGG TGTGTTTGAT AACTGCTCCC ACACTGTCAG TGACAAAGGC     960
TGGGCCCTGG GGATCCGCTC AGGGAAGGAC AAGGGAAAGC GGGATGCTCG CTTCTTCTTC    1020
TCCCTCTGCA CCGACCGCGT GAAGAAAGCC ACCATCTTCA TTAGCCACAG TCGCTACCAA    1080
CCAGGCACAT GGACCCATGT GGCAGCCACT TACGATGCAC GGCACATGGC CCTGTATGTG    1140
GATGGCACTC AGGTGCTAG CAGTCTAGAC CAGTCTGGTC CCCTGAACAG CCCCTTCATG     1200
GCATCTTGCC GCTCTTTGCT CCTGGGGGA GACAGCTCTG AGGATGGGCA CTATTTCCGT     1260
GGACACCTGG GCACACTGGT TTTCTGGTCG ACCGCCCTGC CACAAAGCCA TTTTCAGCAC    1320
AGTTCTCAGC ATTCAAGTGG GGAGGAGGAA GCTGAACGACT TGGTCCTGAC AGCGAGCTTT   1380
GAGCCTGTGA ACACAGAGTG GGTTCCCTTT AGAGATGAGA AGTACCCACG ACTTGAGGTT    1440
CTCCAGGGCT TTGAGCCAGA GCCTGAGATT CTGTCGCCTT TGCAGCCCCC ACTCTGTGGG    1500
CAAACAGTCT GTGACAATGT GGAATTGATC TCCCAGTACA ATGGATACTG GCCCCTTCGG    1560
GGAGAGAAGG TGATACGCTA CCAGGTGGTG AACATCTGTG ATGATGAGGG CCTAAACCCC    1620
ATTGTGAGTG AGGAGCAGAT TCGTCTGCAG CACGGAGGCCA TGAATGAGGC CTTCAGCCGC   1680
TACAACATCA GCTGGCAGCT GAGCGTCCAC CAGGTCCACA ATTCCACCCT GCGACACCGG    1740
CTTGTGCTTG TGAACTGTGA GCCCAGCAAG ATTGGCAATG ACCATTGTGA CCCCGAGTCT    1800
GAGCACCCAC TCACAGGCTA TGATGGGGGT GACTGCCGCC TGCAGGGCCC CTGCTACTCC    1860
TGGAACCGCA GGGATGGGCT CTGTCACGTG GAGTGTAACA ACATGCTGAA CGACTTTGAC    1920
GACGGAGACT GCTGCGACCC CCAGGTGGCT GATGTGCGCA AGACCTGCTT TGACCCTGAC    1980
TCACCCAAGA GGGCATACAT GAGTGTGAAG AGGCCCTGCA GCTGAACAGT ACTCACTTCC    2040
TCAACATCTA CTTTGCCAGC TCAGTGCGGG AAGACCTTGC AGGTGCTGCC                2100
ACCTGGCCTT GGGACAAGGA CGCTGTCACT CACCTGGCTG GCATTGTCCT CAGCCCAGCA    2160
TATTATGGGA TGCCTGGCCA CACCGACACC ATGATCCATG AAGTGGGACA TGTTCTGGGA    2220
CTCTACCATG TCTTTAAAGG AGTCAGTGAA AGAGAATCCT GCAATGACCC CTGCAAGCAG    2280
ACAGTGCCAT CCATGGAAAC GGGAGACCTC TGTGCCGACA CCGCCCCCAC TCCCAAGAGT    2340
GAGCTGTGCC GGGAACCAGA GCCCACTAGT GACACGTGTG GCTTCACTCG CTTCCCAGGG    2400
GCTCCGTTCA CCAACTACAT GAGCTACACG GATGATAACT GCACTGACAA CTTCACTCCT    2460
AACCAAGTGG CCCGAATGCA TTGCTATTTG GACCTAGTCT ATCAGACAGTG GACTGAAAGC    2520
AGAAAGCCCA CCCCCATCCC CATTCCACCT ATGGTCATCG GACAGACCAA CAAGTCCCTC    2580
ACTATCCACT GGCTGCCTCC TATTAGTGGA GTTGTATATG ACAGGGCCTC AGGCAGCTTG    2640
TGTGGCCCTT GCACTGAAGA TGCGACCTTT CGTCACTATG TGCACACACG TTCCTCCGG     2700
CGGGTGTGTC ACTCCTCAGG TTATTGGACC CCAGAGGAGG CTGTCGGGCC TCCTGATGTG    2760
GATCAGCCCT GCGAGCCAAG CTTACAGGCC TGGAGCCCTG AGGTCCACCT GTACCACATG    2820
AACATGACGG TCCCCTGCCC CACAGAAGGC TGTAGCTTGG AGCTGCTCTT CCAACACCCG    2880
GTCCAAGCCG ACACCCTCAC CCTGTGGGTC ACTTCCTTCT TCATGGAGTC CTCGCAGGTC    2940
CTCTTTGACA CAGAGATCTT GCTGGAAAAC AAGGAGTCAG TGCACCTGGG CCCCTTAGAC    3000
ACTTTCTGTG ACATCCCACT CACCATCAAA CTGCACCTGG ATGGGAAGGT GTCGGGGGTG    3060
AAAGTCTACA CCTTTGATGA GAGGATAGAG ATTGATGCAG CACTCCTGAC TTCTCAGCCC    3120
CACAGTCCCT TGTGCTCTGG CTGCAGGCCT CTGAGGTACC AGGTTCTCCG CGATCCCCCA    3180
TTTGCCAGTG GTTTGCCCGT GGTGGTGACA CATTCTCACA GGAAGTTCAC GGACGTGGAG    3240
```

Figure 7 B

```
GTCACACCTG GACAGATCTA TCAGTACCAA GTTCTAGCTG AAGCTGGAGG AGAACTGGGA    3300
GAAGCTTCGC CTCCTCTGAA CCACATTCAT GGAGCTCCTT ATTGTGGAGA TGGGAAGGTG    3360
TCAGAGAGAC TGGGAGAAGA GTGTGATGAT GGAGACCTTG TGAGCGGAGA TGGCTGCTCC    3420
AAGGTGTGTG AGCTGCACGA AGGTTTCAAC TGTGTAGGAG AGCCAAGCCT TTGCTACATG    3480
TATGAGGGAG ATGGCATATG TGAACCTTTT GAGAGAAAAA CCAGCATTGT AGACTGTGGC    3540
ATCTACACTC CCAAAGGATA CTTGGATCAA TGGGCTACCC GGGCTTACTC CTCTCATGAA    3600
GACAAGAAGA AGTGTCCTGT TTCCTTGGTA ACTGGAGAAC CTCATTCCCT AATTTGCACA    3660
TCATACCATC CAGATTTACC CAACCACCGT CCCCTAACTG GCTGGTTTCC CTGTGTTGCC    3720
AGTGAAAATG AAACTCACGA TGACAGGAGT GAACAGCCAG AAGGTAGCCT GAAGAAAGAG    3780
GATGAGGTTT GGCTCAAAGT GTGTTTCAAT AGACCAGGAG AGGCCAGAGC AATTTTTATT    3840
TTTTTGACAA CTGATGGCCT AGTTCCCGGA GAGCATCAGC AGCCGACAGT GACTCTCTAC    3900
CTGACCGATG TCCGTGGAAG CAACCACTCT CTTGGAACCT ATGGACTGTC ATGCCAGCAT    3960
AATCCACTGA TTATCAATGT GACCCATCAC CAGAATGTCC TTTTCCACCA TACCACCTCA    4020
GTGCTGCTGA ATTTCTCATC CCCACGGGTC GGCATCTCAG CTGTGGCTCT AAGGACATCC    4080
TCCCGCATTG GTCTTTCGGC TCCCAGTAAC TGCATCTCAG AGGACCAGGG GCAGAATCAT    4140
CAGGGACAGA GCTGTATCCA TCGGCCCTGT GGGAAGCAGG ACAGCTGTCC GTCATTGCTG    4200
CTTGATCATG CTGATGTGGT GAACTGTACC TCTATAGCGC CAGGTGTCAT GAAGTGTGCT    4260
ATCACTTGTC AAAGGGGATT TGCCCTTCAG GCCAGCAGTG GGCAGTACAT CAGGCCCATG    4320
CAGAAGGAAA TTCTGCTCAC ATGTTCTTCT GGGCACTGGG ACCAGAATGT GAGCTGCCTT    4380
CCCGTGGACT GCGGTGTTCC CGACCCGTCT TTGGTGAACT ATGCAAACTT CTCCTGCTCA    4440
GAGGGAACCA AATTTCTGAA ACGCTGCTCA ATCTCTTGTG TCCCACCAGC CAAGCTGCAA    4500
GCACTGAGCC CATGGCTGAC ATGTCTTGAA GATGGTCTCT GGTCTCTCCC TGAAGTCTAC    4560
TGCAAGTTGG AGTGTGATGC TCCCCCTATT ATTCTGAATG CCAACTTGCT CCTGCCTCAC    4620
TGCCTCCAGG ACAACCACGA CGTGGGCACC ATCTGCAAAT ATGAATGCAA ACCAGGGTAC    4680
TATGTGGCAG AAAGTGCAGA GGGTAAAGTC AGGAACAAGC TCCTGAAGAT ACAATGCCTG    4740
GAAGGTGGAA TCTGGGAGCA AGGCAGCTGC ATTCCTGTGG TGTGTGAGCC ACCCCCTCCT    4800
GTGTTTGAAG GCATGTATGA ATGTACCAAT GGCTTCAGCC TGGACAGCCA GTGTGTGCTC    4860
AACTGTAACC AGGAACGTGA AAAGCTTCCC ATCCTCTGCA CTAAAGAGGG CCTGTGGACC    4920
CAGGAGTTTA AGTTGTGTGA GAATCTGCAA GGAGAATGCC CACCACCCCC CTCAGAGCTG    4980
AATTCTGTGG AGTACAAATG TGAACAAGGA TATGAGTTGG GTGCAGTGTG TTCCCCATTG    5040
TGTGTAATCC CCCCCAGTGA CCCCGTGATG CTACCTGAGA ATATCACTGC TGACACTCTG    5100
CAGCACTGGA TGGAACCTGT CAAAGTCCAG AGCATTGTGT GCACTGGCCG GCGTCAATGG    5160
CACCCAGACC CCGTCTTAGT CCACTGCATC CAGTCATGTG AGCCCTTCCA AGCAGATGGT    5220
TGGTGTGACA CTATCAACAA CCGAGCCTAC TGCCACTATG ACGGGGAGA CTGCTGCTCT    5280
TCCACACTCT CCTCCAAGAA GGTCATTCCA TTTGCTGCTG ACTGTGACCT GGATGAGTGC    5340
ACCTGCCGGG ACCCCAAGGC AGAAGAAAAT CAGTAACTGT GGGAACAAGC CCCTCCCTCC    5400
ACTGCCTCAG AGGCAGTAAG AAGAGAGGC CGACCCAGGA GGAAACAAAG GGTGAATGAA    5460
GAAGAACAAT CATGAAATGG AAGAGGAGG AAGAGCATGA AGGATCTTAT AAGAAATGCA    5520
AGAGGATATT GATAGGTGTG AACTAGTTCA TCAAGTAGCC CAAGTAGGAG AGAATCATAG    5580
GCAAAAGTTT CTTTAAAGTG GCAGTTGATT AACATGGAAG GGGAAATATG ATAGATATAT    5640
AAGGACCCTC CTCCCTCACT TATATTCTAT TAAATCCTAT CCTCAACTCT TGCCCTGCTC    5700
TCCGCTCCAC CCCCTGCCAA CTACTCAGTC CCACCCAACT TGTAAACCAA TACCAAAATA    5760
CTAGAGGAGA AGTTGGCAGG GATACTGTTA ATACCCATTT TGAATGGATT GCCATCTTTC    5820
AGAGCTTGTC TGCTCTCAAC TGGCTCTTTT TCTTTTTGTG TAGTTTCCCT TAAATAATGA    5880
AGTTAGTTAT TAATTCTTTA TAAGTATTTA AACATAATTA TATAAATATA TTATATATAT    5940
TATATTTTTT GCTGTTTACT AAGCTAAAAA TTATTCATTG TTCCACACAT GCTGCTGTGA    6000
AGTTCACATT CAAGATGAAT GTTGAGACTT TGAGGACAGA AAGGCAACTT ATTTCCCAT    6060
CTTTCTATGG ATGCGGATTG GCAGGTTGAA TGGGAAGTAC AGAAGGAGAG AGAGTAATTA    6120
GATGGAATTC TGGATGCTAG CATGTAAAGC TAATCATCTT TTTTTTTATG ACCTGGGAGC    6180
TGGGCCCATT TTATGACCAA GGAGATGGGA AGTTGGAATG GTGGTAGTAA GAGGCATAGG    6240
AAGTTGAGTG TGAATACCAT TGGTGATGGG TCCAGGAGAA CTAGACTATG GTTCTTGAAT    6300
ATCTGTCCAC AAAGAATATA CTAACTTTTG TCAACTTCTC AGAACTCCCA ACTGGAGTCG    6360
GTGAGACCTA GGATTTTCTG CACTTCCACA CATGCCTGTT CCAAGTGTGG CTGTCAGCCA    6420
GTCAACAAGT TTGTACTATG GCCCATTCTC TGATCACCAG GATTACAGGA ACTCACACAC    6480
TCCTCATACT TGGCCTGTAG TCCTACTTCT TGTTAGAAGT CTCCAAGTCT GGCCAGTCAC    6540
```

Figure 7 C

```
ATGACCAAGT GTTGATTTTT CTGGAGGAAA AATTTTATGG AAATGATATA GGGGAAAGGT   6600
GGGAGGAGAT GAAAGAACAG GCAAGAGCTG TCAGGGTTAA ATCCAGGCCC GGGCATGAGA   6660
ATGGAAGTGA TCGGGAGAC TCGGTCCTTG TTCCAAGTCT CCAAAGAAGA CCAAAGTGGG    6720
TCCCTTGACC AATGAAGAAT CTGAGATAAA TTCTCTTCAA GTATCATGTA CAAAATCTGT   6780
GAGCCAGAGA TTTTGACTTG AGCAAGCCAT GGAAATGCAT GGAGCAAGGG TGACACTCTG   6840
TGGGAGACA GAAGAATTTC AACTATTTAA TGTCCATTTT GTTGTTTTA CCCTTCTTA     6900
TCCAATAGAT GGAATGCACA TGAAATGACC ATATTAAGCC TCTCTCTATT TACATCCCAG   6960
GCTCACTGGG ATGTGATCTA CTGCAGTTAC ATTTTCTTCT AACCGTTTCT GGATTAGACC   7020
CTAGGGAAAG TGAGTAAGGA GCCAGTTTCT GTTTAACATT CTAGTTTTAC TCATTTTAGG   7080
AAGCCTGTGA GTGAGGCTTG TCTCCTTTAA AGTTTCTTCT CCAATGGAAA CCAAGAACAG   7140
ACAAAATTTA GAGCTCAGCT GTGGTCTCTT CTCATCTTCT GCTCTTTGC TTTGACCACA    7200
GTTTTTCTAC TCTTCCCATC AACACTAGAG CAATGGCTGT GCAAATAGGA ATAGGAAATA   7260
CTACCACAAT GATAGAAATA TTATCCACAC TATCACGTAC GGAAGAACAA TATCCTGAAA   7320
GAGAATAAAA CACGAATAAG GTGATGTACC CACATTAATC TGTGGGTTTG TGGAATGAGG   7380
GTTGCAAAGT TATTGGGAAA AGGAAAGAGC AGAGTTCACC CATTCAAAAA AAACCTTTTG   7440
TCTACTAATC TCTAGTGTAA AGAAAATGTA GTTCAGATAC CATTCATTGT CTTGGGTCAT   7500
GCTTAGTGCC CCCAAGAAGA CAAACATATT TATTCTTGGG ATTCTGATAC CCTTCAATAT   7560
GCAAAGGACA ATGGAAAAGT TTAGCACACTC TATTTTCAAA ATTTTATAAA CTTGTTTTAT   7620
TGGGAAAAT GTCCAAATTG CTAGACACAT TCTAAGTTCT GCCTTGGAGA ATCCTACTTT    7680
GTCTGAGATT GAGGCAGAGG AATTGTTATC CTGGGCATTA CTCAGCTCAG GAACATGGAG   7740
CCTGTGGTTC ATGCCAGTGT GTGTCTTCAT GCAGTCTCTC CACAAGAGCA ACAGTAAGAA   7800
CATTCTGTT TTAAATTTCA TTTTAAAATA TTTTATTATC TGCAATTCAC CACTCCTCTG    7860
GGAAAGCAAA AGGAAAGTTC CTGTTGTGTG TGAAGAGCCT CTTAGGCTAT AAGGCTTCCC   7920
AGCCATAGTC AGCTATAGCT ATTCAGAGAC AGCACGTTCT TCCAGTCTTT GTTCCTGGGA   7980
CCTGATGTTT TGAGCAACTC AGGTCACTGA TAAAGTGAA GGACTAAGAC ACTGTGGTCA    8040
CAGATCCCAG CAACATCAAC TCATACTCAA TCCATGTGGT GGTCCACATT CTGCTACTCT   8100
TATCCACCCA TGTGGTCATT GAGAGCCTTT CTCAGACACT CTTCTGTGTG TTTGATTGTG   8160
CCCAGGTGCC CCAGGGCTAG CTGGCTCTAA CAACTAGCAT GACAGCCTCC AATCAGAAAG   8220
GCAGGTAAGG GGACAGGGTG AGGAGAATGG GCAGATACTC ACAGAAATTA AAGTAAAGGG   8280
ATTGTGAAAG TAAGAGCTC TTCCTGATCC TCATCTTCTC TTTTTCTAT TACAAGGCAT     8340
TGAACTTGGC ACTTCCTGTA TTCTTTGTGA TCACTATTGA GTCCATTAGT TAACACCCAA   8400
GGGGATGGCT TGATTGGCAA TGTAGTGAAA GCAGCTCATC TACTGTATTG TAATCTAAAA   8460
CAGCTACAGC CAGTTATTTT GTAAGATTAT AAGTTGTTCA TTAAAAAATC AGCACACAAA   8520
ATATGAA                                                              8527
```

PREGNANCY-ASSOCIATED PLASMA PROTEIN-A2 (PAPP-A2) POLYNUCLEOTIDES

FIELD OF THE INVENTION

The present invention relates to a novel polypeptide with homology to pregnancy-associated plasma protein-A (PAPP-A). The novel polypeptide according to the invention is denoted PAPP-A2. The invention further relates to novel polynucleotides comprising a nucleic acid sequence encoding such a polypeptide, or a fragment thereof.

The invention further relates to methods for using the novel polynucleotides, including fragments thereof as defined herein below, and methods for using the novel polypeptides capable of being produced from such polynucleotides.

The invention also relates to expression and purification of recombinant PAPP-A2, and to production of polyclonal and monoclonal antibodies against PAPP-A2, and to the purification of native PAPP-A2 from human tissues or body fluids.

In further aspects the invention relates to uses of PAPP-A2 as a marker for pathological states, and as a therapeutic target for drugs that modify the proteolytic activity of PAPP-A2 in pregnant as well as non-pregnant individuals.

BACKGROUND OF THE INVENTION

Pregnancy-Associated Plasma Protein-A (PAPP-A)

PAPP-A was first isolated in 1974 from pregnancy serum along with other proteins believed to be of placental origin (Lin et al., 1974, Am J Obstet Gynecol 118, 223-36). The concentration in serum reaches about 50 mg/liter at the end of pregnancy (Folkersen et al., 1981, Am J Obstet Gynecol 139, 910-4; Oxvig et al., 1995, J Biol Chem 270, 13645-51). PAPP-A was originally characterized as a high molecular weight homotetramer (Bischof, 1979, Arch Gynecol 227, 315-26; Lin et al., 1974, Am J Obstet Gynecol 118, 223-36; Sinosich, 1990, Electrophoresis 11, 70-8), but it has now been demonstrated that PAPP-A primarily exists in pregnancy serum and plasma as a covalent, heterotetrameric 2:2 complex with the proform of eosinophil major basic protein (proMBP), PAPP-A/proMBP (Oxvig et al., 1993, J Biol Chem 268, 12243-6). Only about 1% of PAPP-A in pregnancy serum and plasma is present as a homodimer, as recently demonstrated (Overgaard et al., 2000, J Biol Chem). The existence of the PAPP-A/proMBP complex was revealed, in part, by the isolation of a PAPP-A and a proMBP peptide, linked together by a disulfide bond, from a digest of purified PAPP-A/proMBP (Oxvig et al., 1993, J Biol Chem 268, 12243-6).

The subunits of the PAPP-A/proMBP complex can be irreversibly separated by reduction of disulfide bonds and denaturation (Oxvig et al., 1993, J Biol Chem 268, 12243-6). In reducing SDS-PAGE, the PAPP-A subunit has an apparent molecular weight of 200 kDa (Oxvig et al., 1994, Biochim Biophys Acta 1201, 415-23), and its 1547-residue sequence is known from cloned cDNA (Kristensen et al., 1994, Biochemistry 33, 1592-8). PAPP-A is synthesized as a pre-pro-protein (preproPAPP-A), including a 80-residue pre-pro-piece (Haaning et al., 1996, Eur J Biochem 237, 159-63). No proteins with global homology to PAPP-A has been reported in the literature, but PAPP-A contains sequence motifs, including an elongated zinc binding motif (HEXXHXXGXXH) (SEQ ID NO:26) at position 482-492 (numbering according to Kristensen et al., 1994, Biochemistry 33, 1592-8). This motif and a structurally important methionine residue, also thought to reside in PAPP-A at position 556, are strictly conserved within the metzincins, a superfamily of zinc peptidases: astacins, adamalysins (or reprolysins), serralysins and matrixins (matrix metalloproteinases or MMP's) (Bode et al., 1993, FEBS Lett 331, 134-40; Stocker et al., 1995, Protein Sci 4, 823-40).

The proMBP subunit has a calculated peptide mass of 23 kDa (Barker et al., 1988, J Exp Med 168, 1493-8; McGrogan et al., 1988, J Exp Med 168, 2295-308). In SDS-PAGE, however, proMBP migrates as a smear of 50-90 kDa that is not visible in Coomassie-stained gels (Oxvig et al., 1993, J Biol Chem 268, 12243-6), probably due to its strong and unusual glycosylation (Oxvig et al., 1994, Biochem Mol Biol Int 33, 329-36; Oxvig et al., 1994, Biochim Biophys Acta 1201, 415-23). PAPP-A and proMBP are both produced in the placenta during pregnancy, but mainly in different cell types as shown by in situ hybridization (Bonno et al., 1994, Lab Invest 71, 560-6). Analyses by RT-PCR revealed that both PAPP-A and proMBP mRNA are present in several reproductive and nonreproductive tissues, although the levels are lower than in the placenta (Overgaard et al., 1999, Biol Reprod 61, 1083-9).

Clinical Use of PAPP-A

Clinically, depressed serum levels of PAPP-A are increasingly being used as a predictor of Down's syndrome pregnancies (Brambati et al., 1993, Br J Obstet Gynaecol 100, 324-6; Haddow et al., 1998, N Engl J Med 338, 955-61; Wald et al., 1992, Bmj 305, 28; Wald et al., 1999, N Engl J Med 341, 461-7), and it has been shown that PAPP-A serum levels are also depressed in other fetal abnormalities (Biagiotti et al., 1998, Prenat Diagn 18, 907-13; Spencer et al., 2000, Prenat Diagn 20, 411-6; Westergaard et al., 1983, Prenat Diagn 3, 225-32).

Further, the synthesis of PAPP-A in smooth muscle cells of the coronary artery following angioplasty is increased (Bayes-Genis et al., 2000, Arterioscler Thromb Vasc Biol, in press), which is currently being evaluated for potential clinical value. Data show that measurements of proMBP in pregnancy serum also have a diagnostic value (Christiansen et al., 1999, Prenat Diagn 19, 905-10).

Proteolytic Activity of PAPP-A: Cleavage of IGFBP-4

Only recently, the putative metalloproteinase activity of PAPP-A has been experimentally confirmed (Lawrence et al., 1999, Proc Natl Acad Sci USA 96, 3149-53). PAPP-A was partially purified from human fibroblast-conditioned medium (HFCM) and shown to be responsible for the proteolytic activity of HFCM against insulin-like growth factor binding protein (IGFBP)-4. IGFBP's, of which six have been described, are important modulators of IGF-I and -II activity (Fowlkes, 1997, Trends Endocrinol Metab 8, 299-306; Rajaram et al., 1997, Endocr Rev 18, 801-31).

IGF-I and -II are essential polypeptides with potent anabolic and mitogenic actions both in vivo and in vitro. IGF bound to IGFBP-4 cannot interact with its receptor, but bioactive IGF is released once the binding protein is cleaved. Interestingly, cleavage of IGFBP-4 by PAPP-A strictly requires the presence of IGF (Conover et al., 1993, J Clin Invest 91, 1129-37; Lawrence et al., 1999, Proc Natl Acad Sci USA 96, 3149-53). PAPP-A secretion has also been demonstrated from osteoblasts and marrow stromal cells (Lawrence et al., 1999, Proc Natl Acad Sci USA 96, 3149-53), from granulosa cells (Conover et al., 1999, J Clin Endocrinol Metab 84, 4742-5), and from vascular smooth muscle cells (Bayes-Genis et al., 2000, Arterioscler Thromb Vasc Biol, in press), all of which have known IGF-dependent IGFBP-4 proteinase activity.

IGFBP-5

Like IGFBP-4, IGFBP-5 cleavage has been widely reported to occur by unidentified proteinases is a number of tissues and conditioned media (Hwa et al., 1999, *Endocr Rev* 20, 761-87).

SUMMARY OF THE INVENTION

Pregnancy-Associated Plasma Protein-A2

The novel nucleic acid according to the invention has been isolated from human placenta and characterised by means of sequencing analysis. The novel nucleotide sequence encodes a new polypeptide, PAPP-A2.

The amino acid sequence of PAPP-A2 is composed of a 233-residue pre-pro-piece and a 1558-residue mature portion. The mature portion of PAPP-A2 is homologous with the mature portion of PAPP-A (approx. 45% identity), but the prepro-pieces do not show any similarity between the two proteins. Like PAPP-A, PAPP-A2 contains conserved amino acid stretches that classify it as a putative metalloproteinase of the metzincin superfamily.

PAPP-A2 has been expressed in a mammalian expression system, and it has been demonstrated that PAPP-A2 is an active enzyme. Further, it has been shown that PAPP-A2 cleaves IGFBP-5, Insulin Like Growth Factor Binding Protein 5. In comparison, the cleavage of IGFBP-4 by PAPP-A has previously been demonstrated.

A complementary DNA (cDNA) which encodes the full length form of PAPP-A2 is identified, sequenced and isolated. The cDNA or portions of the cDNA is cloned into expression vectors for expression in a recombinant host. The cDNA is useful to produce recombinant full-length PAPP-A2 or fragments of PAPP-A2. The cDNA and the recombinant PAPP-A2 protein derived therefrom are useful in the production of antibodies, diagnostic kits, laboratory reagents and assays.

The cDNA and the recombinant PAPP-A2 protein may also be used to identify compounds that affect PAPP-A2 function. PAPP-A2 antisense oligonucleotides or antisense mimetics may be clinically useful for reducing the expression of PAPP-A2 protein and thereby antagonizing the effects of PAPP-A. Similarly, the PAPP-A2 coding sequence can be used for gene therapy to introduce PAPP-A2 into target cells thereby enhancing the effects of PAPP-A2.

The invention furthermore pertains to PAPP-A2 for use as a therapeutic target for the reduction or elimination of IGFBP-5 proteolytic activity in a cell.

It is furthermore an objective of the present invention to provide methods for use of PAPP-A2 for diagnostic purposes.

Other features and advantages of the invention will be apparent from the following drawings and description hereof, from the following detailed description, and from the claims.

DEFINITIONS

As used herein, PAPP-A2 refers to an isolated PAPP-A2 polypeptide having the amino acid sequence listed in FIG. 1 (SEQ ID NO:2), or a variant thereof as defined herein. The PAPP-A2 according to the invention, or a variant thereof, may be produced by recombinant DNA technology, or the PAPP-A2 may be naturally occurring.

A PAPP-A2 encoding nucleotide sequence refers to an isolated nucleic acid having the sequence listed in FIG. 1 (SEQ ID NO:1), or a variant thereof as defined herein.

"Active" refers to those forms of PAPP-A2 which retain the biological and/or immunological activities of any naturally occurring PAPP-A2.

"Naturally occurring PAPP-A2" refers to PAPP-A2 produced by human cells that have not been genetically engineered and specifically contemplates various PAPP-A2s arising from post-translational modifications of the polypeptide including but not limited to acetylation, carboxylation, glycosylation, phosphorylation, lipidation, acylation, or complex formation, covalent or noncovalent, with other polypeptides.

An "isolated polypeptide" is a protein, or a variant or fragment thereof, which constitutes 90% or more of the protein contents of a given preparation as evaluated by standard methods known in the art of protein chemistry.

"Derivative" refers to polypeptides derived from naturally occurring PAPP-A2 by chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

"Recombinant variant" refers to any polypeptide differing from naturally occurring PAPP-A2 by amino acid insertions, deletions, and substitutions, created using recombinant DNA techniques. Guidance in determining which amino acid residues may be replaced, added or deleted without abolishing activities of interest, such as proteolytic activity or cell adhesion, may be found e.g. by comparing parts of the sequence of PAPP-A2 with structurally similar proteins (e.g. other metzincin family proteinases), with locally homologous proteins of known disulfide structure, or by secondary structure predictions.

Preferably, amino acid "substitutions" are the result of replacing one amino acid with another amino acid having similar structural and/or chemical properties, such as, but not limited to, the replacement of a leucine with an isoleucine or valine, replacement of an aspartate with a glutamate, or replacement with a threonine with a serine, i.e., conservative amino acid replacements. Further examples and definitions falling within the meaning of the term "substitutions" as applied herein are provided in the detailed description of the invention herein below.

Amino acid "insertions" or "deletions" are typically in the range of from about 1 amino acid to about 50 amino acids, such as from about 1 amino acid to about 20 amino acids, for example from about 1 amino acid to about 20 amino acids, such as from about 1 amino acid to about 10 amino acids. The variation allowed may be experimentally determined by systematically making insertions, deletions, or substitutions of amino acids in a PAPP-A2 molecule using recombinant DNA techniques and assaying the resulting recombinant variants for activity.

Where desired, a "signal or leader sequence" can direct the polypeptide (full length PAPP-A2, or portions of the PAPP-A2 polypeptide) through the membrane of a cell. Such a sequence may be naturally present on the polypeptides of the present invention or provided from heterologous protein sources by recombinant DNA techniques.

A polypeptide "fragment", "portion", or "segment" is a stretch of amino acid residues of at least about 5 amino acids, often at least about 7 amino acids, typically at least about 9 to 13 amino acids, such as at least about 17 or more amino acids in various embodiments. It may also be a longer stretch of residues up to intact PAPP-A2 in length. To be active, any PAPP-A2 polypeptide or PAPP-A2 polypeptide fragment must have sufficient length to display biologic and/or immunologic activity on their own, or when conjugated to a carrier protein such as keyhole limpet hemocyanin.

An "oligonucleotide" or polynucleotide "fragment", "portion", or "segment" is a stretch of the PAPP-A2 encoding sequence which is useful in the expression of PAPP-A2 polypeptide fragments. It may also be a stretch of nucleotide residues capable of being used in a polymerase chain reaction (PCR) or a hybridization procedure, typically for amplifying or revealing related parts of mRNA or DNA molecules. In particular, one or both oligonucleotide probes will comprise sequence that is identical or complementary to a portion of PAPP-A2 where there is little or no identity or complementarity with any known or prior art molecule. For this purpose, such oligonucleotide probes will generally comprise between about 10 nucleotides and 50 nucleotides, and preferably between about 15 nucleotides and about 30 nucleotides.

"Animal" as used herein may be defined to include human, domestic or agricultural (cats, dogs, cows, sheep, etc) or test species (mouse, rat, rabbit, etc).

"Recombinant" may also refer to a polynucleotide which encodes PAPP-A2 and is prepared using recombinant DNA techniques. The DNAs which encode PAPP-A2 may also include allelic or recombinant variants and mutants thereof.

"Nucleic acid probes" are prepared based on the cDNA sequences which encode PAPP-A2 provided by the present invention. Nucleic acid probes comprise portions of the sequence having fewer nucleotides than about 6 kb, usually fewer than about 1 kb. After appropriate testing to eliminate false positives, these probes may be used to determine whether mRNAs encoding PAPP-A2 are present in a cell or tissue or to isolate similar nucleic acid sequences from chromosomal DNA extracted from such cells or tissues as described in (Walsh et al., 1992, *PCR Methods Appl* 1, 241-50). Probes may be derived from naturally occurring or recombinant single- or double-stranded nucleic acids or be chemically synthesized. They may be labeled by nick translation, Klenow fill-in reaction, PCR or other methods well known in the art. Probes of the present invention, their preparation and/or labeling are elaborated in (Sambrook et al., 1989); or (Ausubel et al., 1989).

Alternatively, recombinant variants encoding these PAPP-A2 or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations may also be introduced to modify the properties of the polypeptide, including but not limited to activity, interchain affinities, or polypeptide degradation or turnover rate. One example involves inserting a stop codon into the nucleotide sequence to limit the size of PAPP-A2 so as to provide a molecule of smaller molecular weight.

"Expression vectors" are defined herein as DNA sequences that are required for the transcription of cloned copies of genes and the translation of their mRNAs in an appropriate host. Such vectors can be used to express eukaryotic genes in a variety of hosts such as bacteria, yeast, bluegreen algae, plant cells, insect cells and animal cells.

The term "antibody" as used herein includes both polyclonal and monoclonal antibodies, as well as fragments thereof, such as, Fv, Fab and F(ab)2 fragments that are capable of binding antigen or hapten. It includes conventional murine monoclonal antibodies as well as human antibodies, and humanized forms of non-human antibodies, and it also includes 'antibodies' isolated from phage antibody libraries.

"Ribozymes" are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of PAPP-A2 RNA sequences. Specific ribozyme cleavage sites within any potential RNA target are initially identified by scanning the target molecule for ribozyme cleavage sites which include the following sequences, GUA, GUU and GUC. Once identified, short RNA sequences of between fifteen (15) and twenty (20) ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

BRIEF DESCRIPTION OF THE DRAWINGS

FIGS. 1A-1F show the cDNA sequence (in 5'→3' orientation) corresponding to the mRNA that encodes preproPAPP-A2. Only the coding part of the sequence and the terminal stop codon (*) is shown and is numbered 1-5376. The translated polypeptide sequence of preproPAPP-A2 is also shown. The signal peptide cleavage site was predicted using SignalP V2.0 to be after the alanine residue encoded by nt. 64-66 ((Nielsen et al., 1997, *Protein Eng* 10, 1-6), WWW prediction server is located at genome.cbs.dtu.dk/). The signal peptide of preproPAPP-A2 (nt. 1-66, 22 residues) is shown in bold. The nucleotide sequence of this figure represents nt. 1 to 5376 of SEQ ID NO:1. The protein sequence of this figure is illustrated as SEQ ID NO:2.

FIGS. 3A-3G show the amino acid sequence of prepro-PAPP-A2 (SEQ ID NO:2) aligned with preproPAPP-A. The deduced amino acid sequence of preproPAPP-A2 (PA2) was aligned with the sequence of preproPAPP-A (PA) ((Haaning et al., 1996, *Eur J Biochem* 237, 159-63), AAC50543) using CLUSTAL W (Thompson et al., 1994, *Nucleic Acids Res* 22, 4673-80). Because the prepro-portion of PAPP-A did not show significant identity with the corresponding region of PAPP-A2, the alignment was manually adjusted to emphasize difference in length of pro-peptides. Arrows indicate the N-termini of the mature proteins as found earlier for PAPP-A (Kristensen et al., 1994, *Biochemistry* 33, 1592-8) (Glu-81), and here for PAPP-A2 (Ser-234). Putative signal peptides, strongly predicted using SignalP V2.0 (Nielsen et al., 1997, *Protein Eng* 10, 1-6) are shown with lower case letters. The pro-portion of PAPP-A2 contains one other candidate initiation codon corresponding to Met-168, but no signal peptide was predicted following this residue using SignalP. The sequence motifs of PAPP-A (Kristensen et al., 1994, *Biochemistry* 33, 1592-8) are also found in PAPP-A2: The catalytic zinc binding motif and residues of the putative Met-turn are underlined and bolded in both sequences. Lin-notch motifs (LNR1-3) and short consensus repeats (SCR-1-5) are boxed. All cysteines of mature PAPP-A are also found in PAPP-A2. In addition, the secreted form of PAPP-A2 has four cysteine residues (Cys-343, Cys-533, Cys-618, and Cys-1268) with no counterpart in PAPP-A.

FIGS. 7A-7C show the cDNA sequence of the PAPP-A2 mRNA coding region directly followed by the sequence of the 3'UTR. The sequence of the 3'UTR was obtained as detailed in Example 6.3 The first 5376 nucleotides of this sequence (nt. 1-5376) represents the coding sequence as illustrated in FIG. 1 and SEQ ID NO:1 (nt. 1-5376). Nucleotides 5377-8527 of this sequence corresponds to the 3'UTR of the PAPP-A2 mRNA as illustrated in SEQ ID NO:3 (nt. 5377-8527).

DETAILED DESCRIPTION OF THE INVENTION

Isolation of a Nucleotide Sequence Encoding PAPP-A2

The present invention in one aspect relates to a novel cDNA sequence encoding a protein with global homology to pregnancy-associated plasma protein-A (PAPP-A). This protein has been denoted PAPP-A2. The complete nucleotide sequence of PAPP-A2 has been obtained from mRNA isolated from human placenta (Example 1). The complete nucleotide sequence (SEQ ID NO:1) and translated amino acid sequence (SEQ ID NO:2) of PAPP-A2 are both shown in FIG. 1.

Figure 2:
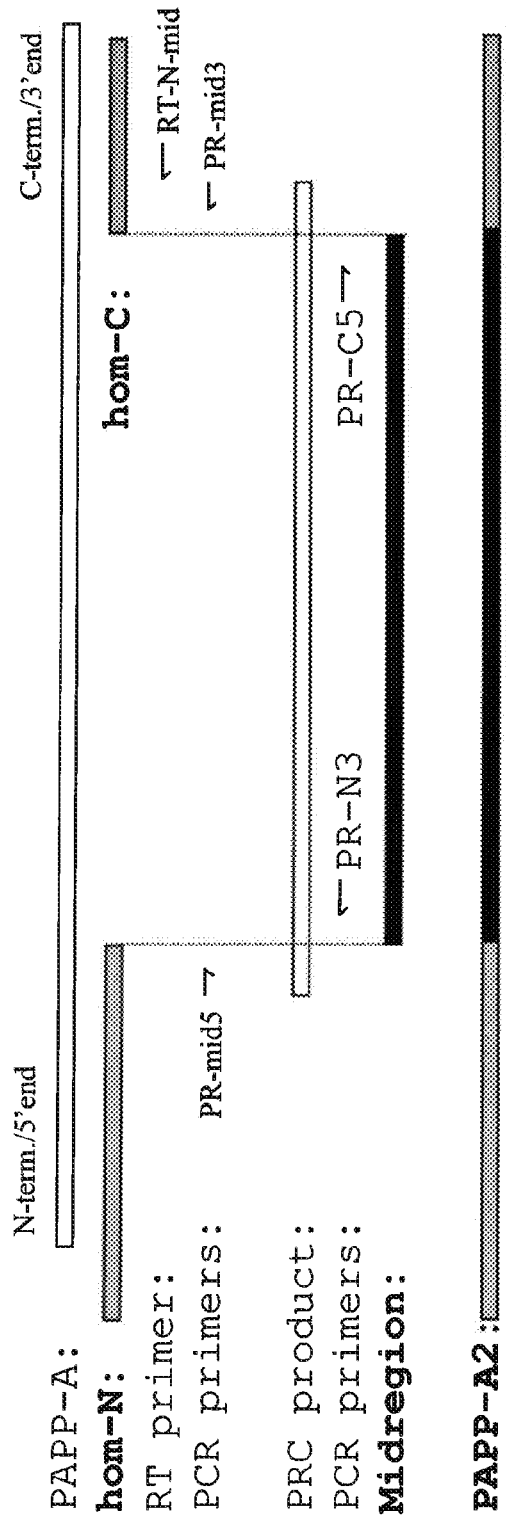
FIG. 2 is a schematic drawing of the relationship between PAPP-A (Kristensen et al., 1994, *Biochemistry* 33, 1592-8), and sequence stretches contained within two genomic clones with homology to the N-terminal end (hom-N, coding portion of accession number AL031734) and the C-terminal end (hom-C, coding portion of accession number AL031290) of PAPP-A, when translated into amino acid sequence. This figure also illustrates the method by which a cDNA sequence with homology to the midregion of PAPP-A was obtained. Hom-N, hom-C, and the midregion together encodes the complete sequence of a novel protein, PAPP-A2, which is a homolog of PAPP-A. The midregion was obtained by PCR using specifically primed (primer RT-N-mid), reversed transcribed human placental mRNA as the template, and primers PR-mid5 and PR-mid3 for the PCR (Table 1). To obtain a cDNA construct encoding the full-length PAPP-A2, cDNA clones corresponding to the genomic clones hom-N and hom-C were also obtained using cDNA synthesized with specifically primed placental mRNA as the template (primers not shown, see Table 1). This required identification of a signal peptide stretch (in hom-N) and a stop codon (at the 3' end of hom-C), as detailed in the main text. All primers used are shown in Table 1. Note: The relative positions of the sequences depicted here are in accordance with the experiments performed, but the figure is not accurately drawn to scale.

Homology of PAPP-A2 with PAPP-A is evident upon alignment of the two amino acid sequences as shown in FIG. 3. PAPP-A2 and PAPP-A share approximately 45% of their amino acid residues. Sequence motifs known to be important for the function of PAPP-A (Kristensen et al., 1994, *Biochemistry* 33, 1592-8; Lawrence et al., 1999, *Proc Natl Acad Sci USA* 96, 3149-53; Overgaard et al., 2000, *J Biol Chem*) are also found in PAPP-A2. Principally, PAPP-A2 contains an elongated zinc binding motif (HEXXHXXGXXH (SEQ ID NO:3), amino acids shown by one letter code) at position 733-743 (FIG. 2). This motif and a structurally important methionine residue, are strictly conserved within the metzincins, a superfamily of zinc peptidases (Bode et al., 1993, *FEBS Lett* 331, 134-40; Stocker et al., 1995, *Protein Sci* 4, 823-40).

Like PAPP-A, PAPP-A2 is synthesized as a prepro-protein. PreproPAPP-A2 has 1791 amino acids (FIG. 1). There is no homology between the prepro-portions of PAPP-A and PAPP-A2. Further, the prepro-portions of the two proteins differ significantly in length. The PAPP-A2 prepro-peptide has 233 residues (FIG. 3); the PAPP-A prepro-peptide has 80 residues (Haaning et al., 1996, *Eur J Biochem* 237, 159-63).

Uses of the Nucleotide Sequence Encoding PAPP-A2

The nucleotide sequence encoding PAPP-A2 (or its complement) have numerous applications in techniques known to those skilled in the art of molecular biology. These techniques include use as hybridization probes, use in the construction of oligomers for PCR, use in the recombinant production of PAPP-A2 or fragments hereof, and use in generation of anti-sense DNA or RNA, their chemical analogs (e.g. PNA or LNA) and the like. Uses of nucleotides encoding PAPP-A2 disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of PAPP-A2-encoding nucleotide sequences, some bearing minimal homology to the nucleotide sequence of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring PAPP-A2, and all such variations are to be considered as being specifically disclosed.

Although the nucleotide sequences which encode PAPP-A2 and/or its variants are preferably capable of hybridizing to the nucleotide sequence of the naturally occurring PAPP-A2 under stringent conditions, it may be advantageous to produce nucleotide sequences encoding PAPP-A2 or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding PAPP-A2 and/or its derivatives without altering the encoded amino acid sequence include the production of RNA transcripts having more desirable properties, such as a greater half-life, than transcripts produced from the naturally occurring sequence.

Nucleotide sequences encoding PAPP-A2 may be joined to a variety of other nucleotide sequences by means of well established recombinant DNA techniques (Sambrook et al., 1989). Useful nucleotide sequences for joining to PAPP-A2 include an assortment of cloning vectors, e.g., plasmids, cosmids, lambda phage derivatives, phagemids, and the like, that are well known in the art. Vectors of interest include expression vectors, replication vectors, probe generation vectors, sequencing vectors, and the like. In general, vectors of interest may contain an origin of replication functional in at least one organism, convenient restriction endonuclease sensitive sites, and selectable markers for the host cell.

Another aspect of the subject invention is to provide for PAPP-A2-specific nucleic acid hybridization probes capable of hybridizing with naturally occurring nucleotide sequences encoding PAPP-A2. Such probes may also be used for the detection of similar PAPP-A2 encoding sequences and should preferably contain at least 50% of the nucleotides from the conserved region or active site. The hybridization probes of the subject invention may be derived from the nucleotide sequences of the SEQ ID NO:1 or from genomic sequences including promoters, enhancer elements and/or possible introns of the respective naturally occurring PAPP-A2. Hybridization probes may be labeled by a variety of reporter groups, including radionuclides such as 32P or 35S, or enzymatic labels such as alkaline phosphatase coupled to the probe via avidin/biotin coupling systems, and the like.

PCR as described (U.S. Pat. Nos. 4,683,195; and 4,965,188) provides additional uses for oligonucleotides based upon the nucleotide sequence which encodes PAPP-A2. Such probes used in PCR may be of recombinant origin, may be chemically synthesized, or a mixture of both and comprise a discrete nucleotide sequence for diagnostic use or a degenerate pool of possible sequences for identification of closely related genomic sequences.

Other means of producing specific hybridization probes for PAPP-A2 DNAs include the cloning of nucleic acid sequences encoding PAPP-A2 or PAPP-A2 derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is possible to produce a DNA sequence, or portions thereof, encoding PAPP-A2 and their derivatives entirely by synthetic chemistry, after which the gene can be inserted into any of the many available DNA vectors using reagents, vectors and cells that are known in the art at the time of the filing of this application. Moreover, synthetic chemistry may be used to introduce mutations into the PAPP-A2 sequences or any portion thereof.

The nucleotide sequence can be used in an assay to detect disease associated with abnormal levels of expression of PAPP-A2. The nucleotide sequence can be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. Alternatively, levels of PAPP-A2 mRNA can be measured by micro array techniques using immobilized probes. Expression in samples can also be evaluated by (semi-quantitative) RT-PCR. Expression in samples can alternatively be evaluated by techniques based on hybridization. For example, in situ hybridization can be used to detect PAPP-A2 mRNA. This technique has the advantage that it locates the cells that synthesize the mRNA, but also is less sensitive than RT-PCR.

Included in the scope of the invention are oligoribonucleotide sequences, that include antisense RNA and DNA molecules and ribozymes that function to inhibit translation of PAPP-A2. Antisense techniques are known in the art and may be applied herein. Both antisense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

The invention also relates to unknown PAPP-A2 genes isolated from other species and alleles of the PAPP-A2 gene, in which PAPP-A2 orthologues or homologues exists. A bacteriophage cDNA library may be screened, under conditions of reduced stringency, using a radioactively labeled fragment of the human PAPP-A2 clone described herein. Alternatively the human PAPP-A2 sequence can be used to design degenerate or fully degenerate oligonucleotide probes which can be used as PCR probes or to screen bacteriophage cDNA libraries. The PCR product may be subcloned and sequenced to insure that the amplified sequences represent the PAPP-A2 sequences. The PCR fragment may be used to isolate a full length PAPP-A2 clone by radioactively labeling the amplified fragment and screening a bacteriophage cDNA library. Alternatively, the labeled fragment may be used to screen a genomic library. For a review of cloning strategies which may be used, see e.g., (Ausubel et al., 1989; Sambrook et al., 1989).

Expression of Recombinant PAPP-A2

In order to express a biologically active proteinase, the nucleotide sequence coding for the protein, or a functional equivalent, can be inserted into an appropriate expression vector, i.e., a vector which contains the necessary elements for the transcription and translation of the inserted coding sequence. For example, recombinant protein can be used for immunization to obtain antibodies, as a laboratory reagent, and in diagnostic kits.

More specifically, methods which are well known to those skilled in the art can be used to construct expression vectors containing the PAPP-A2 sequence and appropriate transcriptional/translational control signals. These methods include in vitro recombinant DNA techniques, synthetic techniques and in vivo recombination/genetic recombination. See e.g., the techniques described in (Ausubel et al., 1989; Sambrook et al., 1989).

Further, expression vectors containing fragments of the PAPP-A2 encoding sequence may also be constructed. In particular, this may be relevant for the use of portions of the PAPP-A2 polypeptide as an antigen for immunization. In addition, the coding sequence of PAPP-A2 or fragments hereof may be cloned in frame with a coding nucleotide sequence present in the vector to result in a fusion protein or a 'tagged' PAPP-A2 protein. For example, such a fusion protein may be composed of PAPP-A2 and GST, and such tag may be a c-myc tag (for detection) and/or a histidine tag (for purification).

A variety of host-expression vector systems may be utilized to express the PAPP-A2 coding sequence or fragments hereof. These include but are not limited to microorganisms such as bacteria transformed with recombinant bacteriophage DNA, plasmid DNA or cosmid DNA expression vectors containing the PAPP-A2 coding sequence; yeast transformed with recombinant yeast expression vectors containing the PAPP-A2 coding sequence; insect cell systems infected with recombinant virus expression vectors (e.g., baculovirus) containing the PAPP-A2 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the PAPP-A2 coding sequence; or animal cell systems infected with recombinant virus expression vectors (e.g., adenovirus, vaccinia virus, human tumor cells) including cell lines engineered to contain multiple copies of the PAPP-A2 DNA either stably amplified (CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the CMV promotor, the adenovirus late promoter; the vaccinia virus 7.5K promoter) may be used; when generating cell lines that contain multiple copies of the PAPP-A2 DNA SV40-, BPV- and EBV-based vectors may be used with an appropriate selectable marker.

The expression vector may be introduced into host cells via any one of a number of techniques including but not limited to transformation, transfection, infection, protoplast fusion, and electroporation. The expression vector-containing cells are clonally propagated and individually analyzed to determine whether they produce PAPP-A2 protein. Identification of PAPP-A2 expressing host cell clones may be done by several means, including but not limited to immunological reactivity with anti-PAPP-A2 antibodies, and the presence of host cell-associated PAPP-A2 activity.

In bacterial systems, a number of expression vectors may be advantageously selected depending upon the use intended for the PAPP-A2 expressed. For example, when large quantities of PAPP-A2 are to be produced, vectors which direct the expression of high levels of fusion protein products that are readily purified may be desirable. Such vectors include but are not limited to the *E. coli* expression vector pUR278 (Ruther and Muller-Hill, 1983, *Embo J* 2, 1791-4), in which the PAPP-A2 coding sequence may be ligated into the vector in frame with the lac Z coding region so that a hybrid AS-lac Z protein is produced. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety. In yeast, a number of vectors containing constitutive or inducible promoters may be used. For a review, see (Ausubel et al., 1989; Bitter et al., 1987, *Methods Enzymol* 153, 516-44; Rosenfeld, 1999, *Methods Enzymol* 306, 154-69).

In cases where plant expression vectors are used, the expression of the PAPP-A2 coding sequence may be driven by any of a number of promoters. For example, viral promoters such as the 35S RNA and 19S RNA promoters of CaMV may be used (Gmunder and Kohli, 1989, *Mol Gen Genet* 220, 95-101); alternatively, plant promoters such as the small subunit of RUBISCO (Broglie et al., 1984, *Science* 224, 838-43).

An alternative expression system which could be used to express PAPP-A2 is an insect system. In one such system, Baculovirus is used as a vector to express foreign genes. The virus then grows in the insect cells. The PAPP-A2 coding sequence may be cloned into non-essential regions (for example the polyhedron gene) of the virus and placed under control of a Baculovirus promoter. These recombinant viruses are then used to infect insect cells in which the inserted gene is expressed. For example, see (Smith et al., 1983, *Mol Cell Biol* 3, 2156-65).

A variety of mammalian expression vectors may be used to express recombinant PAPP-A2 in mammalian cells. Commercially-available mammalian expression vectors which may be suitable for recombinant PAPP-A2 expression, include but are not limited to, pMC1neo (Stratagene), pXT1

(Stratagene), pSG5 (Stratagene), EBO-pSV2-neo (ATCC 37593), pBPV-1 (8-2) (ATCC 37110), pcDNA3.1 and its derivatives (Stratagene). Cell lines derived from mammalian species which may be suitable and which are commercially available, include but are not limited to, CV-1, COS-1, COS-7, CHO-K1, 3T3, NIH3T3, HeLa, C127I, BS-C-1, MRC-5, and 293. Further, in mammalian host cells, a number of viral based expression systems may be utilized. In cases where an adenovirus is used as an expression vector, the PAPP-A2 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing PAPP-A2 in infected hosts. See for example (Logan and Shenk, 1984, *Proc Natl Acad Sci USA* 81, 3655-9). Alternatively, the vaccinia 7.5K promoter may be used. See for example (Mackett et al., 1982, *Proc Natl Acad Sci USA* 79, 7415-9).

For long-term, high-yield production of recombinant proteins, stable expression is preferred. For example, cell lines which stably express PAPP-A2 may be engineered. Rather than using expression vectors which contain viral origins of replication, host cells can be transformed with PAPP-A2 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

Some applications of the recombinant PAPP-A2 may require the protein to be in purified or partially purified form. Recombinantly expressed PAPP-A2 or fragments of the PAPP-A2 polypeptide can be isolated by liquid chromatography. Various methods of protein purification well known in the art include those described in for example (Scopes, 1987). Alternatively, recombinant PAPP-A2 fusion proteins or 'tagged' PAPP-A2 may be purified by affinity chromatography. Further, antibodies raised against PAPP-A2 may be used for purification by immunoaffinity chromatography.

Recombinant variant of PAPP-A2 may be produced by site directed mutagenesis. In some applications of PAPP-A2 such variants may be preferred due to for example increased protein stability, or changes in activity.

Production and Uses of Antibodies Against PAPP-A2

The recombinant protein may be used to generate antibodies. Monospecific antibodies to PAPP-A2 can be purified from mammalian antisera containing antibodies reactive against PAPP-A2 or can be prepared as monoclonal antibodies reactive with PAPP-A2 using standard techniques.

Monospecific antibody as used herein is defined as a single antibody species or multiple antibody species with homogenous binding characteristics for PAPP-A2. Homogenous binding as used herein refers to the ability of the antibody species to bind to a specific antigen or epitope, such as those associated with the PAPP-A2, as described above. PAPP-A2 specific antibodies are raised by immunizing animals such as mice, rats, guinea pigs, rabbits, goats, horses and the like, with rabbits or mice being preferred, with an appropriate concentration of PAPP-A2 either with or without an immune adjuvant. For example, antibodies specific against PAPP-A2 can be used for the purification of native and recombinant PAPP-A2, as a laboratory reagent, and in antibody based diagnostic kits.

Monoclonal antibodies (mAb) reactive with PAPP-A2 can be prepared by conventional methods, such as by immunizing inbred mice with PAPP-A2. The mice are immunized with about 0.1 mg to about 10 mg, preferably about 1 mg, of PAPP-A2 in about 0.5 ml buffer or saline incorporated in an equal volume of an acceptable adjuvant. Freund's complete adjuvant is preferred. The mice receive an initial immunization on day 0 and are rested for about 3 to about 30 weeks. Immunized mice are given one or more booster immunizations of about 0.1 to about 10 mg of PAPP-A2 in a buffer solution such as phosphate buffered saline (PBS) by the intravenous (IV) route. Lymphocytes from antibody-positive mice are obtained by removing spleens from immunized mice by standard procedures known in the art. Hybridoma cells are produced by mixing the splenic lymphocytes with an appropriate fusion partner under conditions which will allow the formation of stable hybridomas. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using PAPP-A2 as the antigen. The culture fluids are also tested in the Ouchterlony precipitation assay to determine the isotype of the mAb. Hybridoma cells from antibody positive wells are then cloned. For details, see (Peters and Baumgarten, 1992).

In vitro production of anti-PAPP-A2 is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique (Crowther, 1995).

The "monoclonal antibodies" may also be isolated from phage antibody libraries using the techniques described in (Clackson et al., 1991, *Nature* 352, 624-8; Marks et al., 1991, *J Mol Biol* 222, 581-97), for example. Identified phage antibodies can be produced by expression in bacteria.

Methods such as those described above may be used to produce monospecific antibodies specific for PAPP-A2 polypeptide fragments or full-length nascent PAPP-A2 polypeptide.

PAPP-A2 antibody affinity columns can be made by adding the antibodies to a gel support, such as Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing PAPP-A2 or PAPP-A2 fragments are slowly passed through the column. The column is then washed, and the protein is eluted. The purified PAPP-A2 protein is then dialyzed against phosphate buffered saline.

Native PAPP-A2 from sources such as human plasma or serum, tissue extracts, or media from nontransfected cell lines (that endogenously secrete PAPP-A2) may also be purified by use of an antibody affinity column.

Using polyclonal or monoclonal antibodies against PAPP-A2 a number of assays may be constructed for measurement of PAPP-A2 antigen in body fluids or tissue and cell extracts. Kits based on antibodies may be used for diagnostic purposes. The assays include, but are not limited to, precipitation, passive agglutination, enzyme-linked immunosorbent assay (ELISA) techniques, and radioimmunoassay (RIA) techniques.

For example, in one such ELISA, a sandwich assay can be constructed where antigen present in an sample is caught by immobilized polyclonal anti(PAPP-A2). Detection is then performed by the use of one or more monoclonal PAPP-A2 antibodies and peroxidase conjugated anti(murine IgG). In another assay, antigen present in an sample is caught by immobilized polyclonal anti(PAPP-A2), and detected using biotinylated polyclonal anti(PAPP-A2). For further examples and details, see (Crowther, 1995). Assays can be calibrated using purified PAPP-A2 to construct a standard curve by serial dilution. The concentration of PAPP-A2 in solution in a purified form can be accurately measured by amino acid analysis (Sottrup-Jensen, 1993, *Biochem Mol Biol Int* 30, 789-94).

Polyclonal antibodies may be used to inhibit the biological activity of PAPP-A2. Specifically, in analogy with the inhibition of the IGFBP-4 proteolytic activity of PAPP-A by polyclonal PAPP-A antibodies (Lawrence et al., 1999, *Proc Natl Acad Sci USA* 96, 3149-53), anti(PAPP-A2) may be used to inhibit the proteolytic activity of PAPP-A2. Certain monoclonal antibodies may also be inhibitory towards the activity of PAPP-A2. Such monoclonal antibodies are likely to recognize an epitope in close proximity to the active site of PAPP-A2, but the inhibitory activity may also be based on binding to epitopes other than those close to the active site. Inhibitory monoclonal antibodies can be obtained by immunization with PAPP-A2, PAPP-A2 fragments, with peptides derived from PAPP-A2.

Inhibitory (monoclonal) antibodies may have therapeutic value in conditions of pathologies in which it may be desirable to decrease the activity of PAPP-A2.

Activity of PAPP-A2

Like PAPP-A, PAPP-A2 contains conserved amino acid stretches that classify it as a putative metalloproteinase of the metzincin superfamily (Stocker et al., 1995, *Protein Sci* 4, 823-40). It has been experimentally verified that PAPP-A2 does exhibit proteolytic activity by demonstrating its cleavage of insulin-like growth factor binding protein (IGFBP)-5 (Example 6.7).

In general, proteolytic activity of PAPP-A2 against potential protein substrates may be evaluated by the incubation of purified or partially purified PAPP-A2 with the potential substrate under a variety of experimental conditions (such as for example temperature, buffer composition, ionic strength, and pH). Enzymatic activity of PAPP-A2 against the protein in question can be evaluated by SDS-PAGE (in which degradation or release of well defined proteolytic fragment(s) will be evident), or by high-pressure liquid chromatographic detection of released peptide(s). By means of such procedures, other substrate targets of PAPP-A2 may be identified. Incubation with a variant of PAPP-A2 where, for example, a residue in the active site has been substituted to obtain an inactive enzyme, serves as a proper negative control.

Random peptide libraries consisting of all possible combinations of amino acids attached to a solid phase support may be used to identify peptides that can be cleaved by PAPP-A2. Identification of such peptides may be accomplished by screening a peptide library with recombinant soluble PAPP-A2. Methods for expression and purification of the enzyme are described above and may be used to express recombinant full length PAPP-A2 or fragments, analogs, or derivatives thereof depending on the functional domains of interest. For further details, see (Meldal, 1998, *Methods Mol Biol* 87, 65-74; Meldal, 1998, *Methods Mol Biol* 87, 51-7). Alternatively, peptide substrates may be derived from identified protein substrates of PAPP-A2.

Alternatively, phage display of peptide libraries may be used to identify peptides that can be cleaved by PAPP-A2 (Matthews and Wells, 1993, *Science* 260, 1113-7).

Peptides that function as PAPP-A2 substrates may function in assays for the detection of PAPP-A2 proteolytic activity in body fluids or tissue and cell extracts. Substrate peptides may be derivatized to function in an assay based on quenched-fluorescence (Meldal, 1998, *Methods Mol Biol* 87, 65-74). Kits based on such, or other, techniques may be used for diagnostic purposes in pathologies where measurement of PAPP-A2 activity is relevant.

Identification of Agents that Modify the Activity of PAPP-A2

An assay for the detection of PAPP-A2 proteolytic activity, as described above, provides a method for the identification of molecules that modify the activity of PAPP-A2. Such molecules may be, for example, peptides, derivatized peptides, hydroxamic acid derivatized peptides, small organic molecules, or antibodies.

The screening of peptide libraries can be used to discover pharmaceutical agents that act to modulate and/or inhibit the biological activity of PAPP-A2. Methods for expression and purification of the enzyme are described above and may be used to express recombinant full length PAPP-A2 or fragments, analogs, or derivatives thereof depending on the functional domains of interest. Random peptide libraries consisting of all possible combinations of amino acids attached to a solid phase support may be used to identify peptides that are able to modulate and/or inhibit PAPP-A2 activity by binding to the active site or other sites of PAPP-A2. For example, see (Meldal, 1998, *Methods Mol Biol* 87, 75-82).

Similarly, combinatorial chemistry may be used to identify low molecular weight organic molecules that affect the activity of PAPP-A2.

Measurement of Complexes of PAPP-A or PAPP-A2

PAPP-A primarily exists in pregnancy serum as a disulfide bound 2:2 complex with the proform of eosinophil major basic protein (proMBP), PAPP-A/proMBP. In addition to the PAPP-A/proMBP complex, proMBP exists in the circulation as a disulfide bound 2:2 complex with angiotensin (ANG), proMBP/ANG, and a fraction of this complex is further complexed to a fragment of complement component C3dg (PROMBP/ANG/C3dg) (Oxvig, 1995; Christiansen, 2000).

The level of complexes comprising PAPP-A and/or PAPP-A2 and/or proMBP in body fluids of an individual may be indicative of predisposition to a clinical condition or indicative of the presense of a clinical condition. Accordingly, the present invention in one embodiment is directed towards a method of diagnosing a clinical condition or diagnosing predisposition to said clinical condition in an individual comprising the steps of a) providing a body sample from said individual; and
    b) measuring the level of a complex selected from the group consisting of PAPP-A/proMBP, PAPP-A2/proMBP, PAPP-A/PAPP-A2, PAPP-A/PAPP-A2/proMBP, proMBP/ANG and proMBP/ANG/C3dg in said body fluid sample; and c) diagnosing the clinical condition or diagnosing predisposition to the clinical condition, wherein the level of the complex above or below a predetermined value is indicative of the clinical condition or predisposition to the clinical condition.

Furthermore, the levels of complexes comprising PAPP-A and/or PAPP-A2 and/or proMBP in body fluids of a mammalian mother may be indicative of predisposition to a clinical condition or indicative of the presense of a clinical condition in a fetus of said mother. Hence, the present invention provides methods of diagnosing a clinical condition or diagnosing predisposition to said clinical condition in a mammalian fetus comprising the steps of a) providing a body fluid sample from the mother of said fetus; and b) measuring the level of a complex selected from the group consisting of PAPP-A/proMBP, PAPP-A2/proMBP, PAPP-A/PAPP-A2, PAPP-A/PAPP-A2/proMBP, proMBP/ANG and proMBP/ANG/C3dg in said body fluid sample; and c) diagnosing the clinical condition or diagnosing predisposition to the clinical condition, wherein the level of the complex above or below a predetermined value is indicative of the clinical condition or predisposition to the clinical condition.

In particular, according to the present method the level of one or more of the following complexes may be determined:
PAPP-A/proMBP
PAPP-A2 and proMBP (PAPP-A2/proMBP)
PAPP-A2 and PAPP-A (PAPP-A/PAPP-A2)
PAPP-A/PAPP-A2 with proMBP (PAPP-A/PAPP-A2/proMBP)
proMBP/ANG
proMBP/ANG/C3dg The level of complexes comprising PAPP-A and/or PAPP-A2 and/or proMBP in a body fluid sample may be determined by any conventional method known to the person skilled in the art. For example, the level can be measured by a method comprising the use of immunospecific reagents specifically interacting with one or more components of the complex desirable to measure, such as immunospecific reagents specifically interacting with PAPP-A, PAPP-A2, proMBP, ANG or C3gd. Immunospecific reagents may for example bemonoclonal antibodies, polyclonal antibodies and/or antigen binding fragments thereof, specific towards the individual components of the complex.

Such methods include but are not limited to sandwich ELISA, wherein an immunospecific reagent specifically recognising one component of the complex is employed as catching antibody and another immunospecific reagent specifically recognising another component if the complex is employed as detection antibody. The detection antibody is preferably either directly or indirectly detectable, for example the detection antibody may be directly coupled to a detectable label or the detection antibody may be capable of interacting with another agent which is coupled to a detectable label.

A detectable label may for example be a fluorescent label, a chromatophore, a radioactive label, a heavy metal or an enzyme.

For example, the level of PAPP-A/proMBP complexes in a body fluid sample may be determined by sandwich ELISA using a PAPP-A specific monoclonal or polyclonal antibody for catching and a proMBP specific monoclonal or polyclonal antibody for detection or the level of proMBP/ANG in a body fluid sample may be determined by sandwich ELISA using a proMBP specific monoclonal or polyclonal antibody for catching and a ANG specific monoclonal or polyclonal antibody for detection.

The clinical condition may be any clinical condition which may be diagnosed by the level of complexes comprising PAPP-A and/or PAPP-A2 and/or proMBP or wherein predisposition may be diagnosed by the level of complexes comprising PAPP-A and/or PAPP-A2 and/or proMBP. The clinical condition may for example be selected from the group comprising Down's syndrome, preeclampsia and acute coronary syndrome, including unstable angina and myocardial infarction.

The body fluid sample may be any useful body fluid sample, such as a blood sample including a serum sample, a urine sample, a saliva sample or an amniotic fluid sample.

In particular, the level of PAPP-A/proMBP may be determined when the clinical condition is selected from the group consisting of Down's syndrome, and acute coronary syndrome including unstable angina and myocardial infarction.

In one embodiment of the present invention diagnosing Down's syndrome or diagnosing predisposition to Down's syndrome, comprises determining the level of PAPP-A/proMBP, wherein the level of PAPP-A/proMBP below a predetermined value is indicative of the Down's syndrome or predisposition to Down's syndrome.

In another embodiment of the present invention diagnosing acute coronary syndrome, including unstable angina and myocardial infarction or diagnosing predisposition to acute coronary syndrome, including unstable angina and myocardial infarction, comprises determining the level of PAPP-A/proMBP, wherein the level of PAPP-A/proMBP above a predetermined value is indicative of the acute coronary syndrome, including unstable angina and myocardial infarction or predisposition to acute coronary syndrome, including unstable angina and myocardial infarction.

In yet another embodiment the level of proMBP/ANG may be determined to diagnose predisposition to Down's syndrome or to diagnose Down's syndrome. All the above mentioned methods of diagnosis may also be performed in combination with one or more other methods of diagnosis. In addition, more than one different diagnosis according to the present invention may be performed, for example it is possible to measure the level of more than one complex or to measure the level of one complex in different body samples.

Use of PAPP-A2 to Generate Natural Proteolytic Fragments

PAPP-A2 may be used to generate natural fragments of proteins that are specifically cleaved by PAPP-A2. As in the case of IGFBP-5 (see Examples 6.7 and 6.9), such fragments may have biological effects different from intact IGFBP-5. Fragments can be purified by standard chromatography after cleavage with purified PAPP-A2 (see Example 6.9).

Design of Fragments of PAPP-A2 for Expression

Figure 8:
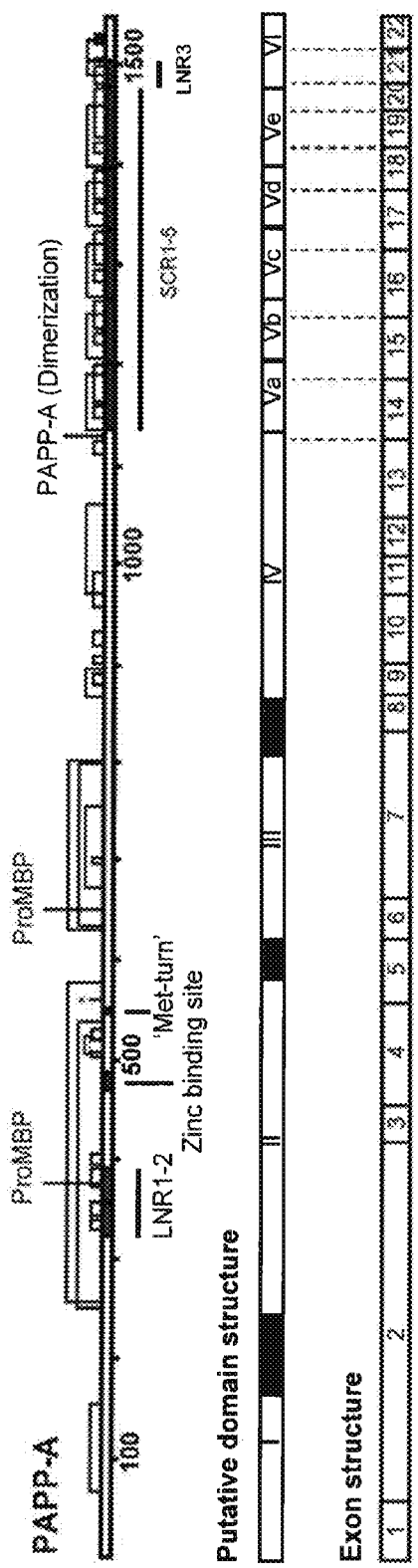
FIG. 8 shows the disulfide structure of the PAPP-A subunit in the PAPP-A/proMBP complex (upper bar). Cysteine containing peptides originating from the PAPP-A/proMBP complex were isolated by degrading PAPP-A/proMBP complex with proteinases and cyanogen bromide followed by standard HPLC. Peptides were identified by amino acid analysis, N-terminal sequence analysis, and by mass spectrometry (Overgaard, M. T., Oxvig, C., unpublished). Disulfide bonds are shown by thin lines. Two cysteine residues form interchain disulfide bridges to proMBP, and one forms an interchain bridge to PAPP-A causing it to be a dimer (as indicated). Asterisks mark a cysteine residue to which no partner has been found. The cysteine residues present in mature PAPP-A is also present in mature PAPP-A2 (see FIG. 3). It is reasonable to assume that the disulfide pairing of PAPP-A2 is the same. Thus, this information is valuable in determination of boundary regions for expression of isolated domains (fragments) of PAPP-A2. The gene structure of PAPP-A is also show (lower bar). Exon/intron boundaries are based on comparison of PAPP-A cDNA (AN X68280) with genomic sequences (ANs AB020878, AL353141, and AL137024). The central bar shows putative domains of PAPP-A based on information of the upper and lower bars.

Because all cysteine residues found in mature PAPP-A are also found in mature PAPP-A2 (see FIG. 3), the pattern of disulfide bonds can be assumed to be the same for PAPP-A2 for those common cysteine residues. Therefore, knowledge of the disulfide structure of the PAPP-A subunit (see FIG. 8) can be used to rationally design fragments of PAPP-A2 in which pairing of all cysteine residues is possible. Putative domain boundaries of PAPP-A2 can be defined based on the disulfide structure shown in FIG. 8. Those domains can be expressed separately or in combination. In the event that a domain contains a cysteine residue known to form an inter-chain disulfide bridge to another PAPP-A subunit or to proMBP (see FIG. 8), it may be required that this cysteine is mutated to for example a serine or an alanine residue Thus, possible boundary regions are between Cys-403 and Cys-499, between Cys-828 and Cys-881, between Cys-1048 and Cys-1115, between Cys-1390 and Cys-1396, between Cys-1459 and Cys-1464, between Cys-1521 and Cys-1525, between Cys-1590 and Cys-1595, between Cys-1646 and Cys-1653, and between Cys-1729 and Cys-1733 (numbering of preproPAPP-A2, as in FIGS. 1 and 3).

Pharmaceutical Compositions

Identification of PAPP-A2 as the IGFBP-5 protease provides methods for affecting growth and differentiation in vivo by using PAPP-A2 as a therapeutic target. Inhibitors of PAPP-A2 is believed to decrease the amount of bioavailable IGF-I and IGF-II. For example, inhibition of PAPP-A2 activity can be useful in disorders such as restenosis, atherosclerosis, and fibrosis. Activators, or agents that increase the activity of PAPP-A2, is believed to increase the amount of bioavailable IGF-I and IGF-II.

Agents that alter PAPP-A2 activity or that alter adherence of PAPP-A2 to cell surfaces can be incorporated into pharmaceutical compositions. Such agents may be incorporated together with agents that alter PAPP-A activity or that alter adherence of PAPP-A to cell surfaces. A combination of PAPP-A2 specific agents and PAPP-A specific agents may be more effective than traditional agents directed against PAPP-A. There is also provided a method of treatment comprising the step of administering to an individual in need thereof a combination of PAPP-A2 specific agents and PAPP-A specific agents in pharmaceutically effective amounts.

As an example, an antibody such as anti-PAPP-A2 polyclonal or monoclonal, can be formulated into a pharmaceutical composition by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients (i.e., pharmaceutically acceptable carriers) sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration Medical Devices The invention also features a medical device for placement in a patient (e.g., an implant) that includes an agent that inhibits or activates PAPP-A2 protease activity. Suitable agents are readily identified using the methods described herein. The device can be impregnated with the agent or can be coated with the agent. Non-limiting examples of inhibitors include an antibody such as anti-PAPP-A2 polyclonal or monoclonal, or a metalloprotease inhibitor such as 1,10-phenanthroline.

IGFBP-5 protease activity of PAPP-A2 is potently inhibited by 1,10-phenanthroline, but is not inhibited by tissue inhibitors of matrix metalloproteases (TIMP'S). Other inhibitors include small molecules such as derivatives of hydroxamic acid. Anti-PAPP-A2 polyclonal IgG may also inhibit IGF-dependent—or IGF-independent—IGFBP-5 specific PAPP-A2 protease activity in HFCM in a dose-dependent manner.

In addition, polypeptides (i.e., any chain of amino acids, regardless of length or post-translational modification), including modified polypeptides, can function as inhibitors. Any inhibitor of the IGFBP-5 protease activity of PAPP-A2 can be used for coating or impregnating a medical device according to the invention. Modified polypeptides include amino acid substitutions, deletions, or insertions in the amino acid sequence as compared with a corresponding wild-type sequence, as well as chemical modifications. Although protease-resistant IGFBP-5 is not an inhibitor per se of the IGFBP-5 protease activity of PAPP-A2, similar results are expected when it is used for coating or impregnating a medical device.

As an example, coating or impregnating the medical device with a PAPP-A2 inhibitor, optionally in combination with a PAPP-A inhibitor, can help prevent the development of restenosis following balloon angioplasty, or can prevent a further increase in size of an atherosclerotic plaque. Coronary angioplasty with stent placement is currently the leading therapeutic approach for coronary atherosclerosis. An important goal of angioplasty of coronary artery disease is to prevent both acute and chronic complications. Modern procedures are quite successful in eliminating immediate problems. Unfortunately, restenosis still occurs in 20-30% of stented patients. No known pharmacological intervention is available to prevent the restenosis.

Without being bound by a particular mechanism, it is thought that an increase in IGFBP-5 protease expression by coronary smooth muscle cells precedes neointimal formation in response to angioplasty in humans.

For example, enhanced PAPP-A2 activity can be useful for wound healing, fractures, osteoporosis, or ovulation. Osteoporosis or other conditions of bone loss may benefit from increased bone formation and decreased bone resorption. Agents that enhance PAPP-A2 activity can be, for example, a modified IGF, i.e., an IGF analog.

Analogs include IGF polypeptides containing amino acid insertions, deletions or substitutions, as well as chemical modifications. Amino acid substitutions can include conservative and non-conservative amino acid substitutions. Conservative amino acid substitutions replace an amino acid with an amino acid of the same class, whereas non-conservative amino acid substitutions replace an amino acid with an amino acid of a different class. Non-conservative substitutions result in a change in the hydrophobicity of the polypeptide or in the bulk of a residue side chain. In addition, non-conservative substitutions can make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. Amino acid insertions, deletions and substitutions can be made using random mutagenesis, site-directed mutagenesis, or other recombinant techniques known in the art.

The medical device can be, for example, bone plates or bone screws that are used to stabilize bones, or a stent, which typically is used within the body to restore or maintain the patency of a body lumen. Blood vessels, for example, can become obstructed due to an atherosclerotic plaque that restricts the passage of blood. A stent typically has a tubular structure defining an inner channel that accommodates flow within the body lumen. The outer walls of the stent engage the inner walls of the body lumen. Positioning of a stent within an affected area can help prevent further occlusion of the body lumen and permit continued flow. A stent typically is deployed by percutaneous insertion of a catheter or guide wire that carries the stent. The stent ordinarily has an expandable structure. Upon delivery to the desired site, the stent can be expanded with a balloon mounted on the catheter. Alternatively, the stent may have a biased or elastic structure that is held within a sheath or other restraint in a compressed state. The stent expands voluntarily when the restraint is removed. In either case, the walls of the stent expand to engage the inner wall of the body lumen, and generally fix the stent in a desired position.

STATEMENTS OF INVENTION

In a first aspect the present invention relates to a purified polynucleotide selected from the group consisting of
  i) a polynucleotide comprising nucleotides 1 to 5376 of SEQ ID NO:1, corresponding to the coding sequence of PAPP-A2, as deposited with DSMZ under accession number DSM 13783; and
  ii) a polynucleotide encoding a polypeptide having the amino acid sequence as shown in SEQ ID NO:2; and
  iii) a polynucleotide encoding a fragment of a polypeptide encoded by polynucleotides (i) or (ii), wherein said fragment
    a) has a proteolytic activity specific for Insulin Like Growth Factor Binding Protein 5 (IGFBP-5), or a derivative thereof, or any other substrate; and/or
    b) is recognised by an antibody, or a binding fragment thereof, which is capable of recognising a polypeptide having the amino acid sequence as shown in SEQ ID NO:2; and/or
    c) competes with a polypeptide having the amino acid sequence as shown in SEQ ID NO:2 for binding to a cell surface receptor having an affinity for said polypeptide; and
  iv) a polynucleotide, the complementary strand of which hybridizes, under stringent conditions, with a polynucleotide as defined in any of (i), (ii) and (iii), said polynucleotide encoding a polypeptide having the amino acid sequence as shown in SEQ ID NO:2, or a fragment thereof, wherein said fragment
    a) has a proteolytic activity specific at least for Insulin Like Growth Factor Binding Protein 5 (IGFBP-5); and/or
    b) is recognised by an antibody, or a binding fragment thereof, which is capable of recognising a polypeptide having the amino acid sequence as shown in SEQ ID NO:2; and/or
    c) competes with a polypeptide having the amino acid sequence as shown in SEQ ID NO:2 for binding to a cell surface receptor having an affinity for said polypeptide; and
  v) a polynucleotide comprising a nucleotide sequence which is degenerate to the nucleotide sequence of a polynucleotide as defined in any of (iii) and (iv),
and the complementary strand of such a polynucleotide.

A polynucleotide as used herein shall denote any naturally occurring polynucleotide having any naturally occurring backbone structure, as well as nucleotides known in the art as LNA (locked nucleic acid) and PNA (peptide nucleic acid).

In preferred embodiments the purified polynucleotide comprises the coding sequence of PAPP-A2, nucleotides 1 to 5376, as shown in SEQ ID NO:1, or a nucleotide sequence encoding the amino acid sequence as shown in SEQ ID NO:2.

In another preferred embodiment the polynucleotide comprises a nucleotide sequence encoding a fragment of the polypeptide having the amino acid sequence as shown in SEQ ID NO:2, wherein said fragment
  a) has a proteolytic activity specific for Insulin Like Growth Factor Binding Protein 5 (IGFBP-5), or a derivative thereof, or any other substrate; and/or
  b) is recognised by an antibody, or a binding fragment thereof, which is capable of recognising a polypeptide having the amino acid sequence as shown in SEQ ID NO:2; and/or
  c) competes with a polypeptide having the amino acid sequence as shown in SEQ ID NO:2 for binding to a cell surface receptor having an affinity for said polypeptide There is also provided a polynucleotide, the complementary strand of which hybridizes, under stringent conditions, with a polynucleotide according to the invention.

Stringent conditions as used herein shall denote stringency as normally applied in connection with Southern blotting and hybridization as described e.g. by Southern E. M., 1975, J. Mol. Biol. 98:503-517. For such purposes it is routine practise to include steps of prehybridization and hybridization. Such steps are normally performed using solutions containing 6×SSPE, 5% Denhardt's, 0.5% SDS, 50% formamide, 100 □g/ml denatured salmon testis DNA (incubation for 18 hrs at 42° C.), followed by washings with 2×SSC and 0.5% SDS (at room temperature and at 37° C.), and a washing with 0.1×SSC and 0.5% SDS (incubation at 68° C. for 30 min), as described by Sambrook et al., 1989, in "Molecular Cloning/A Laboratory Manual", Cold Spring Harbor), which is incorporated herein by reference.

The DNA sequences are used in a variety of ways. They may be used as probes for identifying homologs of uHAse (e.g., homologs of huHAse). Mammalian homologs have substantial sequence similarity to one another, i.e. at least 75%, usually at least 90%, more usually at least 95% sequence identity. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. 1990 J Mol Biol 215:403-10.

Nucleic acids having sequence similarity are detected by hybridization under low stringency conditions, for example, at 50.degree. C. and 10.times.SSC (0.9 M saline/0.09 M sodium citrate) and remain bound when subjected to washing at 55.degree. C. in 1.times.SSC. Sequence identity may be determined by hybridization under high stringency conditions, for example, at 50.degree. C. or higher and 0.1.times.SSC (9 mM saline/0.9 mM sodium citrate). By using probes, particularly labeled probes of DNA sequences, one can isolate homologous or related genes. The source of homologous genes may be any species, e.g. Primate species, particularly human; rodents, such as rats and mice, canines, felines, bovine, opines, equine, yeast, Drosophila, Caenhorabditis, etc.

In a further embodiment there is provided a polynucleotide comprising a nucleotide sequence which is degenerate to a polynucleotide capable of hybridising to SEQ ID NO:1, or a fragment thereof.

Degeneracy as used herein is defined in terms of the activity or functionality associated with the polypeptide expressed from said degenerate polynucleotide, said polynucleotide is either i) comprising a proteolytic activity specific at least for Insulin Like Growth Factor Binding Protein 5 (IGFBP-5); and/or ii) recognised by an antibody, or a binding fragment thereof, which is capable of recognising a polypeptide having the amino acid sequence as shown in SEQ ID NO:2; and/or iii) competing with a polypeptide having the amino acid sequence as shown in SEQ ID NO:2 for binding to a cell surface receptor having an affinity for said polypeptide.

In a further embodiment there is provided a polynucleotide comprising the complementary strand of a polynucleotide according to the invention.

The polynucleotide according to the invention may be operably linked to a further polynucleotide comprising nucleic acid residues corresponding to the 3' untranslated region of PAPP-A2, or a fragment thereof. As used herein the 3' untranslated region comprises nucleic acid residues 5377 to 8527 of SEQ ID NO:1.

There is also provided a recombinant DNA molecule in the form of an expression vector comprising an expression signal operably linked to a polynucleotide according to the invention.

In a further embodiment there is provided a host organism transfected or transformed with the polynucleotide according to the invention, or the vector according to the invention. The host organism is preferably a mammalian organism such as e.g. a mammalian cell line. However, a microbial eukaryote such as yeast or fungi may also be used, as may a microbial prokaryote such as Bacillus or $E.\ coli$. The person skilled in the art will know how to select expression signals, including leader sequences and/or signal peptides suitable for expression in a given cell. The person skilled in the art will also know how to determine the level of expression in a given cell by using standard molecular biology techniques.

In a further aspect the invention relates to an isolated polypeptide comprising or essentially consisting of the amino acid sequence of SEQ ID NO:2, or a fragment thereof, wherein said fragment a) has a proteolytic activity specific at least for Insulin Like Growth Factor Binding Protein 5 (IGFBP-5); and/or
b) is recognised by an antibody, or a binding fragment thereof, which is capable of recognising a polypeptide having the amino acid sequence as shown in SEQ ID NO:2; and/or
c) competes with a polypeptide having the amino acid sequence as shown in SEQ ID NO:2 for binding to a cell surface receptor with an affinity for said polypeptide.

In one preferred embodiment of the invention there is also provided variants of SEQ ID NO:2, and variants of fragments thereof. Variants are determined on the basis of their degree of identity or their homology with a predetermined amino acid sequence, said predetermined amino acid sequence being SEQ ID NO:2, or, when the variant is a fragment, a fragment of SEQ ID NO:2.

Accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence.

Variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, His, Asn, Gln, Ser, Thr, Tyr, and Cys)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphor-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of an amino acid may be an addition or deletion of from 2 to 10 amino acids, such as from 10 to 20 amino acids, for example from 20 to 30 amino acids, such as from 40 to 50 amino acids. However, additions or deletions of more than 50 amino acids, such as additions from 10 to 100 amino acids, addition of 100 to 150 amino acids, addition of 150-250 amino acids, are also comprised within the present invention.

The polypeptide fragments according to the present invention, including any functional equivalents thereof, may in one embodiment comprise less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues.

"Functional equivalency" as used in the present invention is according to one preferred embodiment established by means of reference to the corresponding functionality of a predetermined fragment of the sequence. More specifically, functional equivalency is to be understood as the ability of a polypeptide fragment to exert IGFBP-5 specific protease activity and/or to be recognised by an antibody capable of recognising PAPP-A2 and/or to compete with PAPP-A2 for binding to a receptor having affinity for PAPP-A2.

Functional equivalents or variants of PAPP-A2 will be understood to exhibit amino acid sequences gradually differing from the preferred predetermined PAPP-A2 sequence, as the number and scope of insertions, deletions and substitutions including conservative substitutions increases. This difference is measured as a reduction in homology between the preferred predetermined sequence and the fragment or functional equivalent.

All fragments or functional equivalents of SEQ ID NO:2 are included within the scope of this invention, regardless of the degree of homology that they show to a preferred predetermined sequence of PAPP-A2 as reported herein. The reason for this is that some regions of PAPP-A2 are most likely readily mutatable, or capable of being completely deleted, without any significant effect on the binding activity of the resulting fragment.

A functional variant obtained by substitution may well exhibit some form or degree of native PAPP-A2 activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

The homology between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90.

Fragments sharing at least some homology with fragments of SEQ ID NO:2 are to be considered as falling within the scope of the present invention when they are at least about 90 percent homologous, for example at least 92 percent homologous, such as at least 94 percent homologous, such as at least 95 percent homologous, such as at least 96 percent homologous, for example at least 97 percent homologous, such as at least 98 percent homologous, for example at least 99 percent homologous with said fragments of SEQ ID NO:2. According to one embodiment of the invention the homology percentages refer to identity percentages.

Additional factors that may be taken into consideration when determining functional equivalence according to the meaning used herein are i) the ability of antisera to detect a PAPP-A2 fragment according to the present invention, or ii) the ability of the functionally equivalent PAPP-A2 fragment to compete with PAPP-A2 in a binding assay. One method of determining a sequence of immunogenically active amino acids within a known amino acid sequence has been described by Geysen in U.S. Pat. No. 5,595,915 and is incorporated herein by reference.

A further suitably adaptable method for determining structure and function relationships of peptide fragments is described by U.S. Pat. No. 6,013,478, which is herein incorporated by reference. Also, methods of assaying the binding of an amino acid sequence to a receptor moiety are known to the skilled artisan.

Conservative substitutions may be introduced in any position of a preferred predetermined fragment of SEQ ID NO:2, and it may also be desirable to introduce non-conservative substitutions in any one or more positions.

A non-conservative substitution leading to the formation of a functionally equivalent fragment of PAPP-A2 would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional comprising substituted amino acids having hydrophilic or hydropathic indices that are within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8);

tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other PAPP-A2 fragments and/or PAPP-A2 molecules, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are bifunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of PAPP-A2 according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-PAPP-A2 antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of PAPP-A2 can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the fragment of PAPP-A2 is synthesised by automated synthesis. Any of the commercially available solid-phase techniques may be employed, such as the Merrifield solid phase synthesis method, in which amino acids are sequentially added to a growing amino acid chain. (See Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of PAPP-A2 according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of PAPP-A2 according to the invention are also provided and fall under the scope of the invention. PAPP-A2 functional equivalents and variants can be produced as homodimers or heterodimers with other amino acid sequences or with native PAPP-A2 sequences. Heterodimers include dimers containing immunoreactive PAPP-A2 fragments as well as PAPP-A2 fragments that need not have or exert any biological activity.

PAPP-A2 fragments according to the invention may be synthesised both in vitro and in vivo. Method for in vitro synthesis are well known, and methods being suitable or suitably adaptable to the synthesis in vivo of PAPP-A2 are also described in the prior art. When synthesized in vivo, a host cell is transformed with vectors containing DNA encoding PAPP-A2 or a fragment thereof. A vector is defined as a replicable nucleic acid construct. Vectors are used to mediate expression of PAPP-A2. An expression vector is a replicable DNA construct in which a nucleic acid sequence encoding the predetermined PAPP-A2 fragment, or any functional equivalent thereof that can be expressed in vivo, is operably linked to suitable control sequences capable of effecting the expression of the fragment or equivalent in a suitable host. Such control sequences are well known in the art.

Cultures of cells derived from multicellular organisms represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and W138, BHK, COS-7, 293 and MDCK cell lines. Preferred host cells are eukaryotic cells known to synthesize endogenous PAPP-A2. Cultures of such host cells may be isolated and used as a source of the fragment, or used in therapeutic methods of treatment, including therapeutic methods aimed at promoting or inhibiting a growth state, or diagnostic methods carried out on the human or animal body.

In particular embodiments the present invention relates to a polypeptide fragment according to the invention, wherein the PAPP-A2 fragment comprises or essentially consists of amino acid residues 234 to 1791 corresponding to the mature part of PAPP-A2, including any processing variants thereof.

Processing variants are variants resulting from alternative processing events, possibly processing events catalysed by any protease including, but not limited to, a signal peptidase and a furin. One putative cleavage site is located after position 233 is described herein below in detail. Another putative cleavage site is located after the motif RQRR (position 196-199 in the amino acid sequence of PAPP-A2). Processing variants shall be understood to comprise variants arising from processing in vivo when PAPP-A2 is expressed in human or animal tissue, sera or body fluids.

Mature PAPP-A2 amino acids sequences essentially consisting of the mature sequence designated in SEQ ID NO:2 (amino acid residues 234 to 1791) shall be understood in one embodiment to comprise this part of the sequence lacking between 1 to about 10 N-terminal amino acids or C-terminal amino acids, preferably 1 to 10 N-terminal amino acids, such as 2 to 8 N-terminal acids, for example 3 to 6 N-terminal amino acids.

Also included in the definition of essentially consisting of as used herein shall be the mature sequence designated in SEQ ID NO:2 (amino acid residues 234 to 1791) having in addition thereto an additional 1 to about 10 N-terminal amino acids or C-terminal amino acids, preferably 1 to 10 N-terminal amino acids, such as 2 to 8 N-terminal acids, for example 3 to 6 N-terminal amino acids. This definition of essentially consisting of shall also apply in other aspects and is not restricted to being used in connection with a particular part of PAPP-A2. The definition shall also apply to other processes PAPP-A2 polypeptides including polypeptides arising from alternative processing in tissue, sera or body fluids other than the ones from where the processed PAPP-A2 has originally been isolated.

Additionally preferred fragments comprise or essentially consists of amino acid residues 1 to 233 corresponding to the prepro part of PAPP-A2, of amino acid residues 23 to 233 corresponding to the pro part of PAPP-A2, of amino acid residues 1 to 22 corresponding to the signal peptide or leader sequence of PAPP-A2, and to such sequences operably linked to the mature part of PAPP-A2 corresponding to amino acid residues 234 to 1791 of SEQ ID NO:2.

There is also provided recombinant PAPP-A2 polypeptide, or a fragment thereof, wherein preferably the polypeptide is free of human proteins, or other proteins natively associated with said polypeptide.

In a further aspect there is provided a composition comprising i) a polynucleotide according to the invention, and/or ii) a vector according to the invention, and/or iii) a host organism according to the invention, and/or iv) a polypeptide according to the invention, in combination with a physiologically acceptable carrier.

In yet another aspect there is provided a pharmaceutical composition comprising i) a polynucleotide according to the invention, and/or ii) a vector according to the invention, and/or iii) a host organism according to the invention, and/or iv) a polypeptide according to the invention, in combination with a pharmaceutically acceptable carrier.

The invention further pertains to a method for producing an antibody with specificity for a PAPP-A2 polypeptide according to the invention, or a fragment thereof, said method comprising the steps of
  i) providing a host organism,
  ii) immunizing the host organism with the polypeptide according to claim 10, and
  iii) obtaining said antibody.

There is also provided monoclonal antibodies and polyclonal antibodies having specific binding affinity for a PAPP-A2 polypeptide according to the invention, or a fragment thereof. The antibody is preferably a monoclonal.

In a further aspect there is provided a method for producing a PAPP-A2 polypeptide according to the invention, said method comprising the steps of
  i) providing a suitable host organism, preferably a mammalian cell,
  ii) transfecting or transforming the host organism provided in step i) with a polynucleotide according to the invention, or a vector according to the invention,
  iii) culturing the host organism obtained in step ii) under conditions suitable for expression of the polypeptide encoded by the polynucleotide or the vector; and optionally
  iv) isolating from the host organism the polypeptide resulting from recombinant expression by the host organism.

In a still further aspect of the invention there is provided a method for inhibiting and/or reducing the expression of PAPP-A2 in a cell by means of anti-sense technology, said method comprising the steps of
  i) providing an anti-sense polynucleotide according to the invention,
  ii) transfecting or transforming a cell capable of expressing PAPP-A2 with said anti-sense polynucleotide provided in step i),
  iii) culturing the cell obtained in step ii) under conditions suitable for hybridization of the polynucleotide provided in step i) to a complementary polynucleotide in said cell involved in the expression of PAPP-A2, and
  iv) inhibiting and/or reducing the expression of PAPP-A2 in said cell.

The antisense polynucleotide and the complementary polynucleotide may be co-expressed from distinct polynucleotide molecules or they may be expressed from the same molecule. As an alternative to hybridization, the method may include the use of reverse transcriptase PCR technology (rt PCT technology).

In yet another aspect of the invention there is provided a method for detecting PAPP-A2, or measuring the level of PAPP-A2, in a biological sample obtained from an individual, said method comprising the steps of
  i) obtaining a biological sample from said individual,
  ii) detecting PAPP-A2 in said sample by detecting
    a) a PAPP-A2 polypeptide, or a fragment thereof, and/or
    b) a polynucleotide in the form of mRNA originating from PAPP-A2 expression, and/or
    c) PAPP-A2 specific protease activity, preferably IGFBP-5 protease activity, or proteolytic activity directed against a derivative of IGFBP-5.

The method may comprise the further step of comparing the PAPP-A2 or the level of PAPP-A2 detected in step ii) with a predetermined value selected from the group consisting of
  a) a predetermined amount and/or concentration of PAPP-A2; and/or
  b) a predetermined amount and/or concentration of PAPP-A2 mRNA; and/or
  c) a predetermined PAPP-A2 specific protease activity.

The predetermined value in one embodiment will be indicative of a normal physiological condition of said individual.

The biological sample is preferably selected from the group consisting of blood, urine, pleural fluid, oral washings, tissue biopsies, and follicular fluid.

When the level of PAPP-A2 is measured as an amount of PAPP-A2 protein, the PAPP-A2 protein is preferably measured by immunochemical analysis wherein PAPP-A2 protein is detected by at least one monoclonal antibody. PAPP-A2 protein may also be detected in a complex comprising at least one additional component, preferably a polypeptide such as, but not limited to, pro-MBP (pro-Major-Basic Protein). PAPP-A2 may also be detected as a PAPP-A2 monomer or as a PAPP-A2 dimer.

Further aspects of the invention relates to a method of diagnosing a clinical condition in an individual, said method comprising the steps of
i) performing a method for detecting PAPP-A2 or measuring the level of PAPP-A2, and
ii) diagnosing the clinical condition.

The clinical condition is preferably a fetal abnormality such as, but not limited to, a fetal abnormality selected from the group consisting of Trisomy 21, Trisomy 18, Trisomy 13, and Open Spina Bifida.

Additional fetal abnormalities capable of being diagnosed according to the invention is ectopic pregnancy, open spina bifida, neural tube defects, ventral wall defects, Edwards Syndrome, Pateaus Syndrome, Turner Syndrome, Monosomy X or Kleinfelter's Syndrome.

In another aspect the clinical condition is an altered growth state selected from the group consisting of a growth promoting state and a growth inhibiting state, including, but not limited to, restenosis, atherosclerosis, wound healing, fibrosis, myocardial infarction, osteoporosis, rheumatoid arthritis, multiple myeloma, or cancer.

In a yet further aspect of the invention there is provided a method for detecting expression of a polynucleotide according to the invention in a biological sample, said method comprising the steps of
i) providing a biological sample putatively containing a polynucleotide according to the invention, and
ii) contacting the biological sample with a polynucleotide comprising a strand that is i) complementary to the polynucleotide according to the invention and ii) capable of hybridizing thereto, and
iii) allowing hybridization to occur, and
iv) detecting the hybridization complex obtained in step iii),
wherein the presence of the hybridization complex is indicative of the expression in the biological sample of the polynucleotide according to the invention, or a fragment thereof.

In a still further aspect of the invention there is provided a method for identifying an agent inhibiting the protease activity of PAPP-A2, said method comprising the steps of
i) incubating a) the polypeptide according to the invention, or a fragment thereof, and b) a predetermined substrate for said polypeptide or fragment, and c) a putative inhibitory agent, and
ii) determining if proteolysis of said substrate is inhibited.

The substrate preferably comprises a polypeptide that may be an internally quenched fluorescent peptide. One preferred substrate comprises or essentially consists of IGFBP-5, or a fragment thereof.

The invention also pertains to an inhibitory agent obtainable according to such a method for identifying an agent inhibiting the protease activity of PAPP-A2.

There is also provided the use of such provided inhibitory agents in the manufacture of a medicament for treating a clinical condition in an individual in need of such treatment.

In a still further aspect the invention pertains to a method for identifying an agent capable of enhancing the protease activity of PAPP-A2, said method comprising the steps of
i) incubating a) the polypeptide according to the invention, or a fragment thereof, and b) a predetermined substrate for said polypeptide, and c) a putative enhancer agent, and
ii) determining if proteolysis of said substrate is enhanced.

The substrate preferably comprises a polypeptide including an internally quenched fluorescent peptide. IGFBP-5, or a fragment thereof, is particularly preferred as a substrate.

There is also provided an enhancing agent obtainable according to the method for identifying an agent capable of enhancing the protease activity of PAPP-A2, and the invention also pertains to the use of such enhancing agents in the manufacture of a medicament for treating a clinical condition in an individual in need of such treatment.

In yet another aspect there is provided a method of treatment by therapy of an individual, said method comprising the step of administrating to said individual i) a pharmaceutical composition according to the invention, and/or ii) the inhibitory agent according to the invention, and/or the enhancing agent according to the invention.

In a still further aspect there is provided a method for purification of PAPP-A2 or complexes of PAPP-A2 with other proteins, said method comprising the steps of
i) providing a polyclonal or monoclonal antibody with specific binding affinity for a polypeptide according to the invention, or a fragment thereof, and
ii) purifying PAPP-A2, or a fragment thereof, by means of affinity chromatography.

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXAMPLES

Example 1

Identification of a Nucleotide Sequence Encoding PAPP-A2

Accession numbers (ANs) given in this text refer to sequences deposited in GenBank or other biological sequence databases. ANs are used interchangeable with the protein or nucleotide sequences deposited under the given AN.

Searching public nucleotide databases for DNA sequences with homology to PAPP-A ((Kristensen et al., 1994, *Biochemistry* 33, 1592-8), AN CAA48341) when translated into polypeptide sequence revealed two genomic clones with the ANs AL031734 and AL031290. Both originate from the human chromosome 1 (1q24). The search was performed against the "nr" collection of databases using the program tblastn at ncbi.nlm.nih.gov/BLAST/ with default settings. In this example, PAPP-A is numbered with the N-terminal Glu as residue 1, as in (Kristensen et al., 1994, *Biochemistry* 33, 1592-8). In the deposited sequence record (AN X68280) this Glu is residue 5.

The sequence reported in AL031734 contains 168835 base pairs. Two noncontiguous sequence stretches (nt. 103432-103566, and 140846-141919) of the total sequence together aligned with residues 16-59, and 59-413 of the PAPP-A polypeptide sequence when translated. The sequence reported in AL031290 contains 121780 base pairs. Four noncontiguous sequence stretches (nt. 10209-10358, 11752-11901, 20531-20463, and 60536-60652) of the total sequence together aligned with residues 1313-1362, 1376-1425, 1457-1479, and 1470-1506 of the PAPP-A polypeptide sequence when translated. The sequence stretches between the coding regions of both of the genomic sequences represent noncoding genomic DNA (introns) or coding regions that do not align.

Based on these findings, we hypothesized the existence of a novel protein, PAPP-A2, with homology to PAPP-A. It was then established the complete coding sequence of the regions of PAPP-A2 that were partially covered by the two genomic sequences reported in AL031734 and AL031290. We denote those contiguous sequences hom-N and hom-C, respectively (FIG. 2). But first, we established the existence of a coding cDNA sequence that also showed homology to PAPP-A, and that connected the sequence of hom-N and hom-C (FIG. 2). All essential primers used are described in Table 1. The entire cDNA sequence encoding the 1791-residue preproPAPP-A2 is shown in FIG. 1. Standard cloning techniques were used, and all DNA constructs were analyzed by sequencing. The methodology used is described below. The name PAPP-A2 is used for the protein encoded by this DNA sequence.

Cloning of a contiguous coding cDNA stretch corresponding to the midregion between hom-N and hom-C: To obtain the midregion (FIG. 2), cDNA was synthesized using human placental mRNA as a template and a primer, RT-N-mid, derived from AL031290 (Table 1, FIG. 2). This cDNA was used as a template in a PCR to obtain a cDNA corresponding to the midregion of the hypothesized PAPP-A2. PCR primers were PR-mid5 and PR-mid3 (Table 1, FIG. 2). The coding sequence of the midregion obtained corresponds to residues 665-1572 of FIG. 3 (SEQ ID NO:1), a total of 908 amino acids.

this finding, the cDNA used to obtain the midregion (placental mRNA primed with RT-N-mid, as detailed above) was used as a template in a PCR to obtain the contiguous cDNA of hom-N. PCR primers were: PR-N5 and PR-N3 (Table 1, FIG. 2).

Cloning of a contiguous coding cDNA stretch corresponding to the C-terminal end of PAPP-A2 (hom-C): Searching available databases (using the program blastn at ncbi.nlm.nih.gov/BLAST/with default settings) for human EST sequences matching the genomic sequence of AL031290 revealed an EST sequence overlapping with some of the coding regions of AL031290 already defined by the stretch nt. 60536-60652 (cf. above). Nt. 62790-62995 of AL031290 also matched the sequence of the human EST sequence AA368081 originating from placenta.

When translated into polypeptide sequence, this EST sequence showed homology to the C-terminal end of PAPP-A. Further, a stop codon was present within the coding sequence corresponding to amino acid 1537 of PAPP-A. That is, PAPP-A2 does not extend C-terminally beyond PAPP-A when the two sequences are aligned. Based on this, cDNA was synthesized using human placental mRNA as a template and a primer originating from AL031290 (Table 1). This

TABLE 1

Locations of primers used for reverse transcription or PCR.
The primers are listed in the order of their use.

| NAME | SOURCE[a] | Nt. NUMBERS[b] | SEQUENCE[c] |
|---|---|---|---|
| RT-N-mid: | AL031290 | 10262-10281, (4770-4789) | GCTCACACACCACAGGAATG* (SEQ ID NO: 4) |
| PR-mid5: | AL031734 | 141874-141894, (1947-1967) | GGCTGATGTGCGCAAGACCTG (SEQ ID NO: 5) |
| PR-mid3: | AL031290 | 10208-10229, (4716-4737) | GCATTGTATCTTCAGGAGCTTG* (SEQ ID NO: 6) |
| PR-N5: | AL031734 | 102606-102628, (−) | GAAGTTGACTTCTGGTTCTGTAG (SEQ ID NO: 7) |
| PR-N3: | — | —, (2380-2400) | CCCTGGGAAGCGAGTGAAGCC* (SEQ ID NO: 8) |
| RT-C: | AL031290 | 62982-63006, (−) | GCATTTCTTATAAGATCCTTCATGC* (SEQ ID NO: 9) |
| PR-C5: | — | —, (4180-4201) | GACAGCTGTCCGTCATTGCTGC (SEQ ID NO: 10) |
| PR-C3: | AL031290 | 62876-62897, (−) | CTTACTGCCTCTGAGGCAGTGG* (SEQ ID NO: 11) |

[a]Accession numbers of the relevant genomic clones are given. Primers PR-N3 and PR-C5 were located in the sequence connecting hom-N and hom-C, and are therefore not represented in the databases.
[b]Nucleotide numbers refer to the numbering of the sequences as reported in the file with the relevant accession number. In parentheses are given the corresponding numbers of SEQ ID NO: 1 (FIG. 1), except for primers PR-N5, RT-C and PR-C3, not within this sequence.
[c]Sequences are actual primer sequences (orientation 5'-to-3'). Sequences marked with an asterisk are complementary to the database sequences or the sequence given in FIG. 1.

Cloning of a contiguous coding cDNA stretch corresponding to the N-terminal end of PAPP-A2 (hom-N): Manual inspection of the genomic sequence AL031734 revealed that the open reading frame of the sequence stretch corresponding to PAPP-A residues 16-59 continued further in the 5' direction: Nt. 102646-103566 encodes a polypeptide sequence of 307 residues that starts with a methionine residue. Based on cDNA was used as a template in a PCR to obtain the contiguous cDNA of hom-C using PCR primers PR-C5 and PR-C3 (Table 1, FIG. 2).

All PCRs were carried out with Pfu polymerase (Stratagene). The three overlapping PAPP-A2 cDNA fragments (hom-N, the novel midregion, and hom-C) were all cloned into the vector pCR-BluntII-TOPO (Invitrogen). Several clones were sequenced in both orientations. The constructs are referred to as p2N, p2Mid, and p2C, respectively. The entire nucleotide sequence encoding PAPP-A2 is shown in FIG. 1 (and SEQ ID NO:1).

Example 2

Analyses of the Nucleotide and Amino Acid Sequence of PAPP-A2

Of the 1547 residues of mature PAPP-A, 708 residues (45.8%) are identical in preproPAPP-A2. There is no significant degree of identity between the prepro portion of PAPP-A and the remaining (N-terminal) portion of PAPP-A2 (FIG. 3). In this example, PAPP-A is numbered according to ((Haaning et al., 1996, *Eur J Biochem* 237, 159-63), AAC50543).

The sequence motifs recognized in PAPP-A (Kristensen et al., 1994, *Biochemistry* 33, 1592-8) are also present PAPP-A2: An elongated zinc binding consensus sequence, three lin-notch repeats (LNR1-3), and five short consensus repeats (SCR1-5) (FIG. 3). Further, all 82 cysteine residues of PAPP-A are conserved between the two proteins, and an additional 4 cysteines are present in the PAPP-A2 polypeptide sequence.

Example 3

Identification of Human EST Sequences Originating from the PAPP-A2 mRNA

A cluster of EST sequences matching the genomic sequence of AL031290 were identified around nt 64000-66000 of AL031290, starting approximately 1.2 kb from the end of the PAPP-A2 encoding sequence. The existence of mRNA connecting the coding region of PAPP-A2 and this cluster was verified in a PCR using primers from AL031290 (5'-GGAAAGAGCAGAGTTCACCCAT-3' (SEQ ID NO:12), nt. 64900-64879 of AL031290) and the PAPP-A2 encoding sequence (5'-CCGTCTTAGTCCACTGCATCC-3' (SEQ ID NO:13), nt. 20499-20519 of AL031290, nt 5171-5191 of AF311940), and oligo-dT primed placental cDNA as a template (Overgaard et al., 1999, *Biol Reprod* 61, 1083-9). As expected, the size of the resulting product was 2.2 kb, further demonstrating the existence of a PAPP-A2 mRNA with a 3'UTR of about 3 kb. The distribution among tissues is shown in Table 2.

TABLE 2

Expression of PAPP-A2 mRNA in human tissues evaluated by available EST sequences[a].

| Tissue of origin | Number of ESTs found |
| --- | --- |
| Human placenta | 38 |
| Pregnant uterus | 21 |
| Fetal liver/spleen | 11 |
| Kidney | 5 |
| Retina/Fetal retina | 3 |
| Corneal stroma | 2 |
| Fetal heart | 2 |
| Gessler Wilms tumor | 2 |
| Other tissues[b] | 14 |

[a]Using the blast algorithm (Altschul et al., 1997, *Nucleic Acids Res* 25, 3389-402), a total of 98 human EST sequences were identified that matched the 3'UTR of the PAPP-A2 mRNA sequence. The distribution among tissues is based on the annotations of individual database entries (not listed).
[b]EST sequences originated from pools of tissue, or from tissue represented by only one EST sequence.

Example 4

Expression in Mammalian Cells of Recombinant PAPP-A2 and Variants of PAPP-A2

The following plasmid constructs were made:
a) pPA2: The cDNA sequence of pre-pro-PAPP-A2 encoding amino acids 1-1791 in expression vector pcDNA3.1+.
b) pPA2-KO: As pPA2, but Glu-734 of the active site of PAPP-A2 substituted with a Gln residue (E734Q).
c) pPA2-mH: The expression vector pcDNA3.1/Myc-His (−)A containing the cDNA sequence of pre-pro-PAPP-A2 encoding amino acids 1-1791, not followed by a stop codon, but rather a c-myc and a His tag.
d) pPA2-KO-mH: As pPA2-mH, but with the E734Q substitution of pPA2-KO.

The three overlapping PAPP-A2 cDNA fragments (hom-N, the midregion, and hom-C) were used for the construction of a single contiguous cDNA sequence encoding PAPP-A2. The overlapping fragments were all contained in the vector pCR-BluntII-TOPO (Invitrogen) and referred to as p2N, p2Mid, and p2C, as detailed above (example 6.1). Clones of p2N and p2C were selected that had the proper orientation of the cDNA insert.

Construction of pPA2: The NotI-BamHI fragment was excised from p2C and cloned into pBluescriptIISK+ (Stratagene) to obtain p2CBlue. The NotI-SpeI fragment was excised from p2N, and the SpeI-BclI fragment was excised from p2Mid. Those two fragments were ligated into the NotI/BclI sites of p2CBlue in one reaction to obtain p2NMidCBlue, containing the entire PAPP-A2 cDNA. The NotI-ApaI fragment of pBluescriptIISK+ was excised and ligated into the NotI/ApaI sites of the mammalian expression vector pcDNA3.1+ (Invitrogen) to obtain a modified version of this vector, pcDNA-NA. The full length cDNA was then excised from p2NMidCBlue with NotI and XhoI and cloned into pcDNA-NA to obtain pPA2. All restriction sites used are in the multi cloning sites of the vectors, except for SpeI and BclI, both located in each of the two overlapping regions of the coding PAPP-A2 sequence stretches of p2N, p2Mid, and p2C (nt. 2365 and nt. 4203, respectively, of FIG. 3).

Construction of pPA2-KO: The construct pPA2-KO is a variant of the pPA2 expression construct in which residue Glu-734 of the active site of PAPP-A2 was substituted with a Gln residue. Thus, the mutant is E734Q. The pPA2-KO construct was made by site directed mutagenesis using the method of overlap extension PCR (Ho et al., 1989, *Gene* 77, 51-9) with pPA2 as the template. In brief, outer primers were 5'-CGCTCAGGGAAGGACAAGGG-3' (5' end primer, nt. 976-995 of SEQ ID NO:1) and 5'-CTAGAAGGCACAGTC-GAGGC-3' (SEQ ID NO:14) (3' end primer, nt. 1040-1021, sequence of vector pcDNA3.1+). Overlapping internal primers were 5'-TGTCCCACTTGATGGATCATGGTGTCG-GTGTGG-3' (SEQ ID NO:15) (nt. 2210-2178 of SEQ ID NO:1, nt. 2200 not C, but G resulting in E734Q) and 5'-CCATCAAGTGGGACATGTTCTGGGAC-3' (SEQ ID NO:16) (nt. 2196-2221 of SEQ ID NO:1, nt. 2200 not G, but C resulting in E734Q). The resulting mutated fragment was digested with XbaI and XhoI and swapped into pPA2 to generate pPA2-KO. All PCRs were carried out with Pfu DNA polymerase (Stratagene), and all constructs were verified by sequence analysis.

Construction of pPA2-mH: Two primers (5'-GAGGGCCT-GTGGACCCAGGAG-3', nt. 4906-4926 of SEQ ID NO:1, and 5'-GACGTAAAGCTTCTGATTTTCTTCTGC-CTTGG-3 (SEQ ID NO:17)', nt. 5373-5354 of SEQ ID NO:1, preceded by a HindIII site, AAGCTT, and nt. GACGTA to facilitate cleavage of the PCR product) were used in a PCR with pPA2 as the template to generate a nucleotide fragment encoding the C-terminal 156 residues of PAPP-A2 with the stop codon replaced by a HindIII site for in-frame ligation to expression vector. In brief, the PCR product was digested with EcoRI and HindIII and cloned into the EcoRI/HindIII sites of the vector pcDNA3.1/Myc-His(−)A to generate pPA2C-mH. The NotI-XbaI fragment (encoding the N-terminal portion of PAPP-A2), and the XbaI-EcoRI fragment (encoding the remaining central portion of PAPP-A2) were excised from pPA2 and ligated in one reaction into the NotI/EcoRI sites of pPA2C-mH. The resulting construct, pPA2-mH, encoded PAPP-A2 followed by residues KLGP (SEQ ID NO:18), the myc epitope (EQKLISEEDL (SEQ ID NO:19)), residues NSAVD (SEQ ID NO:20), and six H-residues (amino acids are given as one letter code). A stop codon follows immediately after the six histidine residues.

Construction of pPA2-KO-mH: A variant of pPA2-mH was constructed with residue Glu-734 substituted into a Gln residue: The NotI-KpnI fragment of pPA2-KO was excised and swapped into the NotI-KpnI sites of pPA2-mH, to generate pPA2-KO-mH.

Expression in mammalian cells: All constructs (pPA2, pPA2-KO, pPA2-mH, and pPA2-KO-mH) as well as empty expression vectors (pcDNA3.1+ and pcDNA3.1/Myc-His(−)A) were transiently transfected into mammalian cells for expression of recombinant PAPP-A2 protein. Briefly, human embryonic kidney 293T cells (293tsA1609neo) (DuBridge et al., 1987, *Mol Cell Biol* 7, 379-87) were maintained in high glucose DMEM medium supplemented with 10% fetal bovine serum, 2 mM glutamine, nonessential amino acids, and gentamicin (Life Technologies). Cells were plated onto 6 cm tissue culture dishes, and were transfected 18 h later by calcium phosphate coprecipitation (Pear et al., 1993, *Proc Natl Acad Sci USA* 90, 8392-6) using 10 µg of plasmid DNA prepared by QIAprep Spin Kit (Qiagen). After a further 48 h the supernatants were harvested, and replaced by serum-free medium (293 SFM II, Life Technologies) for another 48 h. The serum-free medium was harvested and cleared by centrifugation.

Analysis by Western blotting of recombinant protein resulting from transfection with the constructs pPA2-mH and pPA2-KO-mH, demonstrated that PAPP-A2 is secreted as a protein of 220 kDa (See FIG. 2). Reduction of disulfide bonds did not cause a visible change in band migration. Thus, in contrast to PAPP-A, PAPP-A2 is secreted as a monomer.

Example 5

Purification by Affinity Chromatography of Tagged PAPP-A2

Figure 4:
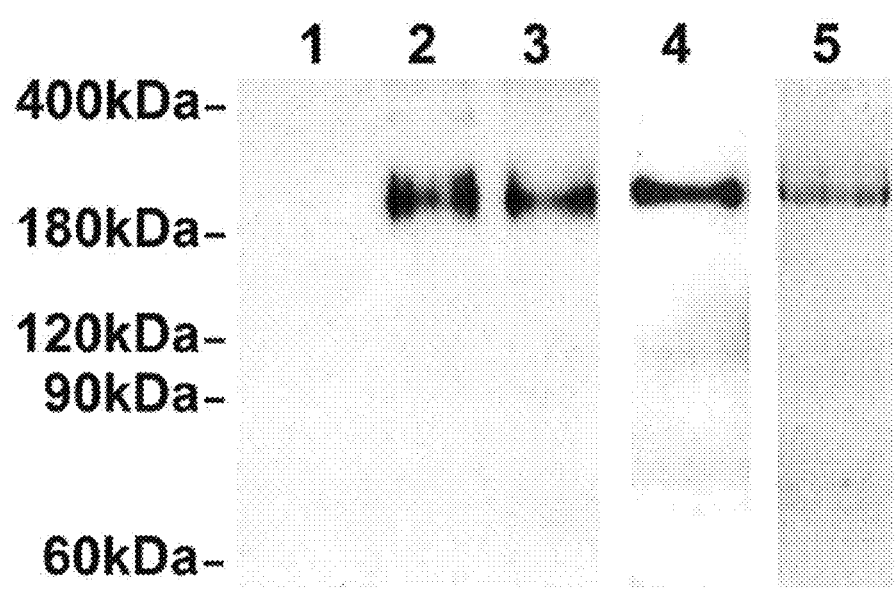
FIG. 4 shows PAPP-A2 by Western blotting and Coomassie staining. Medium from transfected 293T cells was Western blotted using monoclonal anti-c-myc. Lane 1, cells transfected with empty vector; lane 2, cells transfected with cDNA encoding wild-type PAPP-A2 C-terminally tagged with the c-myc peptide (pPA2-mH), non-reduced; lane 3, cells transfected with or cDNA encoding PAPP-A2 with an inactivating E734Q mutation (pPA2-KO-mH), non-reduced; lane 4, as lane 2, but reduced. Recombinant PAPP-A2 was purified by nickel affinity chromatography from serum free medium of cells transfected with pPA2-KO-mH, to eliminate possible autocatalysis (lane 5, reduced).

A metal chelate affinity column (2 ml, Pharmacia) was charged with nickel ions and loaded with serum-free medium (50 ml) from cells transiently transfected with pPA2-KO-mH (see example 6.4). After washing in PBS containing 1M NaCl, bound protein was eluted with 10 mM EDTA in PBS in fractions of 0.5 ml. PAPP-A2 containing fractions were located by SDS-PAGE (FIG. 4, lane 5). This protein was not seen from medium of cells transfected with empty vector (mock transfectants) and treated in a parallel manner.

Example 6

N-Terminal Sequence Analysis of PAPP-A2

C-terminally tagged PAPP-A2 purified from medium of cells transfected with construct pPA2-KO-mH (see examples 6.4 and 6.5) was reduced and run on a 10-20% SDS gel, and further blotted onto PVDF membrane (ProBlott, Applied Biosystems). Bands of 4 lanes were excised and subjected to N-terminal sequence analysis on an Applied Biosystems 477A sequencer equipped with an on-line HPLC (Sottrup-Jensen, 1995, *Anal Biochem* 225, 187-8). The N-terminal sequence observed at a level of approximately 20 pmol was: Ser-Pro-Pro-Glu-Glu-Ser-Asn (SPPEESN (residues 234-240 of SEQ ID NO:2)), resulting from cleavage before Ser-234 of the PAPP-A2 polypeptide after R(230)VKK (residues 230-233 of SEQ ID NO:2).

This confirms the prediction, that PAPP-A2, like PAPP-A, is synthesized as a prepro protein. The absence of an arginine residue in the P1 position, indicates that the proprotein processing enzyme responsible for this cleavage is not furin, but likely another proprotein convertase (Nakayama, 1997, *Biochem J* 327, 625-35). Cleavage of proPAPP-A2 might have been predicted after R(196)QRR, which archetypically marks furin cleavage (Nakayama, 1997, *Biochem J* 327, 625-35). We cannot exclude that cleavage occurred at this site, and that the observed N-terminus results from further processing.

Example 7

Cleavage of Insulin-Like Growth Factor Binding Protein (IGFBP)-5

Figure 5:
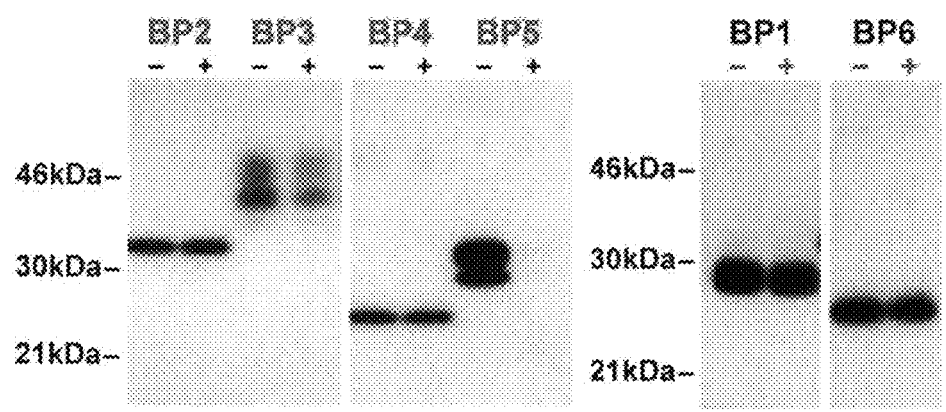
FIG. 5 shows the activity of PAPP-A2 against IGFBP-1-6. Medium from 293T cells transfected with empty vector (−), or cDNA encoding PAPP-A2 (pPA2) (+) was incubated with each of the six IGFBPs (BP1-BP6), and the activity was assessed by ligand blotting using radiolabeled IGF-II. Complete cleavage of IGFBP-5 is evident from the absence of a signal in the BP5+ lane. Partial degradation of IGFBP-3 is also evident.

Ligand blotting (Conover et al., 1993, *J Clin Invest* 91, 1129-37) with radiolabeled IGF-II (Bachem) was used to assay for activity against IGFBP-1 (from HepG2 conditioned medium), rIGFBP-2 (GroPep), rIGFBP-3 (gift of D. Powell), rIGFBP-4 (Austral), rIGFBP-5 (gift of D. Andress), and rIGFBP-6 (Austral). Of the six binding proteins, IGFBP-5 showed complete cleavage (FIG. 5). IGFBP-3 was partially degraded (FIG. 5). This cleavage was independent of the presence of IGF. Experiments were carried out with media from cells transfected with pPA2 or empty vector.

For further analysis, recombinant IGFBP-5 was produced in mammalian cells. In brief, human placental oligo-dT primed cDNA (Overgaard et al., 1999, *Biol Reprod* 61, 1083-9) was used as a template to amplify cDNA encoding human IGFBP-5 (Accession number M65062). Specific primers containing an XhoI site (5'-TCCG CTCGAGATGGTGTTGCTCACCGCGGT-3' (SEQ ID NO:21)) and a HindIII site (5'-CGAT AAGCTTCTCAACGTTGCTGCTGTCG-3' (SEQ ID NO:22)) were used, and the resulting PCR product was digested and cloned into the XhoI/HindIII sites of pcDNA3.1/Myc-His(−)A (Invitrogen). The construct encoded the full-length proIGFBP-5, immediately followed by residues KLGP, the myc epitope (EQKLISEEDL (SEQ ID NO:19)), residues NSAVD (SEQ ID NO:20), and six H-residues (amino acids are given as one letter code). The construct was verified by sequence analysis. Plasmid DNA for transfection was prepared by QIAprep Spin Kit (Qiagen). Cell culture and expression of recombinant IGFBP-5 was performed as described above in Example 6.4.

Figure 6:
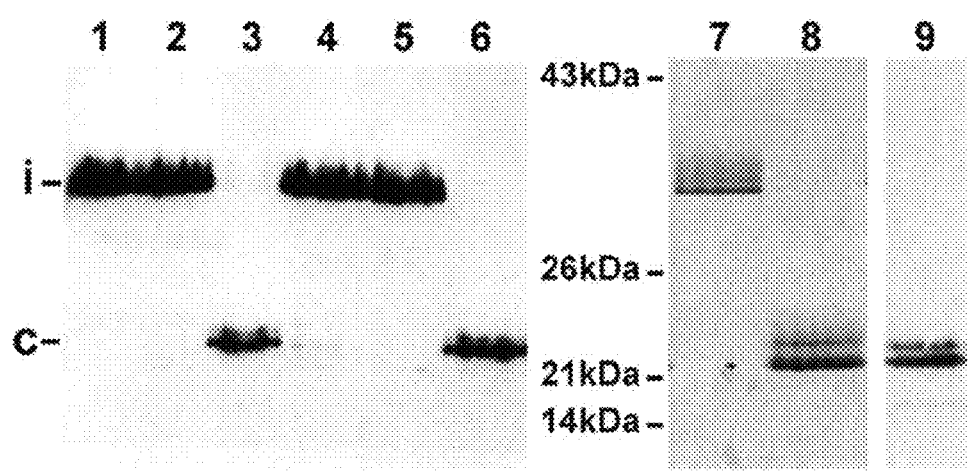
FIG. 6 shows proteolytic activity of PAPP-A2 against IGFBP-5. Medium from 293T cells transfected with empty vector (lane 1), cDNA encoding PAPP-A2 with an inactivating E734Q mutation (pPA2-KO) (lane 2), or cDNA encoding wild-type PAPP-A2 (pPA2) (lanes 3-6) was incubated with C-terminally c-myc tagged rIGFBP-5. Proteolytic activity was assessed by Western blotting using anti-c-myc. 'i' denotes intact rIGFBP-5; 'c' denotes the detectable C-terminal c-myc tagged cleavage product. In the absence of inhibitors, wild-type PAPP-A2 degraded all rIGFBP-5 (lane 3). The PAPP-A2 activity was abolished by 10 mM phenantroline (lane 4) and 5 mM EDTA (lane 5), but not affected by 100 µM 3,4-DCI (lane 6). Coomassie-stained SDS-PAGE of purified rIGFBP-5 is shown before (lane 7) and after (lane 8) digestion with purified PAPP-A2. A Western blot of the same digest, using anti-c-myc, is also shown (lane 9). Sequence analysis revealed that PAPP-A2 cleaves IGFBP-5 at one site, between Ser-142 and Lys-143.

Cleavage analysis was performed by Western blotting (FIG. 6). Briefly, recombinant IGFBP-5 as contained in 5 microL cell culture medium was incubated with culture supernatants (10 microL) from cells transfected with pPA2, pPA2-KO, or empty expression vectors (see example 6.4). Phosphate buffered saline was added to a final volume of 50 microL. After incubation at 37 degrees Celsius for 12 hours, 15 microL of the reaction mixture was separated by reducing 16% SDS-PAGE, blotted onto a PVDF membrane, and the C-terminal cleavage product was detected with monoclonal anti-c-myc (clone 9E19, ATTC) using peroxidase-conjugated secondary antibodies (P260, DAKO), and enhanced chemiluminescence (ECL, Amersham).

Example 8

Inhibition of the Activity of PAPP-A2

Various agents were analyzed for their ability to inhibit the proteolytic activity of PAPP-A2 against IGFBP-5. The experimental conditions were essentially as described in Example 6.7, except the agents to be tested were added (FIG. 6). Agents found to have no effect on the proteolytic activity of PAPP-A2 further included PMSF and aprotinin.

Example 9

Identification of the Cleavage Site in IGFBP-5

For cleavage site determination, purified rIGFBP-5 (FIG. 6, lane 7) was digested with purified PAPP-A2 and analyzed by SDS-PAGE (FIG. 6, lane 8). Edman degradation of blotted material showed that both distinct, visible degradation products (FIG. 6, lane 8) contained the N-terminal sequence K(144)FVGGA (SEQ ID NO:23) (IGFBP-5 is numbered with the N-terminal Leu of the mature protein as residue 1). The two bands both represent intact C-terminal cleavage fragments, because they also contain the C-terminal c-myc tag (FIG. 6, lane 9); they are likely to be differently glycosylated, in accordance with the heterogeneity of purified rIGFBP-5 (FIG. 6, lane 7). Both bands contained a second sequence at lower level (45%), L(1)GXFVH (SEQ ID NO:24), corresponding to the N-terminal sequence of IGFBP-5. The absence of Ser, expected in the third cycle, was taken as evidence for carbohydrate substitution of Ser-3. O-linked glycan on the N-terminal cleavage fragment is likely to cause it to smear around the two distinct, C-terminal fragments. Sequence analysis on the reaction mixture (>100 pmol) without SDS-PAGE separation showed only the same two IGFBP-5 sequences in equimolar amounts. Thus, PAPP-A2 cleaves IGFBP-5 at one site, between Ser-143 and Lys-144.

Example 10

Tissues where PAPP-A2 may Cause Proteolysis of IGFBP-5

Proteolyctic activity against IGFBP-5 has been widely reported from several sources, e.g. pregnancy serum (Claussen et al., 1994, *Endocrinology* 134, 1964-6), seminal plasma (Lee et al., 1994, *J Clin Endocrinol Metab* 79, 1367-72), culture media from smooth muscle cells (Imai et al., 1997, *J Clin Invest* 100, 2596-605), granulosa cells (Resnick et al., 1998, *Endocrinology* 139, 1249-57), osteosarcoma cells (Conover and Kiefer, 1993, *J Clin Endocrinol Metab* 76, 1153-9), and also from osteoblasts (Thrailkill et al., 1995, *Endocrinology* 136, 3527-33), and fibroblasts (Busby et al., 2000, *J Biol Chem*). In general, the proteinase responsible for cleavage of IGFBP-5 has remained unidentified.

The recent identification of PAPP-A as the IGFBP-4 proteinase in fibroblasts and osteoblasts (Lawrence et al., 1999, *Proc Natl Acad Sci USA* 96, 3149-53), ovarian follicular fluid (Conover et al., 1999, *J Clin Endocrinol Metab* 84, 4742-5), pregnancy serum (Overgaard et al., 2000, *J Biol Chem*), and vascular smooth muscle cells (Bayes-Genis, A., Schwartz, R. S., Ashai, K., Lewis, D. A., Overgaard, M. T., Christiansen, M., Oxvig, C., Holmes, D. R., Jr., and Conover, C. A. *Arterioscler. Thromb. Vasc. Biol.*, in press) firmly establishes PAPP-A and IGFBP-4 as an important functional pair in several systems. No other substrate as has been found for PAPP-A, and no other proteinase has been shown to cleave IGFBP-4 physiologically. It is therefore likely that the pair of PAPP-A2 and IGFBP-5 plays an analogous role in a number of the tissues mentioned above and/or elsewhere. Interestingly, incubating IGFBP-5 with smooth muscle cells conditioned medium resulted in cleavage between Ser-143 and Lys-144 (Imai et al., 1997, *J Clin Invest* 100, 2596-605), the same cleavage site as found here with PAPP-A2. This immediately suggests PAPP-A2 as an obvious candidate IGFBP-5 proteinase for this tissue.

CITED REFERENCES

Altschul, S. F., Madden, T. L., Schaffer, A. A., Zhang, J., Zhang, Z., Miller, W., and Lipman, D. J. (1997). Gapped BLAST and PSI-BLAST: a new generation of protein database search programs. Nucleic Acids Res 25, 3389-402.

Ausubel, F. M., Brent, R., Kingston, R. E., Moore, D. D., Seidman, J. G., Smith, J. A., and Struhl, K. (1989). Current Protocols in Molecular Biology (New York City, N.Y.: John Wiley & Sons).

Barker, R. L., Gleich, G. J., and Pease, L. R. (1988). Acidic precursor revealed in human eosinophil granule major basic protein cDNA [published erratum appears in J Exp Med 1989 Sep. 1; 170(3):1057]. J Exp Med 168, 1493-8.

Bayes-Genis, A., Schwartz, R. S., Ashai, K., A., L. D., Overgaard, M. T., Christiansen, M., Oxvig, C., Holmes Jr, D. R., and Conover, C. A. (2000). Insulin-like growth factor binding protein-4 protease produced by arterial smooth muscle cells in vitro is increased in the coronary artery following angioplasty. Arterioscler Thromb Vasc Biol, in press.

Biagiotti, R., Cariati, E., Brizzi, L., Cappelli, G., and D'Agata, A. (1998). Maternal serum screening for trisomy 18 in the first trimester of pregnancy. Prenat Diagn 18, 907-13.

Bischof, P. (1979). Purification and characterization of pregnancy associated plasma protein A (PAPP-A). Arch Gynecol 227, 315-26.

Bitter, G. A., Egan, K. M., Koski, R. A., Jones, M. O., Elliott, S. G., and Giffin, J. C. (1987). Expression and secretion vectors for yeast. Methods Enzymol 153, 516-44.

Bode, W., Gomis-Ruth, F. X., and Stockler, W. (1993). Astacins, serralysins, snake venom and matrix metalloproteinases exhibit identical zinc-binding environments (HEXXHXXGXXH and Met-turn) and topologies and should be grouped into a common family, the 'metzincins'. FEBS Lett 331, 134-40.

Bonno, M., Oxvig, C., Kephart, G. M., Wagner, J. M., Kristensen, T., Sottrup-Jensen, L., and Gleich, G. J. (1994). Localization of pregnancy-associated plasma protein-A and colocalization of pregnancy-associated plasma protein-A messenger ribonucleic acid and eosinophil granule major basic protein messenger ribonucleic acid in placenta. Lab Invest 71, 560-6.

Brambati, B., Macintosh, M. C., Teisner, B., Maguiness, S., Shrimanker, K., Lanzani, A., Bonacchi, I., Tului, L., Chard, T., and Grudzinskas, J. G. (1993). Low maternal serum levels of pregnancy associated plasma protein A (PAPP-A) in the first trimester in association with abnormal fetal karyotype. Br J Obstet Gynaecol 100, 324-6.

Broglie, R., Coruzzi, G., Fraley, R. T., Rogers, S. G., Horsch, R. B., Niedermeyer, J. G., Fink, C. L., and Chua, N. H. (1984). Light-regulated expression of a pea ribulose-1,5-

Busby, W. H., Jr., Nam, T. J., Moralez, A., Smith, C., Jennings, M., and Clemmons, D. R. (2000). The Complement Component C1s is the Protease That Accounts for Cleavage of Insulin-like Growth Factor Binding Protein-5 in Fibroblast Medium. J Biol Chem.

Christiansen, M., Oxvig, C., Wagner, J. M., Qin, Q. P., Nguyen, T. H., Overgaard, M. T., Larsen, S. O., Sottrup-Jensen, L., Gleich, G. J., and Norgaard-Pedersen, B. (1999). The proform of eosinophil major basic protein: a new maternal serum marker for Down syndrome. Prenat Diagn 19, 905-10.

Christiansen, M., Jaliashvili, I., Overgaard, M. T., Ensinger, C., Oxvig, C. (2000) Quantitation and characterization of pregnancy-associated complexes between angiotensinogen and the proform of eosinophil major basic protein in serum and amniotic fluid. Clin. Chem. 46, 1099-1105

Clackson, T., Hoogenboom, H. R., Griffiths, A. D., and Winter, G. (1991). Making antibody fragments using phage display libraries. Nature 352, 624-8.

Claussen, M., Zapf, J., and Braulke, T. (1994). Proteolysis of insulin-like growth factor binding protein-5 by pregnancy serum and amniotic fluid. Endocrinology 134, 1964-6.

Conover, C. A., and Kiefer, M. C. (1993). Regulation and biological effect of endogenous insulin-like growth factor binding protein-5 in human osteoblastic cells. J Clin Endocrinol Metab 76, 1153-9.

Conover, C. A., Kiefer, M. C., and Zapf, J. (1993). Posttranslational regulation of insulin-like growth factor binding protein-4 in normal and transformed human fibroblasts. Insulin-like growth factor dependence and biological studies. J Clin Invest 91, 1129-37.

Conover, C. A., Oxvig, C., Overgaard, M. T., Christiansen, M., and Giudice, L. C. (1999). Evidence that the insulin-like growth factor binding protein-4 protease in human ovarian follicular fluid is pregnancy associated plasma protein-A [In Process Citation]. J Clin Endocrinol Metab 84, 4742-5.

Crowther, J. R. (1995). ELISA. Theory and Practice, Methods in Molecular Biology. vol 42 (Totowa, N.J.: Humana Press).

DuBridge, R. B., Tang, P., Hsia, H. C., Leong, P. M., Miller, J. H., and Calos, M. P. (1987). Analysis of mutation in human cells by using an Epstein-Barr virus shuttle system. Mol Cell Biol 7, 379-87.

Folkersen, J., Grudzinskas, J. G., Hindersson, P., Teisner, B., and Westergaard, J. G. (1981). Pregnancy-associated plasma protein A: circulating levels during normal pregnancy. Am J Obstet Gynecol 139, 910-4.

Fowlkes, J. L. (1997). Insulinlike growth factor-binding protein proteolysis. An emerging paradigm in insulinlike growth factor physiology. Trends Endocrinol Metab 8, 299-306.

Gmunder, H., and Kohli, J. (1989). Cauliflower mosaic virus promoters direct efficient expression of a bacterial G418 resistance gene in Schizosaccharomyces pombe. Mol Gen Genet 220, 95-101.

Haddow, J. E., Palomaki, G. E., Knight, G. J., Williams, J., Miller, W. A., and Johnson, A. (1998). Screening of maternal serum for fetal Down's syndrome in the first trimester. N Engl J Med 338, 955-61.

Ho, S. N., Hunt, H. D., Horton, R. M., Pullen, J. K., and Pease, L. R. (1989). Site-directed mutagenesis by overlap extension using the polymerase chain reaction [see comments]. Gene 77, 51-9.

Hwa, V., Oh, Y., and Rosenfeld, R. G. (1999). The insulin-like growth factor-binding protein (IGFBP) superfamily. Endocr Rev 20, 761-87.

Haaning, J., Oxvig, C., Overgaard, M. T., Ebbesen, P., Kristensen, T., and Sottrup-Jensen, L. (1996). Complete cDNA sequence of the preproform of human pregnancy-associated plasma protein-A. Evidence for expression in the brain and induction by cAMP. Eur J Biochem 237, 159-63.

Imai, Y., Busby, W. H., Jr., Smith, C. E., Clarke, J. B., Garmong, A. J., Horwitz, G. D., Rees, C., and Clemmons, D. R. (1997). Protease-resistant form of insulin-like growth factor-binding protein 5 is an inhibitor of insulin-like growth factor-I actions on porcine smooth muscle cells in culture. J Clin Invest 100, 2596-605.

Kristensen, T., Oxvig, C., Sand, O., Moller, N. P., and Sottrup-Jensen, L. (1994). Amino acid sequence of human pregnancy-associated plasma protein-A derived from cloned cDNA. Biochemistry 33, 1592-8.

Lawrence, J. B., Oxvig, C., Overgaard, M. T., Sottrup-Jensen, L., Gleich, G. J., Hays, L. G., Yates, J. R., 3rd, and Conover, C. A. (1999). The insulin-like growth factor (IGF)-dependent IGF binding protein-4 protease secreted by human fibroblasts is pregnancy-associated plasma protein-A. Proc Natl Acad Sci USA 96, 3149-53.

Lee, K. O., Oh, Y., Giudice, L. C., Cohen, P., Peehl, D. M., and Rosenfeld, R. G. (1994). Identification of insulin-like growth factor-binding protein-3 (IGFBP-3) fragments and IGFBP-5 proteolytic activity in human seminal plasma: a comparison of normal and vasectomized patients. J Clin Endocrinol Metab 79, 1367-72.

Lin, T. M., Galbert, S. P., Kiefer, D., Spellacy, W. N., and Gall, S. (1974). Characterization of four human pregnancy-associated plasma proteins. Am J Obstet Gynecol 118, 223-36.

Logan, J., and Shenk, T. (1984). Adenovirus tripartite leader sequence enhances translation of mRNAs late after infection. Proc Natl Acad Sci USA 81, 3655-9.

Mackett, M., Smith, G. L., and Moss, B. (1982). Vaccinia virus: a selectable eukaryotic cloning and expression vector. Proc Natl Acad Sci USA 79, 7415-9.

Marks, J. D., Hoogenboom, H. R., Bonnert, T. P., McCafferty, J., Griffiths, A. D., and Winter, G. (1991). By-passing immunization. Human antibodies from V-gene libraries displayed on phage. J Mol Biol 222, 581-97.

Matthews, D. J., and Wells, J. A. (1993). Substrate phage: selection of protease substrates by monovalent phage display. Science 260, 1113-7.

McGrogan, M., Simonsen, C., Scott, R., Griffith, J., Ellis, N., Kennedy, J., Campanelli, D., Nathan, C., and Gabay, J. (1988). Isolation of a complementary DNA clone encoding a precursor to human eosinophil major basic protein. J Exp Med 168, 2295-308.

Meldal, M. (1998). Intramolecular fluorescence-quenched substrate libraries. Methods Mol Biol 87, 65-74.

Meldal, M. (1998). Introduction to combinatorial solid-phase assays for enzyme activity and inhibition. Methods Mol Biol 87, 51-7.

Meldal, M. (1998). The solid-phase enzyme inhibitor library assay. Methods Mol Biol 87, 75-82.

Nakayama, K. (1997). Furin: a mammalian subtilisin/Kex2p-like endoprotease involved in processing of a wide variety of precursor proteins. Biochem J 327, 625-35.

Nielsen, H., Engelbrecht, J., Brunak, S., and von Heijne, G. (1997). Identification of prokaryotic and eukaryotic signal peptides and prediction of their cleavage sites. Protein Eng 10, 1-6.

Overgaard, M. T., Haaning, J., Boldt, H. B., Olsen, I. M., Laursen, L., Christiansen, M., Gleich, G. J., Sottrup-Jensen, L., Conover, C. A., and Oxvig, C. (2000). Expression of Recombinant Human Pregnancy-Associated Plasma Protein-A and Identification of the Proform of Eosinophil Major Basic Protein as its Physiological Inhibitor. J Biol Chem.

Overgaard, M. T., Oxvig, C., Christiansen, M., Lawrence, J. B., Conover, C. A., Gleich, G. J., Sottrup-Jensen, L., and Haaning, J. (1999). Messenger ribonucleic acid levels of pregnancy-associated plasma protein-A and the proform of eosinophil major basic protein: expression in human reproductive and nonreproductive tissues. Biol Reprod 61, 1083-9.

Oxvig, C., Haaning, J., Hojrup, P., and Sottrup-Jensen, L. (1994). Location and nature of carbohydrate groups in proform of human major basic protein isolated from pregnancy serum. Biochem Mol Biol Int 33, 329-36.

Oxvig, C., Haaning, J., Kristensen, L., Wagner, J. M., Rubin, I., Stigbrand, T., Gleich, G. J., and Sottrup-Jensen, L. (1995). Identification of angiotensinogen and complement C3dg as novel proteins binding the proform of eosinophil major basic protein in human pregnancy serum and plasma. J Biol Chem 270, 13645-51.

Oxvig, C., Sand, O., Kristensen, T., Gleich, G. J., and Sottrup-Jensen, L. (1993). Circulating human pregnancy-associated plasma protein-A is disulfide-bridged to the proform of eosinophil major basic protein. J Biol Chem 268, 12243-6.

Oxvig, C., Sand, O., Kristensen, T., Kristensen, L., and Sottrup-Jensen, L. (1994). Isolation and characterization of circulating complex between human pregnancy-associated plasma protein-A and proform of eosinophil major basic protein. Biochim Biophys Acta 1201, 415-23.

Pear, W. S., Nolan, G. P., Scott, M. L., and Baltimore, D. (1993). Production of high-titer helper-free retroviruses by transient transfection. Proc Natl Acad Sci USA 90, 8392-6.

Peters, J. H., and Baumgarten, H. (1992). Monoclonal Antibodies (Offersheim, Germany: Springer-Verlag).

Rajaram, S., Baylink, D. J., and Mohan, S. (1997). Insulin-like growth factor-binding proteins in serum and other biological fluids: regulation and functions. Endocr Rev 18, 801-31.

Resnick, C. E., Fielder, P. J., Rosenfeld, R. G., and Adashi, E. Y. (1998). Characterization and hormonal regulation of a rat ovarian insulin-like growth factor binding protein-5 endopeptidase: an FSH-inducible granulosa cell-derived metalloprotease. Endocrinology 139, 1249-57.

Rosenfeld, S. A. (1999). Use of Pichia pastoris for expression of recombinant proteins. Methods Enzymol 306, 154-69.

Ruther, U., and Muller-Hill, B. (1983). Easy identification of cDNA clones. Embo J 2, 1791-4.

Sambrook, J., Fritsch, E. F., and Maniatis, T. (1989). Molecular Cloning. A Laboratory Manual (Cold Spring Harbor, N.Y.: Cold Spring Harbor Laboratory Press).

Scopes, R. K. (1987). Protein Purification. Principles and Practice. (Harrisonburg, Va.: Springer-Verlag).

Sinosich, M. J. (1990). Molecular characterization of pregnancy-associated plasma protein-A by electrophoresis. Electrophoresis 11, 70-8.

Smith, G. E., Summers, M. D., and Fraser, M. J. (1983). Production of human beta interferon in insect cells infected with a baculovirus expression vector. Mol Cell Biol 3, 2156-65.

Sottrup-Jensen, L. (1993). Determination of halfcystine in proteins as cysteine from reducing hydrolyzates. Biochem Mol Biol Int 30, 789-94.

Sottrup-Jensen, L. (1995). A low-pH reverse-phase high-performance liquid chromatography system for analysis of the phenylthiohydantoins of S-carboxymethylcysteine and S-carboxyamidomethylcysteine. Anal Biochem 225, 187-8.

Spencer, K., Ong, C., Skentou, H., A, W. L., and K, H. N. (2000). Screening for trisomy 13 by fetal nuchal translucency and maternal serum free beta-hCG and PAPP-A at 10-14 weeks of gestation. Prenat Diagn 20, 411-6.

Stocker, W., Grams, F., Baumann, U., Reinemer, P., Gomis-Ruth, F. X., McKay, D. B., and Bode, W. (1995). The metzincins—topological and sequential relations between the astacins, adamalysins, serralysins, and matrixins (collagenases) define a superfamily of zinc-peptidases. Protein Sci 4, 823-40.

Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res 22, 4673-80.

Thrailkill, K. M., Quarles, L. D., Nagase, H., Suzuki, K., Serra, D. M., and Fowlkes, J. L. (1995). Characterization of insulin-like growth factor-binding protein 5-degrading proteases produced throughout murine osteoblast differentiation. Endocrinology 136, 3527-33.

Wald, N., Stone, R., Cuckle, H. S., Grudzinskas, J. G., Barkai, G., Brambati, B., Teisner, B., and Fuhrmann, W. (1992). First trimester concentrations of pregnancy associated plasma protein A and placental protein 14 in Down's syndrome [see comments]. Bmj 305, 28.

Wald, N. J., Watt, H. C., and Hackshaw, A. K. (1999). Integrated screening for Down's syndrome on the basis of tests performed during the first and second trimesters [see comments]. N Engl J Med 341, 461-7.

Walsh, P. S., Erlich, H. A., and Higuchi, R. (1992). Preferential PCR amplification of alleles: mechanisms and solutions. PCR Methods Appl 1, 241-50.

Westergaard, J. G., Chemnitz, J., Teisner, B., Poulsen, H. K., Ipsen, L., Beck, B., and Grudzinskas, J. G. (1983). Pregnancy-associated plasma protein A: a possible marker in the classification and prenatal diagnosis of Cornelia de Lange syndrome. Prenat Diagn 3, 225-32.

That which is claimed is:

1. A cDNA that encodes a polypeptide that
   (a) consists of amino acid residues 234-1791 of SEQ ID NO: 2 (mature pregnancy associated plasma protein A2 (PAPP-A2)); or
   (b) is at least 95% sequence identical to the polypeptide of (a), and differs from the polypeptide of (a) solely by
      (i) deletion of 1-10 amino acid residues from, or addition of 1-10 residues to, the amino terminal, and/or
      (ii) deletion of 1-10 amino acid residues from, or addition of 1-10 residues to, the carboxy terminal, and/or
      (iii) one or more conservative substitutions;
   wherein said polypeptide has a proteolytic activity against Insulin Like Growth Factor Binding Protein 5 (IGFBP-5).

2. The cDNA of claim 1, wherein the cDNA encodes the polypeptide according to (a).

3. The cDNA of claim 1, wherein the cDNA encodes the polypeptide according to (b).

4. The cDNA of claim 3, wherein the amino acid sequence of said polypeptide according to (b) differs from that of the polypeptide according to (a) solely by one or more conservative substitutions.

5. An isolated polynucleotide comprising nucleotides 1-5376 of SEQ ID NO: 1.

6. An isolated polynucleotide comprising the cDNA of claim 1 operably linked to a polynucleotide encoding
   (a) an immunogenic carrier protein, and/or
   (b) a tag that facilitates the detection or purification of the polypeptide encoded by said isolated polynucleotide.

7. The cDNA of claim 1, 2, 3, 4 or 6 or the polynucleotide of claim 5, wherein the cDNA or the polynucleotide is operably linked to a further polynucleotide comprising nucleotides 5377 to 8527 of SEQ ID NO: 1, corresponding to a 3' untranslated region.

8. An isolated polynucleotide encoding a polypeptide that
   (a) consists of amino acid residues 234-1791 of SEQ ID NO: 2 (mature pregnancy associated plasma protein A2 (PAPP-A2)); or
   (b) is at least 95% sequence identical to the polypeptide of (a), and differs from the polypeptide of (a) solely by
      (i) deletion of 1-10 amino acid residues from, or addition of 1-10 residues to, the amino terminal, and/or
      (ii) deletion of 1-10 amino acid residues from, or addition of 1-10 residues to, the carboxy terminal, and/or
      (iii) one or more conservative substitutions;
   wherein said polypeptide has a proteolytic activity against Insulin Like Growth Factor Binding Protein 5 (IGFBP-5), and wherein said polynucleotide is operably linked to a polynucleotide having the sequence of nucleotides 5377-8527 of SEQ ID NO: 1.

9. An expression vector comprising the sequence of a polynucleotide encoding a polypeptide that
   (a) consists of amino acid residues 234-1791 of SEQ ID NO:2 (mature pregnancy associated plasma protein A2 (PAPP-A2)); or
   (b) is at least 95% sequence identical to the polypeptide of (a), and differs from the polypeptide of (a) solely by
      (i) deletion of 1-10 residues from, or addition of 1-10 residues to, the amino terminal, and/or
      (ii) deletion of 1-10 residues from, or addition of 1-10 residues to, the carboxy terminal, and/or
      (iii) one or more conservative substitutions;
   wherein said polypeptide has a proteolytic activity against Insulin Like Growth Factor Binding Protein 5 (IGFBP-5).

10. An isolated host cell comprising the vector of claim 9.

11. A method for expression of a polynucleotide in a recombinant host cell, the polynucleotide encoding a polypeptide that (A) consists of amino acid residues 234-1791 of SEQ ID NO: 2 (mature pregnancy associated plasma protein A2 (PAPP-A2)); or
(B) is at least 95% sequence identical to the polypeptide of (A), and differs from the polypeptide of (A) solely by
  (i) deletion of 1-10 amino acid residues from, or addition of 1-10 residues to, the amino terminal, and/or
  (ii) deletion of 1-10 amino acid residues from, or addition of 1-10 residues to, the carboxy terminal, and/or
  (iii) one or more conservative substitutions;
wherein said polypeptide has a proteolytic activity against Insulin Like Growth Factor Binding Protein 5 (IGFBP-5), the method comprising the steps of
(a) providing said polynucleotide, an expression vector, and a recombinant host cell,
(b) cloning the polynucleotide into the expression vector,
(c) transforming the recombinant host cell with the expression vector obtained in (b), and
(d) expressing the polypeptide in the recombinant host cell obtained in (c).

* * * * *

SEQUENCE LISTING

<160> NUMBER OF SEQ ID NOS: 26

<210> SEQ ID NO 1
<211> LENGTH: 8527
<212> TYPE: DNA
<213> ORGANISM: Homo sapiens
<220> FEATURE:
<221> NAME/KEY: CDS
<222> LOCATION: (1)..(5373)

```
<223> OTHER INFORMATION: prepro-PAPP-A2 coding sequence
<220> FEATURE:
<221> NAME/KEY: 3'UTR
<222> LOCATION: (5377)..(8527)
<223> OTHER INFORMATION:
<220> FEATURE:
<221> NAME/KEY: mat_peptide
<222> LOCATION: (700)..()
<223> OTHER INFORMATION:
<220> FEATURE:
<221> NAME/KEY: sig_peptide
<222> LOCATION: (1)..(66)
<223> OTHER INFORMATION:
<220> FEATURE:
<221> NAME/KEY: misc_feature
<222> LOCATION: (1)..(66)
<223> OTHER INFORMATION: prepro part of PAPP-A2
<220> FEATURE:
<221> NAME/KEY: misc_feature
<222> LOCATION: (67)..(699)
<223> OTHER INFORMATION: pro part of PAPP-A2

<400> SEQUENCE: 1 atg atg tgc tta  aag atc cta aga  ata agc ctg gcg  att ttg gct         45
Met Met Cys Leu  Lys Ile Leu Arg  Ile Ser Leu Ala  Ile Leu Ala
         -230                -225                -220 ggg tgg gca ctc  tgt tct gcc aac  tct gag ctg ggc  tgg aca cgc         90
Gly Trp Ala Leu  Cys Ser Ala Asn  Ser Glu Leu Gly  Trp Thr Arg
         -215                -210                -205 aag aaa tcc ttg  gtt gag agg gaa  cac ctg aat cag  gtg ctg ttg        135
Lys Lys Ser Leu  Val Glu Arg Glu  His Leu Asn Gln  Val Leu Leu
         -200                -195                -190 gaa gga gaa cgt  tgt tgg ctg ggg  gcc aag gtt cga  aga ccc aga        180
Glu Gly Glu Arg  Cys Trp Leu Gly  Ala Lys Val Arg  Arg Pro Arg
         -185                -180                -175 gct tct cca cag  cat cac ctc ttt  gga gtc tac ccc  agc agg gct        225
Ala Ser Pro Gln  His His Leu Phe  Gly Val Tyr Pro  Ser Arg Ala
         -170                -165                -160 ggg aac tac cta  agg ccc tac ccc  gtg ggg gag caa  gaa atc cat        270
Gly Asn Tyr Leu  Arg Pro Tyr Pro  Val Gly Glu Gln  Glu Ile His
         -155                -150                -145 cat aca gga cgc  agc aaa cca gac  act gaa gga aat  gct gtg agc        315
His Thr Gly Arg  Ser Lys Pro Asp  Thr Glu Gly Asn  Ala Val Ser
         -140                -135                -130 ctt gtt ccc cca  gac ctg act gaa  aat cca gca gga  ctg agg ggt        360
Leu Val Pro Pro  Asp Leu Thr Glu  Asn Pro Ala Gly  Leu Arg Gly
         -125                -120                -115 gca gtt gaa gag  ccg gct gcc cca  tgg gta ggg gat  agt cct att        405
Ala Val Glu Glu  Pro Ala Ala Pro  Trp Val Gly Asp  Ser Pro Ile
         -110                -105                -100 ggg caa tct gag  ctg ctg gga gat  gat gac gct tat  ctc ggc aat caa    453
Gly Gln Ser Glu  Leu Leu Gly Asp  Asp Asp Ala Tyr  Leu Gly Asn Gln
          -95                 -90                 -85 aga tcc aag gag  tct cta ggt gag  gcc ggg att cag  aaa ggc tca gcc    501
Arg Ser Lys Glu  Ser Leu Gly Glu  Ala Gly Ile Gln  Lys Gly Ser Ala
          -80                 -75                 -70 atg gct gcc act  act acc acc gcc  att ttc aca acc  ctg aac gaa ccc    549
Met Ala Ala Thr  Thr Thr Thr Ala  Ile Phe Thr Thr  Leu Asn Glu Pro
          -65                 -60                 -55 aaa cca gag acc  caa agg agg ggc  tgg gcc aag tcc  agg cag cgt cgc    597
Lys Pro Glu Thr  Gln Arg Arg Gly  Trp Ala Lys Ser  Arg Gln Arg Arg
-50                  -45                 -40                 -35 caa gtg tgg aag  agg cgg gcg gaa  gat ggg cag gga  gac tcc ggt atc    645
Gln Val Trp Lys  Arg Arg Ala Glu  Asp Gly Gln Gly  Asp Ser Gly Ile
          -30                 -25                 -20
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tct | tca | cat | ttc | caa | cct | tgg | ccc | aag | cat | tcc | ctt | aaa | cac | agg | gtc | 693  |
| Ser | Ser | His | Phe | Gln | Pro | Trp | Pro | Lys | His | Ser | Leu | Lys | His | Arg | Val |      |
|     |     | -15 |     |     |     | -10 |     |     |     |     |     | -5  |     |     |     |      |
| aaa | aag | agt | cca | ccg | gag | gaa | agc | aac | caa | aat | ggt | gga | gag | ggc | tcc | 741  |
| Lys | Lys | Ser | Pro | Pro | Glu | Glu | Ser | Asn | Gln | Asn | Gly | Gly | Glu | Gly | Ser |      |
|     | -1  | 1   |     |     |     | 5   |     |     |     |     | 10  |     |     |     |     |      |
| tac | cga | gaa | gca | gag | acc | ttt | aac | tcc | caa | gta | gga | ctg | ccc | atc | tta | 789  |
| Tyr | Arg | Glu | Ala | Glu | Thr | Phe | Asn | Ser | Gln | Val | Gly | Leu | Pro | Ile | Leu |      |
| 15  |     |     |     | 20  |     |     |     | 25  |     |     |     | 30  |     |     |     |      |
| tac | ttc | tct | ggg | agg | cgg | gag | cgg | ctg | ctg | ctg | cgt | cca | gaa | gtg | ctg | 837  |
| Tyr | Phe | Ser | Gly | Arg | Arg | Glu | Arg | Leu | Leu | Leu | Arg | Pro | Glu | Val | Leu |      |
|     |     |     | 35  |     |     |     | 40  |     |     |     | 45  |     |     |     |     |      |
| gct | gag | att | ccc | cgg | gag | gcg | ttc | aca | gtg | gaa | gcc | tgg | gtt | aaa | ccg | 885  |
| Ala | Glu | Ile | Pro | Arg | Glu | Ala | Phe | Thr | Val | Glu | Ala | Trp | Val | Lys | Pro |      |
|     |     | 50  |     |     |     | 55  |     |     |     | 60  |     |     |     |     |     |      |
| gag | gga | gga | cag | aac | aac | cca | gcc | atc | atc | gca | ggt | gtg | ttt | gat | aac | 933  |
| Glu | Gly | Gly | Gln | Asn | Asn | Pro | Ala | Ile | Ile | Ala | Gly | Val | Phe | Asp | Asn |      |
|     | 65  |     |     |     | 70  |     |     |     | 75  |     |     |     |     |     |     |      |
| tgc | tcc | cac | act | gtc | agt | gac | aaa | ggc | tgg | gcc | ctg | ggg | atc | cgc | tca | 981  |
| Cys | Ser | His | Thr | Val | Ser | Asp | Lys | Gly | Trp | Ala | Leu | Gly | Ile | Arg | Ser |      |
| 80  |     |     |     | 85  |     |     |     | 90  |     |     |     |     |     |     |     |      |
| ggg | aag | gac | aag | gga | aag | cgg | gat | gct | cgc | ttc | ttc | ttc | tcc | ctc | tgc | 1029 |
| Gly | Lys | Asp | Lys | Gly | Lys | Arg | Asp | Ala | Arg | Phe | Phe | Phe | Ser | Leu | Cys |      |
| 95  |     |     |     | 100 |     |     |     | 105 |     |     |     |     |     |     | 110 |      |
| acc | gac | cgc | gtg | aag | aaa | gcc | acc | atc | ttg | att | agc | cac | agt | cgc | tac | 1077 |
| Thr | Asp | Arg | Val | Lys | Lys | Ala | Thr | Ile | Leu | Ile | Ser | His | Ser | Arg | Tyr |      |
|     |     |     |     | 115 |     |     |     | 120 |     |     |     | 125 |     |     |     |      |
| caa | cca | ggc | aca | tgg | acc | cat | gtg | gca | gcc | act | tac | gat | gga | cgg | cac | 1125 |
| Gln | Pro | Gly | Thr | Trp | Thr | His | Val | Ala | Ala | Thr | Tyr | Asp | Gly | Arg | His |      |
|     |     | 130 |     |     |     | 135 |     |     |     | 140 |     |     |     |     |     |      |
| atg | gcc | ctg | tat | gtg | gat | ggc | act | cag | gtg | gct | agc | agt | cta | gac | cag | 1173 |
| Met | Ala | Leu | Tyr | Val | Asp | Gly | Thr | Gln | Val | Ala | Ser | Ser | Leu | Asp | Gln |      |
|     |     | 145 |     |     |     | 150 |     |     |     | 155 |     |     |     |     |     |      |
| tct | ggt | ccc | ctg | aac | agc | ccc | ttc | atg | gca | tct | tgc | cgc | tct | ttg | ctc | 1221 |
| Ser | Gly | Pro | Leu | Asn | Ser | Pro | Phe | Met | Ala | Ser | Cys | Arg | Ser | Leu | Leu |      |
|     | 160 |     |     |     | 165 |     |     |     | 170 |     |     |     |     |     |     |      |
| ctg | ggg | gga | gac | agc | tct | gag | gat | ggg | cac | tat | ttc | cgt | gga | cac | ctg | 1269 |
| Leu | Gly | Gly | Asp | Ser | Ser | Glu | Asp | Gly | His | Tyr | Phe | Arg | Gly | His | Leu |      |
| 175 |     |     |     | 180 |     |     |     | 185 |     |     |     |     |     |     | 190 |      |
| ggc | aca | ctg | gtt | ttc | tgg | tcg | acc | gcc | ctg | cca | caa | agc | cat | ttt | cag | 1317 |
| Gly | Thr | Leu | Val | Phe | Trp | Ser | Thr | Ala | Leu | Pro | Gln | Ser | His | Phe | Gln |      |
|     |     |     | 195 |     |     |     | 200 |     |     |     | 205 |     |     |     |     |      |
| cac | agt | tct | cag | cat | tca | agt | ggg | gag | gag | gaa | gcg | act | gac | ttg | gtc | 1365 |
| His | Ser | Ser | Gln | His | Ser | Ser | Gly | Glu | Glu | Glu | Ala | Thr | Asp | Leu | Val |      |
|     |     | 210 |     |     |     | 215 |     |     |     | 220 |     |     |     |     |     |      |
| ctg | aca | gcg | agc | ttt | gag | cct | gtg | aac | aca | gag | tgg | gtt | ccc | ttt | aga | 1413 |
| Leu | Thr | Ala | Ser | Phe | Glu | Pro | Val | Asn | Thr | Glu | Trp | Val | Pro | Phe | Arg |      |
|     |     | 225 |     |     |     | 230 |     |     |     | 235 |     |     |     |     |     |      |
| gat | gag | aag | tac | cca | cga | ctt | gag | gtt | ctc | cag | ggc | ttt | gag | cca | gag | 1461 |
| Asp | Glu | Lys | Tyr | Pro | Arg | Leu | Glu | Val | Leu | Gln | Gly | Phe | Glu | Pro | Glu |      |
|     | 240 |     |     |     | 245 |     |     |     | 250 |     |     |     |     |     |     |      |
| cct | gag | att | ctg | tcg | cct | ttg | cag | ccc | cca | ctc | tgt | ggg | caa | aca | gtc | 1509 |
| Pro | Glu | Ile | Leu | Ser | Pro | Leu | Gln | Pro | Pro | Leu | Cys | Gly | Gln | Thr | Val |      |
| 255 |     |     |     | 260 |     |     |     | 265 |     |     |     | 270 |     |     |     |      |
| tgt | gac | aat | gtg | gaa | ttg | atc | tcc | cag | tac | aat | gga | tac | tgg | ccc | ctt | 1557 |
| Cys | Asp | Asn | Val | Glu | Leu | Ile | Ser | Gln | Tyr | Asn | Gly | Tyr | Trp | Pro | Leu |      |
|     |     |     | 275 |     |     |     | 280 |     |     |     | 285 |     |     |     |     |      |

-continued

| | |
|---|---|
| cgg gga gag aag gtg ata cgc tac cag gtg gtg aac atc tgt gat gat<br>Arg Gly Glu Lys Val Ile Arg Tyr Gln Val Val Asn Ile Cys Asp Asp<br>              290                          295                        300 | 1605 |
| gag ggc cta aac ccc att gtg agt gag gag cag att cgt ctg cag cac<br>Glu Gly Leu Asn Pro Ile Val Ser Glu Glu Gln Ile Arg Leu Gln His<br>           305                          310                          315 | 1653 |
| gag gca ctg aat gag gcc ttc agc cgc tac aac atc agc tgg cag ctg<br>Glu Ala Leu Asn Glu Ala Phe Ser Arg Tyr Asn Ile Ser Trp Gln Leu<br>320                          325                          330 | 1701 |
| agc gtc cac cag gtc cac aat tcc acc ctg cga cac cgg gtt gtg ctt<br>Ser Val His Gln Val His Asn Ser Thr Leu Arg His Arg Val Val Leu<br>335                          340                          345                        350 | 1749 |
| gtg aac tgt gag ccc agc aag att ggc aat gac cat tgt gac ccc gag<br>Val Asn Cys Glu Pro Ser Lys Ile Gly Asn Asp His Cys Asp Pro Glu<br>                        355                          360                          365 | 1797 |
| tgt gag cac cca ctc aca ggc tat gat ggg ggt gac tgc cgc ctg cag<br>Cys Glu His Pro Leu Thr Gly Tyr Asp Gly Gly Asp Cys Arg Leu Gln<br>                  370                          375                          380 | 1845 |
| ggc cgc tgc tac tcc tgg aac cgc agg gat ggg ctc tgt cac gtg gag<br>Gly Arg Cys Tyr Ser Trp Asn Arg Arg Asp Gly Leu Cys His Val Glu<br>385                          390                          395 | 1893 |
| tgt aac aac atg ctg aac gac ttt gac gac gga gac tgc tgc gac ccc<br>Cys Asn Asn Met Leu Asn Asp Phe Asp Asp Gly Asp Cys Cys Asp Pro<br>            400                          405                          410 | 1941 |
| cag gtg gct gat gtg cgc aag acc tgt ttt gac cct gac tca ccc aag<br>Gln Val Ala Asp Val Arg Lys Thr Cys Phe Asp Pro Asp Ser Pro Lys<br>415                          420                          425                        430 | 1989 |
| agg gca tac atg agt gtg aag gag ctg aag gag gcc ctg cag ctg aac<br>Arg Ala Tyr Met Ser Val Lys Glu Leu Lys Glu Ala Leu Gln Leu Asn<br>                  435                          440                          445 | 2037 |
| agt act cac ttc ctc aac atc tac ttt gcc agc tca gtg cgg gaa gac<br>Ser Thr His Phe Leu Asn Ile Tyr Phe Ala Ser Ser Val Arg Glu Asp<br>                    450                          455                          460 | 2085 |
| ctt gca ggt gct gcc acc tgg cct tgg gac aag gac gct gtc act cac<br>Leu Ala Gly Ala Ala Thr Trp Pro Trp Asp Lys Asp Ala Val Thr His<br>              465                          470                          475 | 2133 |
| ctg ggt ggc att gtc ctc agc cca gca tat tat ggg atg cct ggc cac<br>Leu Gly Gly Ile Val Leu Ser Pro Ala Tyr Tyr Gly Met Pro Gly His<br>480                          485                          490 | 2181 |
| acc gac acc atg atc cat gaa gtg gga cat gtt ctg gga ctc tac cat<br>Thr Asp Thr Met Ile His Glu Val Gly His Val Leu Gly Leu Tyr His<br>495                          500                          505                        510 | 2229 |
| gtc ttt aaa gga gtc agt gaa aga gaa tcc tgc aat gac ccc tgc aag<br>Val Phe Lys Gly Val Ser Glu Arg Glu Ser Cys Asn Asp Pro Cys Lys<br>                    515                          520                          525 | 2277 |
| gag aca gtg cca tcc atg gaa acg gga gac ctc tgt gcc gac acc gcc<br>Glu Thr Val Pro Ser Met Glu Thr Gly Asp Leu Cys Ala Asp Thr Ala<br>                    530                          535                          540 | 2325 |
| ccc act ccc aag agt gag ctg tgc cgg gaa cca gag ccc act agt gac<br>Pro Thr Pro Lys Ser Glu Leu Cys Arg Glu Pro Glu Pro Thr Ser Asp<br>                        545                          550                          555 | 2373 |
| acc tgt ggc ttc act cgc ttc cca ggg gct ccg ttc acc aac tac atg<br>Thr Cys Gly Phe Thr Arg Phe Pro Gly Ala Pro Phe Thr Asn Tyr Met<br>560                          565                          570 | 2421 |
| agc tac acg gat gat aac tgc act gac aac ttc act cct aac caa gtg<br>Ser Tyr Thr Asp Asp Asn Cys Thr Asp Asn Phe Thr Pro Asn Gln Val<br>575                          580                          585                        590 | 2469 |
| gcc cga atg cat tgc tat ttg gac cta gtc tat cag cag tgg act gaa<br>Ala Arg Met His Cys Tyr Leu Asp Leu Val Tyr Gln Gln Trp Thr Glu<br>                    595                          600                        605 | 2517 |

-continued

```
agc aga aag ccc acc ccc atc ccc att cca cct atg gtc atc gga cag       2565
Ser Arg Lys Pro Thr Pro Ile Pro Ile Pro Pro Met Val Ile Gly Gln
            610                 615                 620 acc aac aag tcc ctc act atc cac tgg ctg cct cct att agt gga gtt       2613
Thr Asn Lys Ser Leu Thr Ile His Trp Leu Pro Pro Ile Ser Gly Val
        625                 630                 635 gta tat gac agg gcc tca ggc agc ttg tgt ggc gct tgc act gaa gat       2661
Val Tyr Asp Arg Ala Ser Gly Ser Leu Cys Gly Ala Cys Thr Glu Asp
    640                 645                 650 ggg acc ttt cgt cag tat gtg cac aca gct tcc tcc cgg cgg gtg tgt       2709
Gly Thr Phe Arg Gln Tyr Val His Thr Ala Ser Ser Arg Arg Val Cys
655                 660                 665                 670 gac tcc tca ggt tat tgg acc cca gag gag gct gtg ggg cct cct gat       2757
Asp Ser Ser Gly Tyr Trp Thr Pro Glu Glu Ala Val Gly Pro Pro Asp
                675                 680                 685 gtg gat cag ccc tgc gag cca agc tta cag gcc tgg agc cct gag gtc       2805
Val Asp Gln Pro Cys Glu Pro Ser Leu Gln Ala Trp Ser Pro Glu Val
            690                 695                 700 cac ctg tac cac atg aac atg acg gtc ccc tgc ccc aca gaa ggc tgt       2853
His Leu Tyr His Met Asn Met Thr Val Pro Cys Pro Thr Glu Gly Cys
        705                 710                 715 agc ttg gag ctg ctc ttc caa cac ccg gtc caa gcc gac acc ctc acc       2901
Ser Leu Glu Leu Leu Phe Gln His Pro Val Gln Ala Asp Thr Leu Thr
    720                 725                 730 ctg tgg gtc act tcc ttc ttc atg gag tcc tcg cag gtc ctc ttt gac       2949
Leu Trp Val Thr Ser Phe Phe Met Glu Ser Ser Gln Val Leu Phe Asp
735                 740                 745                 750 aca gag atc ttg ctg gaa aac aag gag tca gtg cac ctg ggc ccc tta       2997
Thr Glu Ile Leu Leu Glu Asn Lys Glu Ser Val His Leu Gly Pro Leu
                755                 760                 765 gac act ttc tgt gac atc cca ctc acc atc aaa ctg cac gtg gat ggg       3045
Asp Thr Phe Cys Asp Ile Pro Leu Thr Ile Lys Leu His Val Asp Gly
            770                 775                 780 aag gtg tcg ggg gtg aaa gtc tac acc ttt gat gag agg ata gag att       3093
Lys Val Ser Gly Val Lys Val Tyr Thr Phe Asp Glu Arg Ile Glu Ile
        785                 790                 795 gat gca gca ctc ctg act tct cag ccc cac agt ccc ttg tgc tct ggc       3141
Asp Ala Ala Leu Leu Thr Ser Gln Pro His Ser Pro Leu Cys Ser Gly
    800                 805                 810 tgc agg cct gtg agg tac cag gtt ctc cgc gat ccc cca ttt gcc agt       3189
Cys Arg Pro Val Arg Tyr Gln Val Leu Arg Asp Pro Pro Phe Ala Ser
815                 820                 825                 830 ggt ttg ccc gtg gtg gtg aca cat tct cac agg aag ttc acg gac gtg       3237
Gly Leu Pro Val Val Val Thr His Ser His Arg Lys Phe Thr Asp Val
                835                 840                 845 gag gtc aca cct gga cag atg tat cag tac caa gtt cta gct gaa gct       3285
Glu Val Thr Pro Gly Gln Met Tyr Gln Tyr Gln Val Leu Ala Glu Ala
            850                 855                 860 gga gga gaa ctg gga gaa gct tcg cct cct ctg aac cac att cat gga       3333
Gly Gly Glu Leu Gly Glu Ala Ser Pro Pro Leu Asn His Ile His Gly
        865                 870                 875 gct cct tat tgt gga gat ggg aag gtg tca gag aga ctg gga gaa gag       3381
Ala Pro Tyr Cys Gly Asp Gly Lys Val Ser Glu Arg Leu Gly Glu Glu
    880                 885                 890 tgt gat gat gga gac ctt gtg agc gga gat ggc tgc tcc aag gtg tgt       3429
Cys Asp Asp Gly Asp Leu Val Ser Gly Asp Gly Cys Ser Lys Val Cys
895                 900                 905                 910
```

-continued

```
gag ctg gag gaa ggt ttc aac tgt gta gga gag cca agc ctt tgc tac    3477
Glu Leu Glu Glu Gly Phe Asn Cys Val Gly Glu Pro Ser Leu Cys Tyr
            915                 920                 925 atg tat gag gga gat ggc ata tgt gaa cct ttt gag aga aaa acc agc    3525
Met Tyr Glu Gly Asp Gly Ile Cys Glu Pro Phe Glu Arg Lys Thr Ser
        930                 935                 940 att gta gac tgt ggc atc tac act ccc aaa gga tac ttg gat caa tgg    3573
Ile Val Asp Cys Gly Ile Tyr Thr Pro Lys Gly Tyr Leu Asp Gln Trp
    945                 950                 955 gct acc cgg gct tac tcc tct cat gaa gac aag aag aag tgt cct gtt    3621
Ala Thr Arg Ala Tyr Ser Ser His Glu Asp Lys Lys Lys Cys Pro Val
960                 965                 970 tcc ttg gta act gga gaa cct cat tcc cta att tgc aca tca tac cat    3669
Ser Leu Val Thr Gly Glu Pro His Ser Leu Ile Cys Thr Ser Tyr His
975                 980                 985                 990 cca gat tta ccc aac cac cgt ccc cta act  ggc tgg ttt ccc tgt  gtt   3717
Pro Asp Leu Pro Asn His Arg Pro Leu Thr  Gly Trp Phe Pro Cys  Val
                995                 1000                 1005 gcc agt gaa aat  gaa act cag gat gac  agg agt gaa cag cca  gaa       3762
Ala Ser Glu Asn  Glu Thr Gln Asp Asp  Arg Ser Glu Gln Pro  Glu
            1010                 1015                 1020 ggt agc ctg aag  aaa gag gat gag gtt  tgg ctc aaa gtg tgt  ttc       3807
Gly Ser Leu Lys  Lys Glu Asp Glu Val  Trp Leu Lys Val Cys  Phe
            1025                 1030                 1035 aat aga cca gga  gag gcc aga gca att  ttt att ttt ttg aca  act       3852
Asn Arg Pro Gly  Glu Ala Arg Ala Ile  Phe Ile Phe Leu Thr  Thr
            1040                 1045                 1050 gat ggc cta gtt  ccc gga gag cat cag  cag ccg aca gtg act  ctc       3897
Asp Gly Leu Val  Pro Gly Glu His Gln  Gln Pro Thr Val Thr  Leu
            1055                 1060                 1065 tac ctg acc gat  gtc cgt gga agc aac  cac tct ctt gga acc  tat       3942
Tyr Leu Thr Asp  Val Arg Gly Ser Asn  His Ser Leu Gly Thr  Tyr
            1070                 1075                 1080 gga ctg tca tgc  cag cat aat cca ctg  att atc aat gtg acc  cat       3987
Gly Leu Ser Cys  Gln His Asn Pro Leu  Ile Ile Asn Val Thr  His
            1085                 1090                 1095 cac cag aat gtc  ctt ttc cac cat acc  acc tca gtg ctg ctg  aat       4032
His Gln Asn Val  Leu Phe His His Thr  Thr Ser Val Leu Leu  Asn
            1100                 1105                 1110 ttc tca tcc cca  cgg gtc ggc atc tca  gct gtg gct cta agg  aca       4077
Phe Ser Ser Pro  Arg Val Gly Ile Ser  Ala Val Ala Leu Arg  Thr
            1115                 1120                 1125 tcc tcc cgc att  ggt ctt tcg gct ccc  agt aac tgc atc tca  gag       4122
Ser Ser Arg Ile  Gly Leu Ser Ala Pro  Ser Asn Cys Ile Ser  Glu
            1130                 1135                 1140 gac gag ggg cag  aat cat cag gga cag  agc tgt atc cat cgg  ccc       4167
Asp Glu Gly Gln  Asn His Gln Gly Gln  Ser Cys Ile His Arg  Pro
            1145                 1150                 1155 tgt ggg aag cag  gac agc tgt ccg tca  ttg ctg ctt gat cat  gct       4212
Cys Gly Lys Gln  Asp Ser Cys Pro Ser  Leu Leu Leu Asp His  Ala
            1160                 1165                 1170 gat gtg gtg aac  tgt acc tct ata ggc  cca ggt ctc atg aag  tgt       4257
Asp Val Val Asn  Cys Thr Ser Ile Gly  Pro Gly Leu Met Lys  Cys
            1175                 1180                 1185 gct atc act tgt  caa agg gga ttt gcc  ctt cag gcc agc agt  ggg       4302
Ala Ile Thr Cys  Gln Arg Gly Phe Ala  Leu Gln Ala Ser Ser  Gly
            1190                 1195                 1200
```

-continued

| | | | | | | | | | | | | |
|---|---|---|---|---|---|---|---|---|---|---|---|---|
| cag | tac | atc | agg | ccc | atg | cag | aag | gaa | att | ctg | ctc | aca | tgt | tct | 4347 |
| Gln | Tyr | Ile | Arg<br>1205 | Pro | Met | Gln | Lys<br>1210 | Glu | Ile | Leu | Leu | Thr<br>1215 | Cys | Ser | |

```
cag tac atc agg ccc atg cag aag gaa att ctg ctc aca tgt tct      4347
Gln Tyr Ile Arg Pro Met Gln Lys Glu Ile Leu Leu Thr Cys Ser
            1205            1210               1215 tct ggg cac tgg gac cag aat gtg agc tgc ctt ccc gtg gac tgc      4392
Ser Gly His Trp Asp Gln Asn Val Ser Cys Leu Pro Val Asp Cys
            1220            1225               1230 ggt gtt ccc gac ccg tct ttg gtg aac tat gca aac ttc tcc tgc      4437
Gly Val Pro Asp Pro Ser Leu Val Asn Tyr Ala Asn Phe Ser Cys
            1235            1240               1245 tca gag gga acc aaa ttt ctg aaa cgc tgc tca atc tct tgt gtc      4482
Ser Glu Gly Thr Lys Phe Leu Lys Arg Cys Ser Ile Ser Cys Val
            1250            1255               1260 cca cca gcc aag ctg caa gga ctg agc cca tgg ctg aca tgt ctt      4527
Pro Pro Ala Lys Leu Gln Gly Leu Ser Pro Trp Leu Thr Cys Leu
            1265            1270               1275 gaa gat ggt ctc tgg tct ctc cct gaa gtc tac tgc aag ttg gag      4572
Glu Asp Gly Leu Trp Ser Leu Pro Glu Val Tyr Cys Lys Leu Glu
            1280            1285               1290 tgt gat gct ccc cct att att ctg aat gcc aac ttg ctc ctg cct      4617
Cys Asp Ala Pro Pro Ile Ile Leu Asn Ala Asn Leu Leu Leu Pro
            1295            1300               1305 cac tgc ctc cag gac aac cac gac gtg ggc acc atc tgc aaa tat      4662
His Cys Leu Gln Asp Asn His Asp Val Gly Thr Ile Cys Lys Tyr
            1310            1315               1320 gaa tgc aaa cca ggg tac tat gtg gca gaa agt gca gag ggt aaa      4707
Glu Cys Lys Pro Gly Tyr Tyr Val Ala Glu Ser Ala Glu Gly Lys
            1325            1330               1335 gtc agg aac aag ctc ctg aag ata caa tgc ctg gaa ggt gga atc      4752
Val Arg Asn Lys Leu Leu Lys Ile Gln Cys Leu Glu Gly Gly Ile
            1340            1345               1350 tgg gag caa ggc agc tgc att cct gtg gtg tgt gag cca ccc cct      4797
Trp Glu Gln Gly Ser Cys Ile Pro Val Val Cys Glu Pro Pro Pro
            1355            1360               1365 cct gtg ttt gaa ggc atg tat gaa tgt acc aat ggc ttc agc ctg      4842
Pro Val Phe Glu Gly Met Tyr Glu Cys Thr Asn Gly Phe Ser Leu
            1370            1375               1380 gac agc cag tgt gtg ctc aac tgt aac cag gaa cgt gaa aag ctt      4887
Asp Ser Gln Cys Val Leu Asn Cys Asn Gln Glu Arg Glu Lys Leu
            1385            1390               1395 ccc atc ctc tgc act aaa gag ggc ctg tgg acc cag gag ttt aag      4932
Pro Ile Leu Cys Thr Lys Glu Gly Leu Trp Thr Gln Glu Phe Lys
            1400            1405               1410 ttg tgt gag aat ctg caa gga gaa tgc cca cca ccc ccc tca gag      4977
Leu Cys Glu Asn Leu Gln Gly Glu Cys Pro Pro Pro Pro Ser Glu
            1415            1420               1425 ctg aat tct gtg gag tac aaa tgt gaa caa gga tat ggg att ggt      5022
Leu Asn Ser Val Glu Tyr Lys Cys Glu Gln Gly Tyr Gly Ile Gly
            1430            1435               1440 gca gtg tgt tcc cca ttg tgt gta atc ccc ccc agt gac ccc gtg      5067
Ala Val Cys Ser Pro Leu Cys Val Ile Pro Pro Ser Asp Pro Val
            1445            1450               1455 atg cta cct gag aat atc act gct gac act ctg gag cac tgg atg      5112
Met Leu Pro Glu Asn Ile Thr Ala Asp Thr Leu Glu His Trp Met
            1460            1465               1470 gaa cct gtc aaa gtc cag agc att gtg tgc act ggc cgg cgt caa      5157
Glu Pro Val Lys Val Gln Ser Ile Val Cys Thr Gly Arg Arg Gln
            1475            1480               1485 tgg cac cca gac ccc gtc tta gtc cac tgc atc cag tca tgt gag      5202
Trp His Pro Asp Pro Val Leu Val His Cys Ile Gln Ser Cys Glu
            1490            1495               1500
```

-continued

| | | | | | | | | | | | | | |
|---|---|---|---|---|---|---|---|---|---|---|---|---|---|
| ccc | ttc | caa | gca | gat | ggt | tgg | tgt | gac | act | atc | aac | aac | cga | gcc | 5247 |
| Pro | Phe | Gln | Ala | Asp | Gly | Trp | Cys | Asp | Thr | Ile | Asn | Asn | Arg | Ala |
| | | 1505 | | | | | 1510 | | | | | 1515 | | |

| tac | tgc | cac | tat | gac | ggg | gga | gac | tgc | tgc | tct | tcc | aca | ctc | tcc | 5292 |
| Tyr | Cys | His | Tyr | Asp | Gly | Gly | Asp | Cys | Cys | Ser | Ser | Thr | Leu | Ser |
| | | | 1520 | | | | | 1525 | | | | | 1530 | |

| tcc | aag | aag | gtc | att | cca | ttt | gct | gct | gac | tgt | gac | ctg | gat | gag | 5337 |
| Ser | Lys | Lys | Val | Ile | Pro | Phe | Ala | Ala | Asp | Cys | Asp | Leu | Asp | Glu |
| | | | 1535 | | | | | 1540 | | | | | 1545 | |

| tgc | acc | tgc | cgg | gac | ccc | aag | gca | gaa | gaa | aat | cag | taactgtggg | | | 5383 |
| Cys | Thr | Cys | Arg | Asp | Pro | Lys | Ala | Glu | Glu | Asn | Gln | | | |
| | | | 1550 | | | | | 1555 | | | | | | |

```
aacaagcccc tccctccact gcctcagagg cagtaagaaa gagaggccga cccaggagga    5443
aacaaagggt gaatgaagaa gaacaatcat gaaatggaag aaggaggaag agcatgaagg    5503
atcttataag aaatgcaaga ggatattgat aggtgtgaac tagttcatca agtagcccaa    5563
gtaggagaga atcataggca aaagtttctt taaagtggca gttgattaac atggaagggg    5623
aaatatgata gatatataag gaccctcctc cctcacttat attctattaa atcctatcct    5683
caactcttgc cctgctctcc gctccacccc ctgccaacta ctcagtccca cccaacttgt    5743
aaaccaatac caaaatacta gaggagaagt tggcagggat actgttaata cccatttga    5803 atggattgcc atctttcaga gcttgtctgc tctcaactgg ctcttttct ttttgtgtag     5863 tttcccttaa ataatgaagt tagttattaa ttctttataa gtatttaaac ataattatat    5923
aaatatatta tatatattat attttttgct gtttactaag ctaaaaatta ttcattgttc    5983
cacacatgct gctgtgaagt tcacattcaa gatgaatgtt gagactttga ggacagaaag    6043
gcaacttatt ttcccatctt tctatggatg cggattggca ggttgaatgg gaagtacaga    6103
aggagagaga gtaattagat ggaattctgg atgctagcat gtaaagctaa tcatcttttt    6163
ttttatgacc tgggagctgg gcccattta tgaccaagga gatggggagt tggaatggtg     6223
gtactaagag gcataggaag ttgagtgtga ataccattgg tgatgggtcc aggagaacta    6283
gactatggtt cttgaatatc tgtccacaaa gaatatacta acttttgtca acttctcaga    6343
actcccaact ggagtcggtg agacctagga ttttctgcac ttccacacat gcctgttcca    6403
agtgtggctg tcagccagtc aacaagtttg tactatggcc cattctctga tcaccaggat    6463
tacaggaact cacacactcc tcatacttgg cctgtagtcc tacttcttgt tagaagtctc    6523
caagtctggc cagtcacatg accaagtgtt gattttctg gaggaaaaat tttatggaaa      6583
tgatataggg gaaaggtggg aggagatgaa agaacaggca agagctgtca gggttaaatc    6643
caggcccggg catgagaatg gaagtgatca gggagactcg gtccttgttc caagtctcca    6703
aagaagacca aagtgggtcc cttgagcaat gaagaatctg agataaattc tcttcaagta    6763
tcatgtacaa aatctgtgag ccagagattt tgacttgagc aagccatgga aatgcatgga    6823
gcaagggtga cactctgtgg ggagacagaa gaatttcaac tatttaatgt ccattttgtt    6883
gtttttaccc tttcttatcc aatagatgga atgcacatga aatgaccata ttaagcctct    6943
ctctatttac atcccaggct cactgggatg tgatctactg cagttacatt ttcttgtaac    7003
ggtttctgga ttagacccta gggaaagtga gtaaggagcc agtttctgtt taacattcta    7063
gttttactca tttaggaag ctgtgagtg aggcttgtct cctttaaagt ttcttctcca       7123
atggaaacca agaacagaca aaatttagag ctcagctgtg gtctcttctc atcttctgct    7183
cttttgcttt gaccacagtt tttctactct tcccatcaac actagagcaa tggctgtgca    7243
```

-continued

```
aataggaata ggaaatacta ccacaatgat agaaatatta tccacactat cacgtaggga      7303
agaacaatat cctgaaagag aataaaacac gaataaggtg atgtacccac attaatctgt      7363
gggtttgtgg aatgagggtt gcaaagttat tgggaaaagg aaagagcaga gttcacccat      7423
tcaaaaaaaa ccttttgtct actaatctct agtgtaaaga aaatgtagtt cagataccat      7483
tcattgtctt gggtcatgct tagtgccccc aagaagacaa acatatttat tcttgggatt      7543
ctgataggct tcaatatgca aaggacaatg gaaaagttta gacactctat tttcaaaatt      7603
ttataaactt gttttattgg ggaaaatgtc caaattgcta gacacattct aagttctgcc      7663
ttggagaatc ctactttgtc tgagattgag gcagaggaat tgttatcctg ggcattactc      7723
agctcaggaa catggagcct gtggttcatg ccagtgtgtg tcttcatgca gtctctccac      7783
aagagcaaca gtaagaacat ttctgtttta aatttcattt taaaatattt tattatctgc      7843
aattcaccac tgctctggga aagcaaaagg aaagttcctg ttgtgtgtga agagcctctt      7903
aggctataag gcttcccagc catagtcagc tatagctatt cagagacagc aggttcttcc      7963
agtctttgtt cctgggacct gatgttttga gcaactcagg tcactgataa agtggaagga      8023
ctaagacact gtggtcacag atcccagcaa catcaactca cactcaatcc atgtggtggt      8083
ccacattctg ctactcttat ccacccatgt ggtcattgag agcctttctc agagactctt      8143
ctgtgtgttt gattgtgccc aggtggccca gggctagctg gctctaacaa ctagcatgac      8203
agcctccaat cagaaaggca ggtaagggga cagggtgagg agaatgggca gatactgaca      8263
gaaattaaag taaagggatt gtgaaagtaa agagctcttc ctgattctca tcttctcttt      8323
tttctattac aaggcattga acttggcact tcctgtattc tttgtgatca ctattgagtg      8383
cattagttaa cacccaaggg gatggcttga ttgggaatgt agtgaaagga gctgatctac      8443
tgtattgtaa tgtaaaacag ctacagccag ttattttgta agattataag ttgttcatta      8503
aaaaatcagc acacaaaata tgaa                                            8527
```

<210> SEQ ID NO 2
<211> LENGTH: 1791
<212> TYPE: PRT
<213> ORGANISM: Homo sapiens
<220> FEATURE:
<221> NAME/KEY: misc_feature
<222> LOCATION: (1)..(66)
<223> OTHER INFORMATION: prepro part of PAPP-A2
<220> FEATURE:
<221> NAME/KEY: misc_feature
<222> LOCATION: (67)..(699)
<223> OTHER INFORMATION: pro part of PAPP-A2

<400> SEQUENCE: 2

```
Met Met Cys Leu  Lys Ile Leu Arg  Ile Ser Leu Ala  Ile Leu Ala
            -230             -225             -220

Gly Trp Ala Leu  Cys Ser Ala Asn  Ser Glu Leu Gly  Trp Thr Arg
            -215             -210             -205

Lys Lys Ser Leu  Val Glu Arg Glu  His Leu Asn Gln  Val Leu Leu
            -200             -195             -190

Glu Gly Glu Arg  Cys Trp Leu Gly  Ala Lys Val Arg  Arg Pro Arg
            -185             -180             -175

Ala Ser Pro Gln  His His Leu Phe  Gly Val Tyr Pro  Ser Arg Ala
            -170             -165             -160

Gly Asn Tyr Leu  Arg Pro Tyr Pro  Val Gly Glu Gln  Glu Ile His
            -155             -150             -145
```

-continued

```
His Thr Gly Arg Ser Lys Pro Asp Thr Glu Gly Asn Ala Val Ser
        -140            -135             -130

Leu Val Pro Pro Asp Leu Thr Glu Asn Pro Ala Gly Leu Arg Gly
        -125            -120             -115

Ala Val Glu Glu Pro Ala Ala Pro Trp Val Gly Asp Ser Pro Ile
        -110            -105             -100

Gly Gln Ser Glu Leu Gly Asp Asp Ala Tyr Leu Gly Asn Gln
         -95             -90              -85

Arg Ser Lys Glu Ser Leu Gly Glu Ala Gly Ile Gln Lys Gly Ser Ala
         -80             -75              -70

Met Ala Ala Thr Thr Thr Thr Ala Ile Phe Thr Thr Leu Asn Glu Pro
         -65             -60              -55

Lys Pro Glu Thr Gln Arg Arg Gly Trp Ala Lys Ser Arg Gln Arg Arg
-50              -45              -40              -35

Gln Val Trp Lys Arg Arg Ala Glu Asp Gly Gln Gly Asp Ser Gly Ile
             -30              -25              -20

Ser Ser His Phe Gln Pro Trp Pro Lys His Ser Leu Lys His Arg Val
         -15             -10               -5

Lys Lys Ser Pro Pro Glu Glu Ser Asn Gln Asn Gly Gly Glu Gly Ser
 -1  1               5                        10

Tyr Arg Glu Ala Glu Thr Phe Asn Ser Gln Val Gly Leu Pro Ile Leu
15               20               25                       30

Tyr Phe Ser Gly Arg Glu Arg Leu Leu Leu Arg Pro Glu Val Leu
             35              40               45

Ala Glu Ile Pro Arg Glu Ala Phe Thr Val Glu Ala Trp Val Lys Pro
             50              55              60

Glu Gly Gly Gln Asn Asn Pro Ala Ile Ile Ala Gly Val Phe Asp Asn
             65              70              75

Cys Ser His Thr Val Ser Asp Lys Gly Trp Ala Leu Gly Ile Arg Ser
80               85               90

Gly Lys Asp Lys Gly Lys Arg Asp Ala Arg Phe Phe Phe Ser Leu Cys
95               100              105                      110

Thr Asp Arg Val Lys Lys Ala Thr Ile Leu Ile Ser His Ser Arg Tyr
             115              120              125

Gln Pro Gly Thr Trp Thr His Val Ala Ala Thr Tyr Asp Gly Arg His
             130              135              140

Met Ala Leu Tyr Val Asp Gly Thr Gln Val Ala Ser Ser Leu Asp Gln
             145              150              155

Ser Gly Pro Leu Asn Ser Pro Phe Met Ala Ser Cys Arg Ser Leu Leu
             160              165              170

Leu Gly Gly Asp Ser Ser Glu Asp Gly His Tyr Phe Arg Gly His Leu
175              180              185                      190

Gly Thr Leu Val Phe Trp Ser Thr Ala Leu Pro Gln Ser His Phe Gln
             195              200              205

His Ser Ser Gln His Ser Ser Gly Glu Glu Ala Thr Asp Leu Val
             210              215              220

Leu Thr Ala Ser Phe Glu Pro Val Asn Thr Glu Trp Val Pro Phe Arg
             225              230              235

Asp Glu Lys Tyr Pro Arg Leu Glu Val Leu Gln Gly Phe Glu Pro Glu
             240              245              250

Pro Glu Ile Leu Ser Pro Leu Gln Pro Leu Cys Gly Gln Thr Val
255              260              265              270
```

```
Cys Asp Asn Val Glu Leu Ile Ser Gln Tyr Asn Gly Tyr Trp Pro Leu
                275                 280                 285
Arg Gly Glu Lys Val Ile Arg Tyr Gln Val Val Asn Ile Cys Asp Asp
            290                 295                 300
Glu Gly Leu Asn Pro Ile Val Ser Glu Glu Gln Ile Arg Leu Gln His
        305                 310                 315
Glu Ala Leu Asn Glu Ala Phe Ser Arg Tyr Asn Ile Ser Trp Gln Leu
    320                 325                 330
Ser Val His Gln Val His Asn Ser Thr Leu Arg His Arg Val Val Leu
335                 340                 345                 350
Val Asn Cys Glu Pro Ser Lys Ile Gly Asn Asp His Cys Asp Pro Glu
                355                 360                 365
Cys Glu His Pro Leu Thr Gly Tyr Asp Gly Gly Asp Cys Arg Leu Gln
            370                 375                 380
Gly Arg Cys Tyr Ser Trp Asn Arg Arg Asp Gly Leu Cys His Val Glu
        385                 390                 395
Cys Asn Asn Met Leu Asn Asp Phe Asp Asp Gly Asp Cys Cys Asp Pro
    400                 405                 410
Gln Val Ala Asp Val Arg Lys Thr Cys Phe Asp Pro Asp Ser Pro Lys
415                 420                 425                 430
Arg Ala Tyr Met Ser Val Lys Glu Leu Lys Glu Ala Leu Gln Leu Asn
                435                 440                 445
Ser Thr His Phe Leu Asn Ile Tyr Phe Ala Ser Ser Val Arg Glu Asp
            450                 455                 460
Leu Ala Gly Ala Ala Thr Trp Pro Trp Asp Lys Asp Ala Val Thr His
        465                 470                 475
Leu Gly Gly Ile Val Leu Ser Pro Ala Tyr Tyr Gly Met Pro Gly His
    480                 485                 490
Thr Asp Thr Met Ile His Glu Val Gly His Val Leu Gly Leu Tyr His
495                 500                 505                 510
Val Phe Lys Gly Val Ser Glu Arg Glu Ser Cys Asn Asp Pro Cys Lys
                515                 520                 525
Glu Thr Val Pro Ser Met Glu Thr Gly Asp Leu Cys Ala Asp Thr Ala
            530                 535                 540
Pro Thr Pro Lys Ser Glu Leu Cys Arg Glu Pro Glu Pro Thr Ser Asp
        545                 550                 555
Thr Cys Gly Phe Thr Arg Phe Pro Gly Ala Pro Phe Thr Asn Tyr Met
    560                 565                 570
Ser Tyr Thr Asp Asp Asn Cys Thr Asp Asn Phe Thr Pro Asn Gln Val
575                 580                 585                 590
Ala Arg Met His Cys Tyr Leu Asp Leu Val Tyr Gln Gln Trp Thr Glu
                595                 600                 605
Ser Arg Lys Pro Thr Pro Ile Pro Ile Pro Pro Met Val Ile Gly Gln
            610                 615                 620
Thr Asn Lys Ser Leu Thr Ile His Trp Leu Pro Pro Ile Ser Gly Val
        625                 630                 635
Val Tyr Asp Arg Ala Ser Gly Ser Leu Cys Gly Ala Cys Thr Glu Asp
    640                 645                 650
Gly Thr Phe Arg Gln Tyr Val His Thr Ala Ser Ser Arg Arg Val Cys
655                 660                 665                 670
Asp Ser Ser Gly Tyr Trp Thr Pro Glu Glu Ala Val Gly Pro Pro Asp
                675                 680                 685
```

-continued

```
Val Asp Gln Pro Cys Glu Pro Ser Leu Gln Ala Trp Ser Pro Glu Val
            690                 695                 700
His Leu Tyr His Met Asn Met Thr Val Pro Cys Pro Thr Glu Gly Cys
705                 710                 715
Ser Leu Glu Leu Leu Phe Gln His Pro Val Gln Ala Asp Thr Leu Thr
        720                 725                 730
Leu Trp Val Thr Ser Phe Phe Met Glu Ser Ser Gln Val Leu Phe Asp
735                 740                 745                 750
Thr Glu Ile Leu Leu Glu Asn Lys Glu Ser Val His Leu Gly Pro Leu
                755                 760                 765
Asp Thr Phe Cys Asp Ile Pro Leu Thr Ile Lys Leu His Val Asp Gly
            770                 775                 780
Lys Val Ser Gly Val Lys Val Tyr Thr Phe Asp Glu Arg Ile Glu Ile
785                 790                 795
Asp Ala Ala Leu Leu Thr Ser Gln Pro His Ser Pro Leu Cys Ser Gly
        800                 805                 810
Cys Arg Pro Val Arg Tyr Gln Val Leu Arg Asp Pro Pro Phe Ala Ser
815                 820                 825                 830
Gly Leu Pro Val Val Thr His Ser His Arg Lys Phe Thr Asp Val
                835                 840                 845
Glu Val Thr Pro Gly Gln Met Tyr Gln Tyr Gln Val Leu Ala Glu Ala
            850                 855                 860
Gly Gly Glu Leu Gly Glu Ala Ser Pro Pro Leu Asn His Ile His Gly
        865                 870                 875
Ala Pro Tyr Cys Gly Asp Gly Lys Val Ser Arg Leu Gly Glu Glu
880                 885                 890
Cys Asp Asp Gly Asp Leu Val Ser Gly Asp Gly Cys Ser Lys Val Cys
895                 900                 905                 910
Glu Leu Glu Glu Gly Phe Asn Cys Val Gly Glu Pro Ser Leu Cys Tyr
                915                 920                 925
Met Tyr Glu Gly Asp Gly Ile Cys Glu Pro Phe Glu Arg Lys Thr Ser
            930                 935                 940
Ile Val Asp Cys Gly Ile Tyr Thr Pro Lys Gly Tyr Leu Asp Gln Trp
        945                 950                 955
Ala Thr Arg Ala Tyr Ser Ser His Glu Asp Lys Lys Lys Cys Pro Val
960                 965                 970
Ser Leu Val Thr Gly Glu Pro His Ser Leu Ile Cys Thr Ser Tyr His
975                 980                 985                 990
Pro Asp Leu Pro Asn His Arg Pro Leu Thr Gly Trp Phe Pro Cys Val
                995                 1000                1005
Ala Ser Glu Asn Glu Thr Gln Asp Asp Arg Ser Glu Gln Pro Glu
            1010                1015                1020
Gly Ser Leu Lys Lys Glu Asp Glu Val Trp Leu Lys Val Cys Phe
        1025                1030                1035
Asn Arg Pro Gly Glu Ala Arg Ala Ile Phe Ile Phe Leu Thr Thr
        1040                1045                1050
Asp Gly Leu Val Pro Gly Glu His Gln Gln Pro Thr Val Thr Leu
        1055                1060                1065
Tyr Leu Thr Asp Val Arg Gly Ser Asn His Ser Leu Gly Thr Tyr
        1070                1075                1080
Gly Leu Ser Cys Gln His Asn Pro Leu Ile Ile Asn Val Thr His
        1085                1090                1095
```

```
His Gln Asn Val Leu Phe His His Thr     Thr Ser Val Leu Leu Asn
        1100                1105                    1110

Phe Ser Ser Pro Arg Val Gly Ile Ser     Ala Val Ala Leu Arg Thr
        1115                1120                    1125

Ser Ser Arg Ile Gly Leu Ser Ala Pro     Ser Asn Cys Ile Ser Glu
        1130                1135                    1140

Asp Glu Gly Gln Asn His Gln Gly Gln     Ser Cys Ile His Arg Pro
        1145                1150                    1155

Cys Gly Lys Gln Asp Ser Cys Pro Ser     Leu Leu Leu Asp His Ala
        1160                1165                    1170

Asp Val Val Asn Cys Thr Ser Ile Gly     Pro Gly Leu Met Lys Cys
        1175                1180                    1185

Ala Ile Thr Cys Gln Arg Gly Phe Ala     Leu Gln Ala Ser Ser Gly
        1190                1195                    1200

Gln Tyr Ile Arg Pro Met Gln Lys Glu     Ile Leu Leu Thr Cys Ser
        1205                1210                    1215

Ser Gly His Trp Asp Gln Asn Val Ser     Cys Leu Pro Val Asp Cys
        1220                1225                    1230

Gly Val Pro Asp Pro Ser Leu Val Asn     Tyr Ala Asn Phe Ser Cys
        1235                1240                    1245

Ser Glu Gly Thr Lys Phe Leu Lys Arg     Cys Ser Ile Ser Cys Val
        1250                1255                    1260

Pro Pro Ala Lys Leu Gln Gly Leu Ser     Pro Trp Leu Thr Cys Leu
        1265                1270                    1275

Glu Asp Gly Leu Trp Ser Leu Pro Glu     Val Tyr Cys Lys Leu Glu
        1280                1285                    1290

Cys Asp Ala Pro Pro Ile Ile Leu Asn     Ala Asn Leu Leu Leu Pro
        1295                1300                    1305

His Cys Leu Gln Asp Asn His Asp Val     Gly Thr Ile Cys Lys Tyr
        1310                1315                    1320

Glu Cys Lys Pro Gly Tyr Tyr Val Ala     Glu Ser Ala Glu Gly Lys
        1325                1330                    1335

Val Arg Asn Lys Leu Leu Lys Ile Gln     Cys Leu Glu Gly Gly Ile
        1340                1345                    1350

Trp Glu Gln Gly Ser Cys Ile Pro Val     Val Cys Glu Pro Pro Pro
        1355                1360                    1365

Pro Val Phe Glu Gly Met Tyr Glu Cys     Thr Asn Gly Phe Ser Leu
        1370                1375                    1380

Asp Ser Gln Cys Val Leu Asn Cys Asn     Gln Glu Arg Glu Lys Leu
        1385                1390                    1395

Pro Ile Leu Cys Thr Lys Glu Gly Leu     Trp Thr Gln Glu Phe Lys
        1400                1405                    1410

Leu Cys Glu Asn Leu Gln Gly Glu Cys     Pro Pro Pro Pro Ser Glu
        1415                1420                    1425

Leu Asn Ser Val Glu Tyr Lys Cys Glu     Gln Gly Tyr Gly Ile Gly
        1430                1435                    1440

Ala Val Cys Ser Pro Leu Cys Val Ile     Pro Pro Ser Asp Pro Val
        1445                1450                    1455

Met Leu Pro Glu Asn Ile Thr Ala Asp     Thr Leu Glu His Trp Met
        1460                1465                    1470

Glu Pro Val Lys Val Gln Ser Ile Val     Cys Thr Gly Arg Arg Gln
        1475                1480                    1485
```

```
Trp His Pro Asp Pro Val Leu Val His Cys Ile Gln Ser Cys Glu
            1490                1495                1500

Pro Phe Gln Ala Asp Gly Trp Cys Asp Thr Ile Asn Asn Arg Ala
1505                1510                1515

Tyr Cys His Tyr Asp Gly Gly Asp Cys Cys Ser Ser Thr Leu Ser
        1520                1525                1530

Ser Lys Lys Val Ile Pro Phe Ala Ala Asp Cys Asp Leu Asp Glu
    1535                1540                1545

Cys Thr Cys Arg Asp Pro Lys Ala Glu Glu Asn Gln
            1550                1555

<210> SEQ ID NO 3
<211> LENGTH: 11
<212> TYPE: PRT
<213> ORGANISM: Artificial Sequence
<220> FEATURE:
<223> OTHER INFORMATION: zinc binding motif
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (6)..(6)
<223> OTHER INFORMATION: Xaa is any amino acid
<220> FEATURE:
<221> NAME/KEY: misc_feature
<222> LOCATION: (7)..(7)
<223> OTHER INFORMATION: Xaa is any amino acid
<220> FEATURE:
<221> NAME/KEY: misc_feature
<222> LOCATION: (9)..(9)
<223> OTHER INFORMATION: Xaa is any amino acid
<220> FEATURE:
<221> NAME/KEY: misc_feature
<222> LOCATION: (10)..(10)
<223> OTHER INFORMATION: Xaa is any amino acid

<400> SEQUENCE: 3

His Glu Xaa Xaa His Xaa Xaa Gly Xaa Xaa His
1               5                   10

<210> SEQ ID NO 4
<211> LENGTH: 20
<212> TYPE: DNA
<213> ORGANISM: Artificial Sequence
<220> FEATURE:
<223> OTHER INFORMATION: primer RT-N-mid

<400> SEQUENCE: 4
gctcacacac cacaggaatg                                                   20

<210> SEQ ID NO 5
<211> LENGTH: 20
<212> TYPE: DNA
<213> ORGANISM: Artificial Sequence
<220> FEATURE:
<223> OTHER INFORMATION: primer PR-mid5

<400> SEQUENCE: 5
gctcacacac cacaggaatg                                                   20

<210> SEQ ID NO 6
<211> LENGTH: 22
```

```
<212> TYPE: DNA
<213> ORGANISM: Artificial Sequence
<220> FEATURE:
<223> OTHER INFORMATION: primer PR-mid3

<400> SEQUENCE: 6
gcattgtatc ttcaggagct tg                                              22

<210> SEQ ID NO 7
<211> LENGTH: 23
<212> TYPE: DNA
<213> ORGANISM: Artificial Sequence
<220> FEATURE:
<223> OTHER INFORMATION: primer PR-N5

<400> SEQUENCE: 7
gaagttgact tctggttctg tag                                             23

<210> SEQ ID NO 8
<211> LENGTH: 21
<212> TYPE: DNA
<213> ORGANISM: Artificial Sequence
<220> FEATURE:
<223> OTHER INFORMATION: primer PR-N3

<400> SEQUENCE: 8
ccctgggaag cgagtgaagc c                                               21

<210> SEQ ID NO 9
<211> LENGTH: 25
<212> TYPE: DNA
<213> ORGANISM: Artificial Sequence
<220> FEATURE:
<223> OTHER INFORMATION: primer RT-C

<400> SEQUENCE: 9
gcatttctta taagatcctt catgc                                           25

<210> SEQ ID NO 10
<211> LENGTH: 22
<212> TYPE: DNA
<213> ORGANISM: Artificial Sequence
<220> FEATURE:
<223> OTHER INFORMATION: primer PR-C5

<400> SEQUENCE: 10
gacagctgtc cgtcattgct gc                                              22

<210> SEQ ID NO 11
<211> LENGTH: 22
<212> TYPE: DNA
<213> ORGANISM: Artificial Sequence
<220> FEATURE:
<223> OTHER INFORMATION: primer PR-C3

<400> SEQUENCE: 11
cttactgcct ctgaggcagt gg                                              22

<210> SEQ ID NO 12
<211> LENGTH: 22
<212> TYPE: DNA
<213> ORGANISM: Artificial Sequence
<220> FEATURE:
<223> OTHER INFORMATION: primer from AL031290, nt. 64900-64879

<400> SEQUENCE: 12
```
ggaaagagca gagttcaccc at                                            22

<210> SEQ ID NO 13
<211> LENGTH: 21
<212> TYPE: DNA
<213> ORGANISM: Artificial Sequence
<220> FEATURE:
<223> OTHER INFORMATION: primer from AL031290, nt. 20499-20519

<400> SEQUENCE: 13
ccgtcttagt ccactgcatc c                                             21

<210> SEQ ID NO 14
<211> LENGTH: 20
<212> TYPE: DNA
<213> ORGANISM: Artificial Sequence
<220> FEATURE:
<223> OTHER INFORMATION: primer from vector pcDNA3.1+, nt. 1040-1021

<400> SEQUENCE: 14
ctagaaggca cagtcgaggc                                               20

<210> SEQ ID NO 15
<211> LENGTH: 33
<212> TYPE: DNA
<213> ORGANISM: Artificial Sequence
<220> FEATURE:
<223> OTHER INFORMATION: primer from SEQ ID NO:1, nt. 2210-2178

<400> SEQUENCE: 15
tgtcccactt gatggatcat ggtgtcggtg tgg                                33

<210> SEQ ID NO 16
<211> LENGTH: 26
<212> TYPE: DNA
<213> ORGANISM: Artificial Sequence
<220> FEATURE:
<223> OTHER INFORMATION: primer from SEQ ID NO:1, nt. 2196-2221

<400> SEQUENCE: 16
ccatcaagtg ggacatgttc tgggac                                        26

<210> SEQ ID NO 17
<211> LENGTH: 32
<212> TYPE: DNA
<213> ORGANISM: Artificial Sequence
<220> FEATURE:
<223> OTHER INFORMATION: primer from SEQ ID NO:1, nt. 5373-5354

<400> SEQUENCE: 17
gacgtaaagc ttctgatttt cttctgcctt gg                                 32

<210> SEQ ID NO 18
<211> LENGTH: 4
<212> TYPE: PRT
<213> ORGANISM: Artificial Sequence
<220> FEATURE:
<223> OTHER INFORMATION: synthetic linker in pPA2-mH

<400> SEQUENCE: 18

Lys Leu Gly Pro
1

<210> SEQ ID NO 19
<211> LENGTH: 10
<212> TYPE: PRT

```
<213> ORGANISM: Artificial Sequence
<220> FEATURE:
<223> OTHER INFORMATION: synthetic myc epitope in pPA2-mH

<400> SEQUENCE: 19

Glu Gln Lys Leu Ile Ser Glu Glu Asp Leu
1               5                   10

<210> SEQ ID NO 20
<211> LENGTH: 5
<212> TYPE: PRT
<213> ORGANISM: Artificial Sequence
<220> FEATURE:
<223> OTHER INFORMATION: synthetic linker in pPA2-mH

<400> SEQUENCE: 20

Asn Ser Ala Val Asp
1               5

<210> SEQ ID NO 21
<211> LENGTH: 30
<212> TYPE: DNA
<213> ORGANISM: Artificial Sequence
<220> FEATURE:
<223> OTHER INFORMATION: primer containing XhoI site, for amplifying
      IGFBP-5 cDNA

<400> SEQUENCE: 21
tccgctcgag atggtgttgc tcaccgcggt                                       30

<210> SEQ ID NO 22
<211> LENGTH: 29
<212> TYPE: DNA
<213> ORGANISM: Artificial Sequence
<220> FEATURE:
<223> OTHER INFORMATION: primer containing HindIII site, for amplifying
      IGFBP-5 cDNA

<400> SEQUENCE: 22
cgataagctt ctcaacgttg ctgctgtcg                                        29

<210> SEQ ID NO 23
<211> LENGTH: 6
<212> TYPE: PRT
<213> ORGANISM: Artificial Sequence
<220> FEATURE:
<223> OTHER INFORMATION: N-terminal sequence of degradation product of
      purified rIGFBP-5 digested with PAPP-A2

<400> SEQUENCE: 23

Lys Phe Val Gly Gly Ala
1               5

<210> SEQ ID NO 24
<211> LENGTH: 6
<212> TYPE: PRT
<213> ORGANISM: Artificial Sequence
<220> FEATURE:
<223> OTHER INFORMATION: N-terminal sequence of degradation product of
      purified rIGFBP-5 digested with PAPP-A2
<220> FEATURE:
<221> NAME/KEY: misc_feature
<222> LOCATION: (3)..(3)
<223> OTHER INFORMATION: Xaa is unknown

<400> SEQUENCE: 24

Leu Gly Xaa Phe Val His
1               5
```

<210> SEQ ID NO 25
<211> LENGTH: 1627
<212> TYPE: PRT
<213> ORGANISM: Homo sapiens

<400> SEQUENCE: 25

```
Met Arg Leu Trp Ser Trp Val Leu His Leu Gly Leu Ser Ala Ala
1               5                   10                  15

Leu Gly Cys Gly Leu Ala Glu Arg Pro Arg Ala Arg Arg Asp Pro
            20                  25                  30

Arg Ala Gly Arg Pro Pro Arg Pro Ala Ala Gly Pro Ala Thr Cys Ala
        35                  40                  45

Thr Arg Gly Pro Arg Pro Pro Arg Leu Ala Ala Ala Ala Ala Ala
    50                  55                      60

Gly Arg Ala Trp Glu Ala Val Arg Val Pro Arg Arg Gln Gln Arg
65                  70                  75                  80

Glu Ala Arg Gly Ala Thr Glu Glu Pro Ser Pro Ser Arg Ala Leu
                85                  90                  95

Tyr Phe Ser Gly Arg Gly Glu Gln Leu Arg Val Leu Arg Ala Asp Leu
                100                 105                 110

Glu Leu Pro Arg Asp Ala Phe Thr Leu Gln Val Trp Leu Arg Ala Glu
            115                 120                 125

Gly Gly Gln Arg Ser Pro Ala Val Ile Thr Gly Leu Tyr Asp Lys Cys
        130                 135                 140

Ser Tyr Ile Ser Arg Asp Arg Gly Trp Val Val Gly Ile His Thr Ile
145                 150                 155                 160

Ser Asp Gln Asp Asn Lys Asp Pro Arg Tyr Phe Phe Ser Leu Lys Thr
                165                 170                 175

Asp Arg Ala Arg Gln Val Thr Thr Ile Asn Ala His Arg Ser Tyr Leu
            180                 185                 190

Pro Gly Gln Trp Val Tyr Leu Ala Ala Thr Tyr Asp Gly Gln Phe Met
        195                 200                 205

Lys Leu Tyr Val Asn Gly Ala Gln Val Ala Thr Ser Gly Glu Gln Val
    210                 215                 220

Gly Gly Ile Phe Ser Pro Leu Thr Gln Lys Cys Lys Val Leu Met Leu
225                 230                 235                 240

Gly Gly Ser Ala Leu Asn His Asn Tyr Arg Gly Tyr Ile Glu His Phe
                245                 250                 255

Ser Leu Trp Lys Val Ala Arg Thr Gln Arg Glu Ile Leu Ser Asp Met
            260                 265                 270

Glu Thr His Gly Ala His Thr Ala Leu Pro Gln Leu Leu Leu Gln Glu
        275                 280                 285

Asn Trp Asp Asn Val Lys His Ala Trp Ser Pro Met Lys Asp Gly Ser
    290                 295                 300

Ser Pro Lys Val Glu Phe Ser Asn Ala His Gly Phe Leu Leu Asp Thr
305                 310                 315                 320

Ser Leu Glu Pro Pro Leu Cys Gly Gln Thr Leu Cys Asp Asn Thr Glu
                325                 330                 335

Val Ile Ala Ser Tyr Asn Gln Leu Ser Ser Phe Arg Gln Pro Lys Val
            340                 345                 350

Val Arg Tyr Arg Val Val Asn Leu Tyr Glu Asp Asp His Lys Asn Pro
        355                 360                 365
```

-continued

```
Thr Val Thr Arg Glu Gln Val Asp Phe Gln His His Gln Leu Ala Glu
370                 375                 380

Ala Phe Lys Gln Tyr Asn Ile Ser Trp Glu Leu Asp Val Leu Glu Val
385                 390                 395                 400

Ser Asn Ser Ser Leu Arg Arg Leu Ile Leu Ala Asn Cys Asp Ile
        405                 410                 415

Ser Lys Ile Gly Asp Glu Asn Cys Asp Pro Glu Cys Asn His Thr Leu
        420                 425                 430

Thr Gly His Asp Gly Asp Cys Arg His Leu Arg His Pro Ala Phe
        435                 440                 445

Val Lys Lys Gln His Asn Gly Val Cys Asp Met Asp Cys Asn Tyr Glu
450                 455                 460

Arg Phe Asn Phe Asp Gly Gly Glu Cys Cys Asp Pro Glu Ile Thr Asn
465                 470                 475                 480

Val Thr Gln Thr Cys Phe Asp Pro Asp Ser Pro His Arg Ala Tyr Leu
                485                 490                 495

Asp Val Asn Glu Leu Lys Asn Ile Leu Lys Leu Asp Gly Ser Thr His
            500                 505                 510

Leu Asn Ile Phe Phe Ala Lys Ser Ser Glu Glu Glu Leu Ala Gly Val
            515                 520                 525

Ala Thr Trp Pro Trp Asp Lys Glu Ala Leu Met His Leu Gly Gly Ile
530                 535                 540

Val Leu Asn Pro Ser Phe Tyr Gly Met Pro Gly His Thr His Thr Met
545                 550                 555                 560

Ile His Glu Ile Gly His Ser Leu Gly Leu Tyr His Val Phe Arg Gly
                565                 570                 575

Ile Ser Glu Ile Gln Ser Cys Ser Asp Pro Cys Met Glu Thr Glu Pro
            580                 585                 590

Ser Phe Glu Thr Gly Asp Leu Cys Asn Asp Thr Asn Pro Ala Pro Lys
        595                 600                 605

His Lys Ser Cys Gly Asp Pro Gly Pro Gly Asn Asp Thr Cys Gly Phe
610                 615                 620

His Ser Phe Phe Asn Thr Pro Tyr Asn Asn Phe Met Ser Tyr Ala Asp
625                 630                 635                 640

Asp Asp Cys Thr Asp Ser Phe Thr Pro Asn Gln Val Ala Arg Met His
                645                 650                 655

Cys Tyr Leu Asp Leu Val Tyr Gln Gly Trp Gln Pro Ser Arg Lys Pro
            660                 665                 670

Ala Pro Val Ala Leu Ala Pro Gln Val Leu Gly His Thr Thr Asp Ser
            675                 680                 685

Val Thr Leu Glu Trp Phe Pro Pro Ile Asp Gly His Phe Phe Glu Arg
690                 695                 700

Glu Leu Gly Ser Ala Cys His Leu Cys Leu Glu Gly Arg Ile Leu Val
705                 710                 715                 720

Gln Tyr Ala Ser Asn Ala Ser Ser Pro Met Pro Cys Ser Pro Ser Gly
                725                 730                 735

His Trp Ser Pro Arg Glu Ala Glu Gly His Pro Asp Val Glu Gln Pro
            740                 745                 750

Cys Lys Ser Ser Val Arg Thr Trp Ser Pro Asn Ser Ala Val Asn Pro
        755                 760                 765

His Thr Val Pro Pro Ala Cys Pro Glu Pro Gln Gly Cys Tyr Leu Glu
770                 775                 780
```

-continued

Leu Glu Phe Leu Tyr Pro Leu Val Pro Glu Ser Leu Thr Ile Trp Val
785                 790                 795                 800

Thr Phe Val Ser Thr Asp Trp Asp Ser Ser Gly Ala Val Asn Asp Ile
            805                 810                 815

Lys Leu Leu Ala Val Ser Gly Lys Asn Ile Ser Leu Gly Pro Gln Asn
            820                 825                 830

Val Phe Cys Asp Val Pro Leu Thr Ile Arg Leu Trp Asp Val Gly Glu
            835                 840                 845

Glu Val Tyr Gly Ile Gln Ile Tyr Thr Leu Asp Glu His Leu Glu Ile
            850                 855                 860

Asp Ala Ala Met Leu Thr Ser Thr Ala Asp Thr Pro Leu Cys Leu Gln
865                 870                 875                 880

Cys Lys Pro Leu Lys Tyr Lys Val Val Arg Asp Pro Pro Leu Gln Met
            885                 890                 895

Asp Val Ala Ser Ile Leu His Leu Asn Arg Lys Phe Val Asp Met Asp
            900                 905                 910

Leu Asn Leu Gly Ser Val Tyr Gln Tyr Trp Val Ile Thr Ile Ser Gly
            915                 920                 925

Thr Glu Glu Ser Glu Pro Ser Pro Ala Val Thr Tyr Ile His Gly Arg
930                 935                 940

Gly Tyr Cys Gly Asp Gly Ile Ile Gln Lys Asp Gln Gly Glu Gln Cys
945                 950                 955                 960

Asp Asp Met Asn Lys Ile Asn Gly Asp Gly Cys Ser Leu Phe Cys Arg
            965                 970                 975

Gln Glu Val Ser Phe Asn Cys Ile Asp Glu Pro Ser Arg Cys Tyr Phe
            980                 985                 990

His Asp Gly Asp Gly Val Cys Glu Glu Phe Glu Gln Lys Thr Ser Ile
            995                 1000                1005

Lys Asp Cys Gly Val Tyr Thr Pro Gln Gly Phe Leu Asp Gln Trp
1010                1015                1020

Ala Ser Asn Ala Ser Val Ser His Gln Asp Gln Gln Cys Pro Gly
1025                1030                1035

Trp Val Ile Ile Gly Gln Pro Ala Ala Ser Gln Val Cys Arg Thr
1040                1045                1050

Lys Val Ile Asp Leu Ser Glu Gly Ile Ser Gln His Ala Trp Tyr
1055                1060                1065

Pro Cys Thr Ile Ser Tyr Pro Tyr Ser Gln Leu Ala Gln Thr Thr
1070                1075                1080

Phe Trp Leu Arg Ala Tyr Phe Ser Gln Pro Met Val Ala Ala Ala
1085                1090                1095

Val Ile Val His Leu Val Thr Asp Gly Thr Tyr Tyr Gly Asp Gln
1100                1105                1110

Lys Gln Glu Thr Ile Ser Val Gln Leu Leu Asp Thr Lys Asp Gln
1115                1120                1125

Ser His Asp Leu Gly Leu His Val Leu Ser Cys Arg Asn Asn Pro
1130                1135                1140

Leu Ile Ile Pro Val Val His Asp Leu Ser Gln Pro Phe Tyr His
1145                1150                1155

Ser Gln Ala Val Arg Val Ser Phe Ser Ser Pro Leu Val Ala Ile
1160                1165                1170

Ser Gly Val Ala Leu Arg Ser Phe Asp Asn Phe Asp Pro Val Thr
1175                1180                1185

-continued

Leu Ser Ser Cys Gln Arg Gly Glu Thr Tyr Ser Pro Ala Glu Gln
1190                    1195                1200

Ser Cys Val His Phe Ala Cys Glu Lys Thr Asp Cys Pro Glu Leu
1205                    1210                1215

Ala Val Glu Asn Ala Ser Leu Asn Cys Ser Ser Asp Arg Tyr
1220                    1225                1230

His Gly Ala Gln Cys Thr Val Ser Cys Arg Thr Gly Tyr Val Leu
1235                    1240                1245

Gln Ile Arg Arg Asp Asp Glu Leu Ile Lys Ser Gln Thr Gly Pro
1250                    1255                1260

Ser Val Thr Val Thr Cys Thr Glu Gly Lys Trp Asn Lys Gln Val
1265                    1270                1275

Ala Cys Glu Pro Val Asp Cys Ser Ile Pro Asp His His Gln Val
1280                    1285                1290

Tyr Ala Ala Ser Phe Ser Cys Pro Glu Gly Thr Thr Phe Gly Ser
1295                    1300                1305

Gln Cys Ser Phe Gln Cys Arg His Pro Ala Gln Leu Lys Gly Asn
1310                    1315                1320

Asn Ser Leu Leu Thr Cys Met Glu Asp Gly Leu Trp Ser Phe Pro
1325                    1330                1335

Glu Ala Leu Cys Glu Leu Met Cys Leu Ala Pro Pro Pro Val Pro
1340                    1345                1350

Asn Ala Asp Leu Gln Thr Ala Arg Cys Arg Glu Asn Lys His Lys
1355                    1360                1365

Val Gly Ser Phe Cys Lys Tyr Lys Cys Lys Pro Gly Tyr His Val
1370                    1375                1380

Pro Gly Ser Ser Arg Lys Ser Lys Lys Arg Ala Phe Lys Thr Gln
1385                    1390                1395

Cys Thr Gln Asp Gly Ser Trp Gln Glu Gly Ala Cys Val Pro Val
1400                    1405                1410

Thr Cys Asp Pro Pro Pro Lys Phe His Gly Leu Tyr Gln Cys
1415                    1420                1425

Thr Asn Gly Phe Gln Phe Asn Ser Glu Cys Arg Ile Lys Cys Glu
1430                    1435                1440

Asp Ser Asp Ala Ser Gln Gly Leu Gly Ser Asn Val Ile His Cys
1445                    1450                1455

Arg Lys Asp Gly Thr Trp Asn Gly Ser Phe His Val Cys Gln Glu
1460                    1465                1470

Met Gln Gly Gln Cys Ser Val Pro Asn Glu Leu Asn Ser Asn Leu
1475                    1480                1485

Lys Leu Gln Cys Pro Asp Gly Tyr Ala Ile Gly Ser Glu Cys Ala
1490                    1495                1500

Thr Ser Cys Leu Asp His Asn Ser Glu Ser Ile Ile Leu Pro Met
1505                    1510                1515

Asn Val Thr Val Arg Asp Ile Pro His Trp Leu Asn Pro Thr Arg
1520                    1525                1530

Val Glu Arg Val Val Cys Thr Ala Gly Leu Lys Trp Tyr Pro His
1535                    1540                1545

Pro Ala Leu Ile His Cys Val Lys Gly Cys Glu Pro Phe Met Gly
1550                    1555                1560

Asp Asn Tyr Cys Asp Ala Ile Asn Asn Arg Ala Phe Cys Asn Tyr
1565                    1570                1575

-continued

```
Asp Gly Gly Asp Cys Cys Thr Ser Thr Val Lys Thr     Lys Lys Val
    1580            1585            1590

Thr Pro Phe Pro Met Ser Cys Asp Leu Gln Gly Asp     Cys Ala Cys
    1595            1600            1605

Arg Asp Pro Gln Ala Gln Glu His Ser Arg Lys Asp     Leu Arg Gly
    1610            1615            1620

Tyr Ser His Gly
    1625

<210> SEQ ID NO 26
<211> LENGTH: 11
<212> TYPE: PRT
<213> ORGANISM: Artificial Sequence
<220> FEATURE:
<223> OTHER INFORMATION: An elongated zinc binding motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(19)
<223> OTHER INFORMATION: Xaa can be any naturally occurring amino acid

<400> SEQUENCE: 26

His Glu Xaa Xaa His Xaa Xaa Gly Xaa Xaa His
1               5                   10
```